US009854799B2

(12) United States Patent
Blank et al.

(10) Patent No.: US 9,854,799 B2
(45) Date of Patent: Jan. 2, 2018

(54) MEANS AND METHODS FOR RHAMNOLIPID PRODUCTION

(71) Applicant: Amlika Mercantile Private Limited, Mumbai (IN)

(72) Inventors: Lars Blank, Dortmund (DE); Frank Rosenau, Kirchheim Unter Teck (DE); Susanne Wilhelm, Essen (DE); Andreas Wittgens, Viersen (DE); Till Tiso, Aachen (DE)

(73) Assignee: Amlika Mercantile Private Limited, Mumbai (IN)

( * ) Notice: Subject to any disclaimer, the term of this patent is extended or adjusted under 35 U.S.C. 154(b) by 32 days.

(21) Appl. No.: 14/346,354

(22) PCT Filed: Sep. 21, 2012

(86) PCT No.: PCT/EP2012/068630
§ 371 (c)(1),
(2) Date: Mar. 21, 2014

(87) PCT Pub. No.: WO2013/041670
PCT Pub. Date: Mar. 28, 2013

(65) Prior Publication Data
US 2014/0235561 A1    Aug. 21, 2014

(30) Foreign Application Priority Data
Sep. 21, 2011    (EP) .................................... 11182080

(51) Int. Cl.
| | | |
|---|---|---|
| *C12N 9/10* | (2006.01) | |
| *C12N 15/82* | (2006.01) | |
| *C12N 15/11* | (2006.01) | |
| *C12N 9/24* | (2006.01) | |
| *A01N 43/16* | (2006.01) | |
| *C12P 19/44* | (2006.01) | |
| *C12P 7/64* | (2006.01) | |
| *A01N 63/02* | (2006.01) | |

(52) U.S. Cl.
CPC ............. *A01N 43/16* (2013.01); *A01N 63/02* (2013.01); *C12N 9/10* (2013.01); *C12N 9/1029* (2013.01); *C12N 9/1051* (2013.01); *C12P 7/64* (2013.01); *C12P 19/44* (2013.01)

(58) Field of Classification Search
CPC .................................... C12N 9/10; C12P 7/64
USPC .................... 435/252.3, 254.2, 74
See application file for complete search history.

(56) References Cited

U.S. PATENT DOCUMENTS

| 7,199,233 B1 | 4/2007 | Jensen et al. |
|---|---|---|
| 2006/0014146 A1 | 1/2006 | Soucaille et al. |

FOREIGN PATENT DOCUMENTS

| WO | WO-01/92655 A1 | 12/2001 |
|---|---|---|
| WO | WO-2004/040984 A1 | 5/2004 |
| WO | WO-2008/013899 A2 | 1/2008 |
| WO | WO-2011/056871 A2 | 5/2011 |
| WO | WO-2012013554 A1 | 2/2012 |

OTHER PUBLICATIONS

Ochhsner et al., Appld and Envn Microbiol 1995, pp. 3503-3506.*
Kay Terpe Appl. Microbiol. Biotech. 2006, 72, pp. 211-222).*
Tegel et al. FEBS Journal, published Jan. 12, 2011, 278, pp. 729-739.*
Pagratis et al. Biotech and Bioeng. 1993, 41 pp, 837-845.*
Zhu et al.Journal of Bacteriology, May 2008, p. 3147-3154.*
Klinke et al. Appl Environ Micriobiol,1999, p. 540-548.*
Devos et al., (Proteins: Structure, Function and Genetics, 2000, vol. 41: 98-107.*
Kisselev L., (Structure, 2002, vol. 10: 8-9.*
Witkowski et al., (Biochemistry 38:11643-11650, 1999.*
Whisstock et al., (Quarterly Reviews of Biophysics 2003, vol. 36 (3): 307-340.*
Abdel-Mawgoud, A.M. et al., Rhamnolipids: diversity of structures, microbial origins and roles, Applied Microbiology and Biotechnology, 86(5):1323-1336 (2010).
Al-Tahhan, R.A. et al., Rhamnolipid-induced removal of lipopolysaccharide from Pseudomonas aeruginosa: effect on cell surface properties and interaction with hydrophobic substrates, Applied and Environmental Microbiology, 66(8):3262-3268 (2000).
Basu, A. et al., Preferential utilization of aromatic compounds over glucose by Pseudomonas putida CSV86, Applied Microbiology and Biotechnology, 72(3):2226-2230 (2006).
Behrends, V. et al., Time-resolved metabolic footprinting for non-linear modeling of bacterial substrate utilization, Applied and Environmental Microbioligy, 75(8):2453-2463 (2009).
Boekema, B.K. et al., Hexadecane and Tween 80 stimulate lipase production in Burkholderia glumae by different mechanisms, Applied and Environmental Microbiology, 73(12):3838-3844 (2007).

(Continued)

*Primary Examiner* — Robert Mondesi
*Assistant Examiner* — Md. Younus Meah
(74) *Attorney, Agent, or Firm* — Choate, Hall & Stewart LLP; Brenda Herschbach Jarrell; Robert N. Sahr

(57) ABSTRACT

Provided is a host cell comprising a rhlA gene or an ortholog thereof, under the control of a heterologous promoter and a rhlB gene or an ortholog thereof, under the control of a heterologous promoter. The host cell is capable of achieving a carbon yield of more than 0.18 Cmol rhamnolipid/Cmol substrate. Provided is also a method of producing rhamnolipids, employing such a host cell.

20 Claims, 17 Drawing Sheets

(56) References Cited

OTHER PUBLICATIONS

Buell, C.R. et al., The complete genome sequence of the Arabidopsis and tomato pathogen Pseudomonas syringae pv. tomato DC3000, Proceedings of the National Academy of Science, 100(18): 10181-10186 (2003).
Daniels, C. et al., Global regulation of food supply by Pseudomonas putida DOT-T1E, Journal of Bacteriology, 192(8):2169-2181 (2010).
Dubeau, D. et al., Burkholderia thailandensis harbors two identical rhl gene clusters responsible for the biosynthesis of rhamnolipids, BMC Microbiology, 9:263-274 (2009).
Glick, R. et al., Increase in rhamnolipid synthesis under iron-limiting conditions influences surface motility and biofilm formation in Pseudomonas aeruginosa, Journal of Bacteriology, 192(12):2973-2980 (2010).
Hancock, R.E. and Carey, A.M., Outer membrane of Pseudomonas aeruginosa: heat-2-mercaptoethanol-modifiable proteins, Journal of Bacteriology, 140(3):902-910 (1979).
Hervás, A.B. et al., Transcriptome analysis of Pseudomonas putida in response to nitrogen availability, Journal of Bacteriology, 190(1):416-420 (2008).
Joardar, V. et al., Whole-genome sequence analysis of Pseudomonas syringae pv. phaseolicola 1448A reveals divergence among pathovars in genes involved in virulence and transposition, Bacteriology, 187(18):6488-6498 (2005).
Kendall, K.J. and Cohen, S.N., Plasmid transfer in *Streptomyces lividans*: identification of a kil-kor system associated with the transfer region of pIJ101, Journal of Bacteriology, 169(9):4177-4183 (1987).
Kim, G.J. et al., High Cell Density Cultivation of Pseudomonas putida BM01 Using Flucose, Journal of Microbiology and Biotechnology, 6(3): 221-224 (1996).
Medina, G. et al., Transcriptional regulation of Pseudomonas aeruginosa rhIR, encoding a quorum-sensing regulatory protein, Microbiology, 149(11):3073-3081 (2003).
Pearson, J.P. et al., Roles of Pseudomonas aeruginosa las and rhl quorum-sensing systems in control of elastase and rhamnolipid biosynthesis genes, Journal of Bacteriology, 179(18):5756-5767 (1997).
Postma, P.W. et al., Phosphoenolpyruvate:carbohydrate phosphotransferase systems of bacteria, Microbiol Reviews, 57(3):543-594 (1993).
Ramos-Díaz, M.A. and Ramos, J.L., Combined physical and genetic map of the Pseudomonas putida KT2440 chromosome, Journal of Bacteriology, 180(23):6352-6363 (1998).
Rehm, B.H. et al., A new metabolic link between fatty acid de novo synthesis and polyhydroxyalkanoic acid synthesis. The PHAG gene from Pseudomonas putida KT2440 encodes a 3-hydroxyacyl-acyl carrier protein-coenzyme a transferase, Journal of Biological Chemistry, 273(37):24044-24051 (1998).
Sezonov, G. et al., *Escherichia coli* physiology in Luria-Bertani broth, Journal of Bacteriology, 189(23):8746-8749 (2007).
Van Gelder, P. et al., Sucrose transport through maltoporin mutants of *Escherichia coli*, Protein Engineering, 14(11):943-948 (2001).
Vogel, H.J. and Bonner, D.M., Acetylornithinase of *Escherichia coli*: partial purification and some properties, 218(1):97-106 (1956).
Weiss, W.A. et al., Recognizing and exploiting differences between RNAi and small-molecule inhibitors, Nature Chemical Biology, 3(12):739-744 (2007).
Xaxier, J.B. et al., A molecular mechanism that stabilizes cooperative secretions in Pseudomonas aeruginosa, Molecular Microbiology, 79(1):166-179 (2011).
Cha, M. et al., Heterologous production of *Pseudomonas aeruginosa* EMS1 biosurfactant in *Pseudomonas putida*, Bioresource Technology, 99: 2192-2199 (2008).
Daran-Lapujade, P. et al., The fluxes through glycolytic enzymes in *Saccharomyces cerevisiae* are predominantly regulated at post-transcriptional levels, PNAS, 104: 15753-15758 (2007).
Kerkhoven, E.J et al., Applications of computational modeling in metabolic engineering of yeast, FEMS Yeast Research, 1-13 (2015).
Müller, M.M. et al., *Pseudomonas aeruginosa* PAO1 as a model for rhamnolipid production in bioreactor systems, Appl. Microbiol. Biotechnol., 87: 167-175 (2010).
Sudarsan, S. et al., The functional structure of central carbon metabolism in Pseudomonas putida KT2440, Appl. Environ. Microbiol., 80(17): 5292-5303 (2014).
Cabrera-Valladares. N. et al., Monorhamnolipids and 3-(3-hydroxyalkanoyloxy) alkanoic acids (HAAs) production using *Escherichia coli* as a heterologous host, Appl. Microbiol. Biotechnol., 73: 187-194 (2006).
Choi, M.H. et al., Metabolic relationship between polyhydroxyalkanoic acid and rhamnolipid synthesis in Pseudomonas aeruginosa: Comparative $^{13}C$ NMR analysis of the products in wild-type and mutants, Journal of Biotechnology, 151: 30-42 (2011).
International Search Report for PCT/EP2012/068630, 6 pages (Jan. 7, 2013).
Toribio, J. et al., Rhamnolipids: Production in bacteria other than Pseudomonas aeruginosa, Eur. J. Lipid Sci. Technol., 112: 1082-1087 (2010).
Wittgens, A. et al., Growth independent rhamnolipid production from glucose using the nonpathogenic Pseudomonas putida KT2440, Microbial Cell Factories, 10(1): 80 1-17 (2011).
Written Opinion for PCT/EP2012/068630, 5 pages (Jan. 7, 2013).
Keasling, J.D., Manufacturing Molecules Through Metabolic Engineering, Science, 330: 1355-1358 (2010).
Nielsen, J. and Keasling, J.D., Engineering Cellular Metabolism, Cell, 164: 1185-1197 (2016).

\* cited by examiner

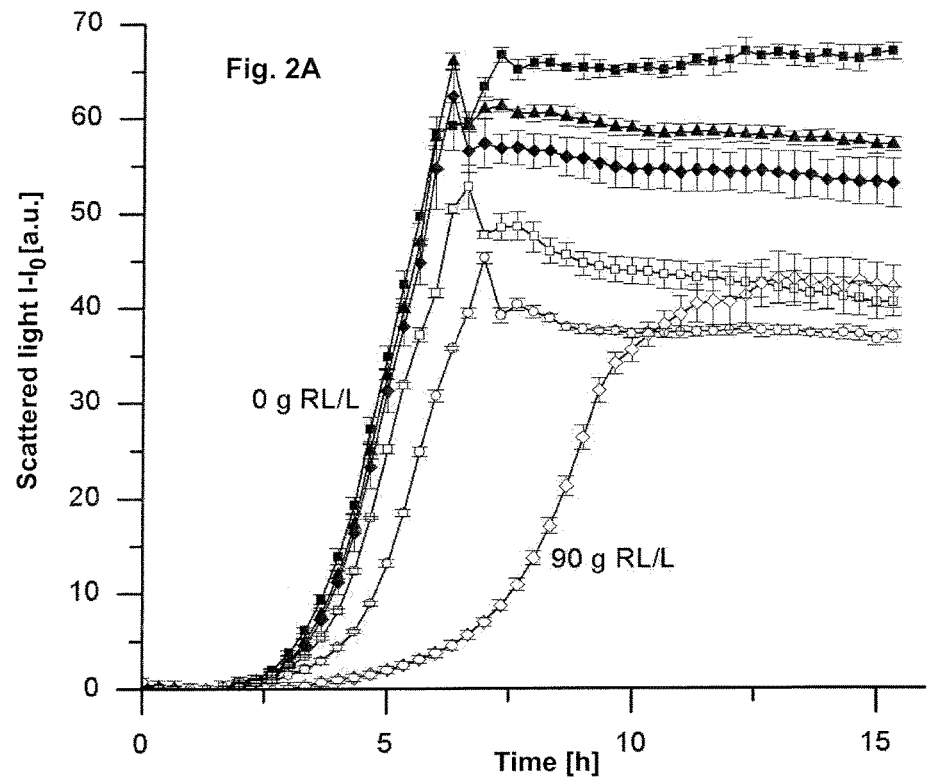
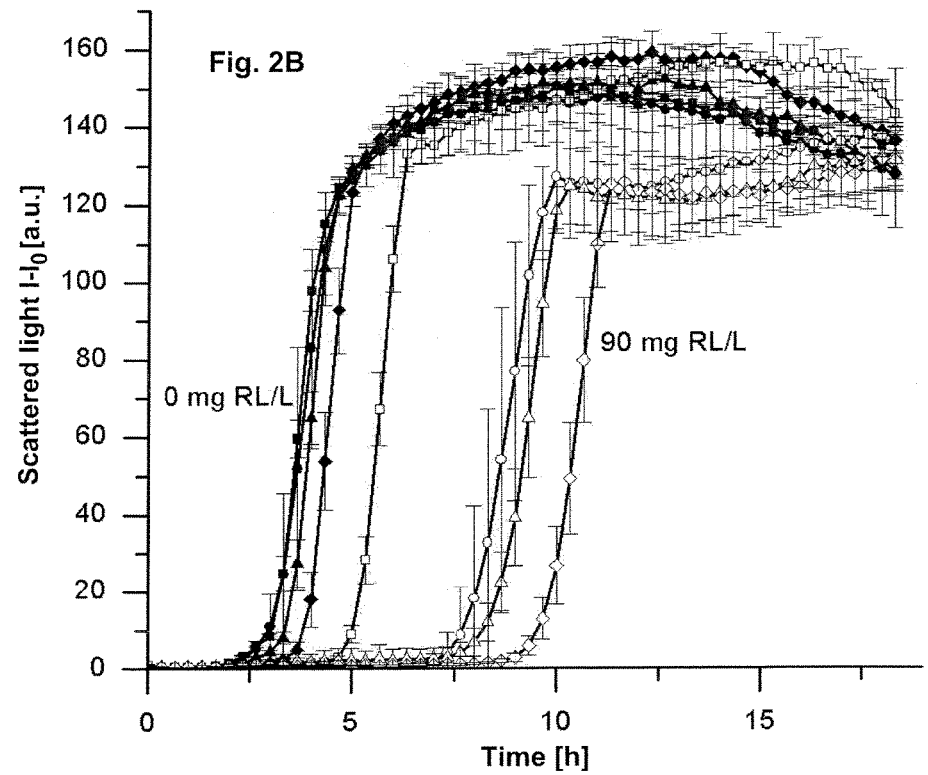

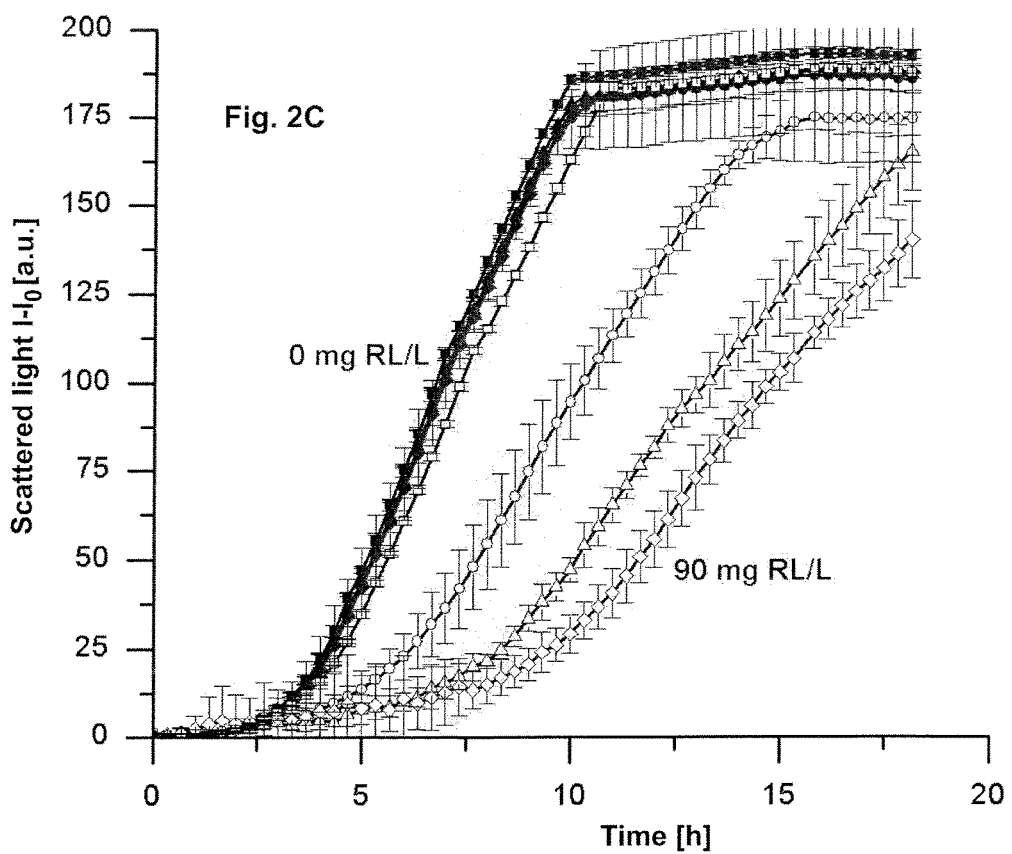
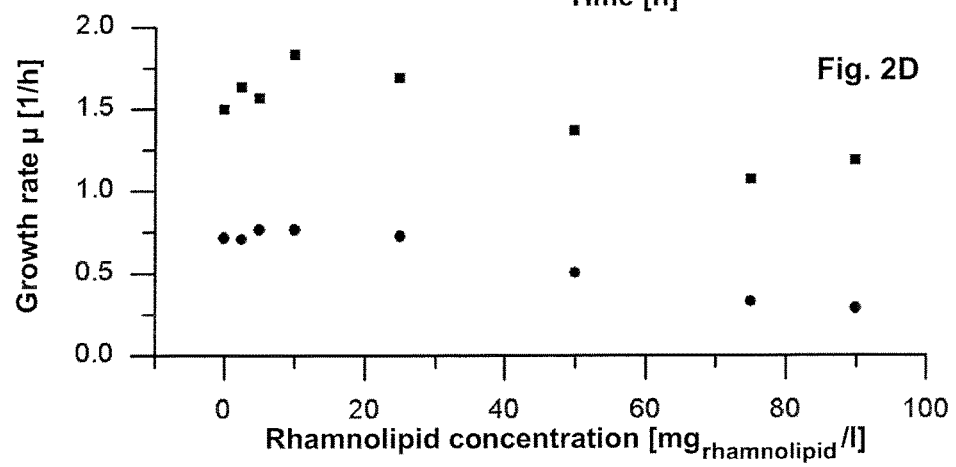
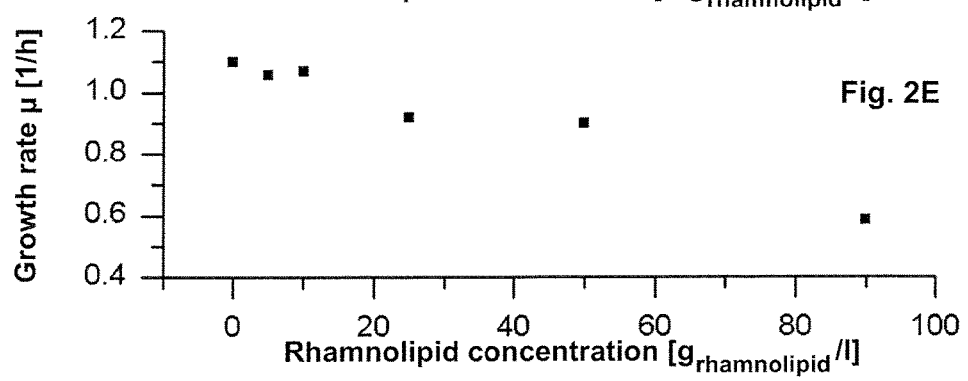

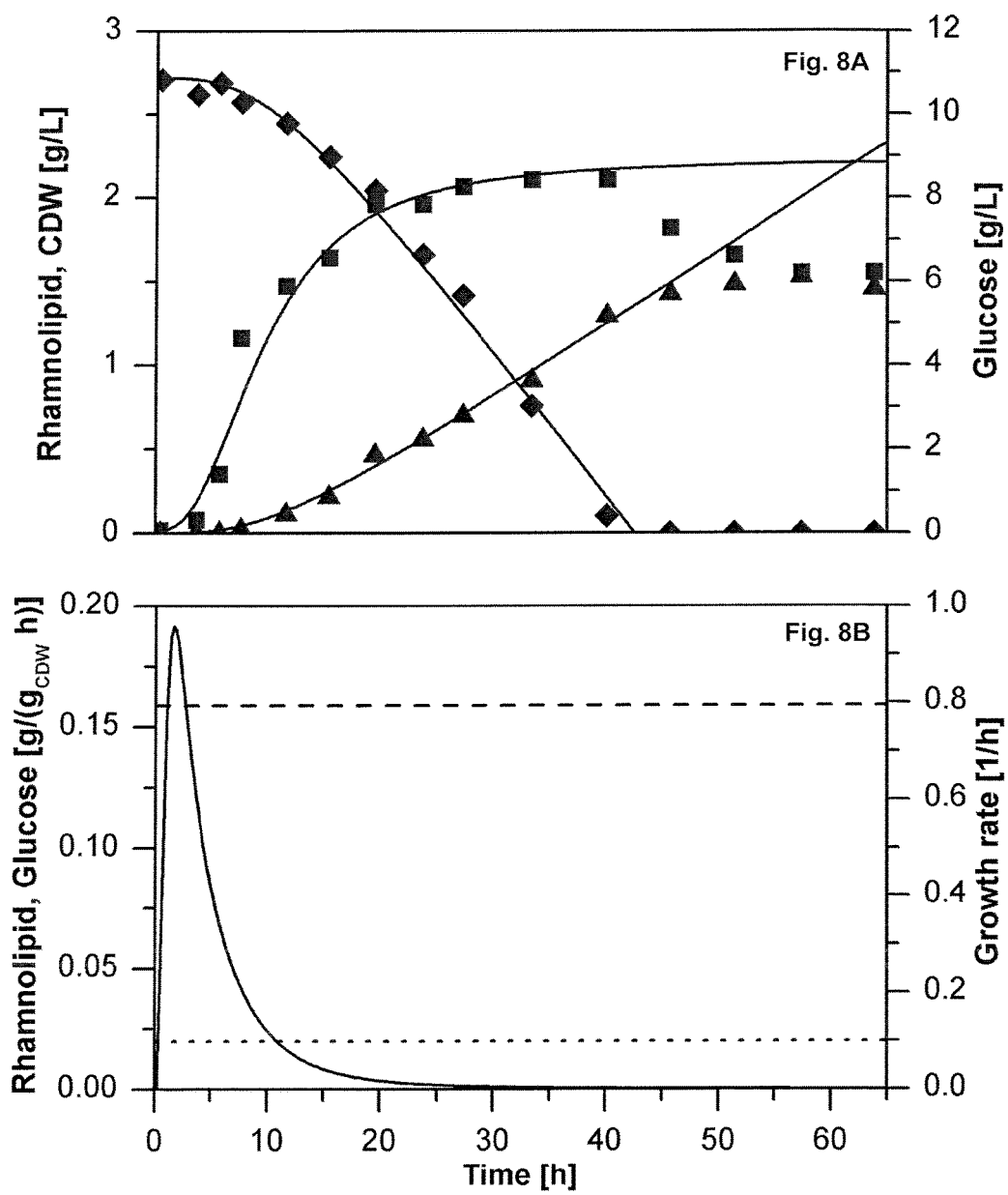

| Organism | Substrate (g/L) | Cell Dry Weight (g/L) | Yield (Cmol$_{rhamnolipid}$/ Cmol$_{substrate}$) | Maximal Titer (g/L) | Rhamnolipid Production Rate (g/g$_{CDW}$ h) | Reference |
|---|---|---|---|---|---|---|
| E. coli W3110 | Glucose (5) | not given | 0.04 | 0.12 | not given | 1 |
| P. putida KT2440 | LB + Glucose (10) | 1.2 | 0.09 | 0.6 | 0,020* | 2 |
| P. aeruginosa PAO1 | Sunflower Oil (250) | 16.3 | 0.14 | 39 | 0,027* | 3 |
| P. putida 1067 | Soybean Oil (20) | 3.2 | 0.17 | 7.3 | 0,031* | 4 |
| P. sp. DSM 2874 | Oleic Acid (198) | 48.0 | 0.18 | 45 | 0,001* | 5 |
| P. putida KT42C1 | Glucose (10) | 2.0 | 0.23 | 1.5 | 0,018 | 6 |

| retention time (min) | molecular mass (m/z) | composition of rhamnolipids |
| --- | --- | --- |
| 12.65 | 733.5 | Rha-Rha-$C_{12}$-$C_{14}$ / Rha-Rha-$C_{14}$-$C_{12}$ |
| 16.58 | 761.7 | Rha-Rha-$C_{14}$-$C_{14}$ |
| 20.11 | 789.6 | Rha-Rha-$C_{14}$-$C_{16}$ / Rha-Rha-$C_{16}$-$C_{14}$ |

| microorganism | MIC (µg/mL) |
|---|---|
| P. putida | > 500 |
| P. aeruginosa | > 500 |
| S. marcescens | > 500 |
| B. subtilis | 80 |
| S. aureus | 10 |

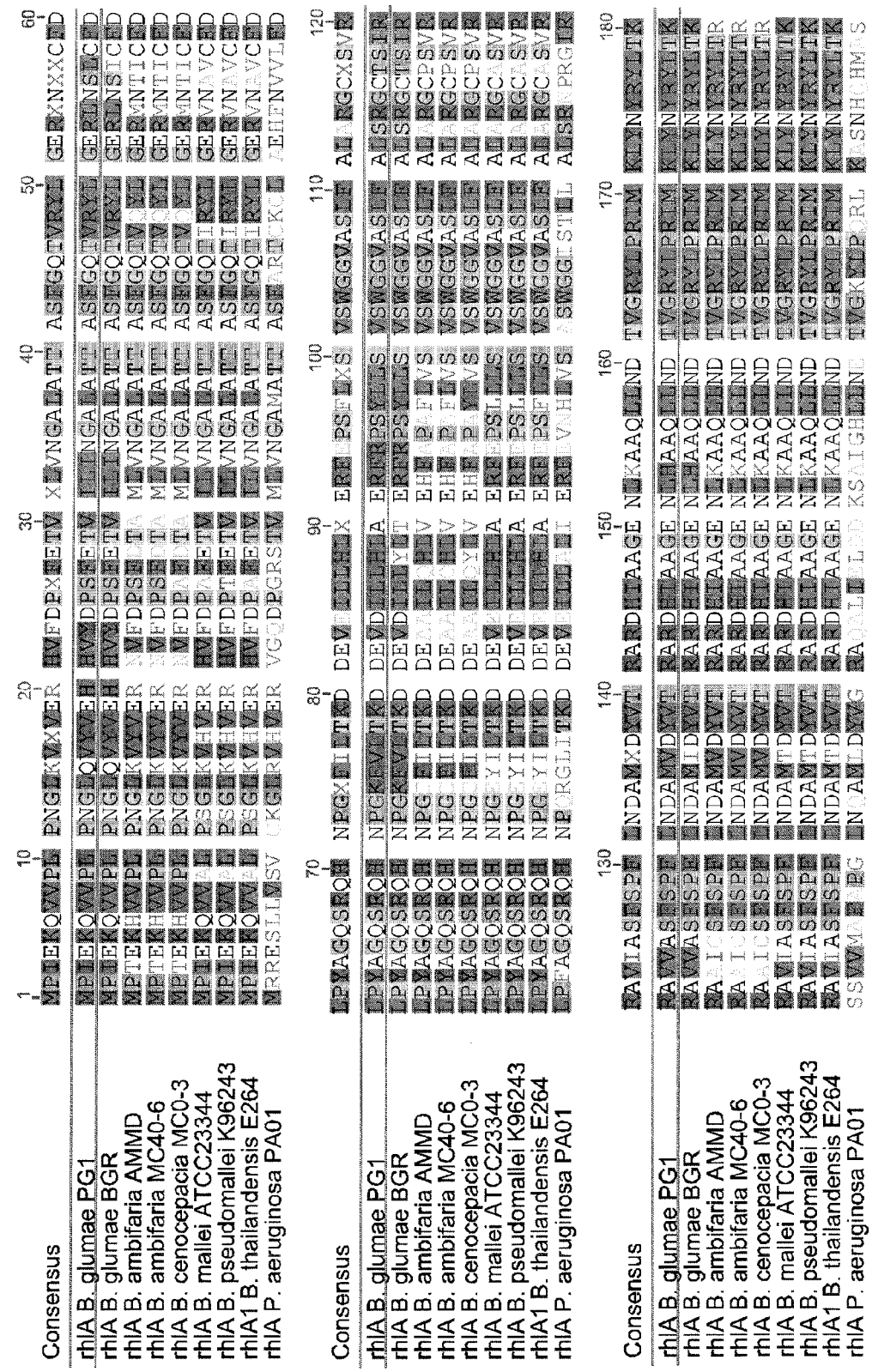
Fig. 17 (cont. on next page)

Fig. 17 (cont. from prev. page)

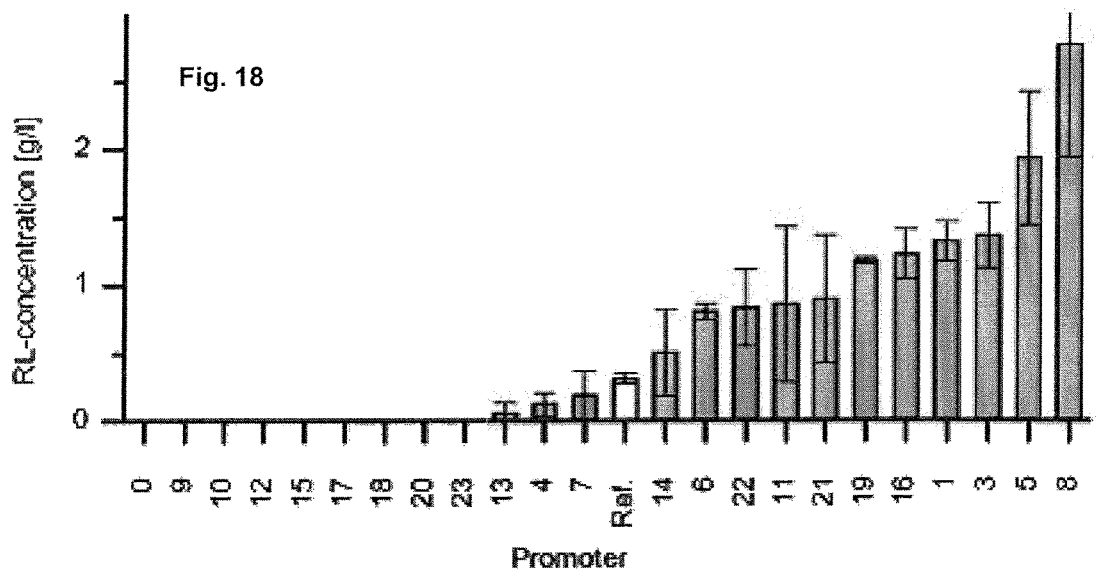

Fig. 18

5'-AGCTCTTGACAAGGTCGGAAAATTGAAGTATAATATCAGT-3'

5'-TTTCCTTGACAAGCCTAGTTTCGCCATTTATAATGACTCG-3'

5'-GGTGGTTGACATTGGCATTACAACGTATTATAATTTAGCG-3'

5'-TAGAGTTGACACACCTTCGGGTGGGCCTTATAATACTCGC-3'

5'-(A/T/G)(G/T/A)(C/T/G)(T/C/A/G)(C/G)TTGACA(A/T/C)(G/T/A)(G/C)(T/C/G)(C/T)
(G/A/T)(G/T/C)(A/T/G)(A/T/G)(A/T/C/G)(A/C/T)(T/G/A)(T/C/G)(G/C)(A/T/C)
(A/T/C)(G/T)TATAAT(A/G/T)(T/A/C)(C/A/T)(A/T/G/C)(G/C)(T/G/C)-3'

(SEQ ID NO:16)

Fig. 19

MEANS AND METHODS FOR RHAMNOLIPID PRODUCTION

CROSS REFERENCE TO RELATED APPLICATIONS

This application is a 35 U.S.C. §371 National Stage Application of International Application No. PCT/EP2012/068630, filed Sep. 21, 2012, which claims priority to European Patent Application serial number 11182080.9, filed Sep. 21, 2011, the entire contents of which are incorporated by reference.

FIELD OF THE INVENTION

The present invention relates to a host cell with a rhlA gene and a rhlB gene under the control of heterologous promoters. Provided is also a method of producing rhamnolipids that employs a respective host cell.

BACKGROUND OF THE INVENTION

In recent years biosurfactants have attracted increasing interest since they show a number of advantages over surfactants of petrochemical origin in terms of ecological acceptance, low toxicity and sustainability. Biosurfactants also have a huge application potential, for example in pharmaceutical and chemical industry or as emulsifier in cosmetics and foods.

Among the best established biosurfactants are the rhamnolipids, which have been first described more than sixty years ago (Jarvis, F. G., & Johnson, M. J., J. Am. Chem. Society (1949) 71, 4124-4126). Rhamnolipids are glycosides with one (mono-rhamnolipid) or two rhamnose-units (di-rhamnolipid) as the glycon portion and one to three β-hydroxy-fatty acid moieties as the aglycon portion. The rhamnose-moiety and the lipid moiety are linked via an O-glycosidic bond. If a plurality of β-hydroxy-fatty acid moieties is present, they are linked to each other by an ester bond that involves the β-hydroxy group(s). The terminal carboxyl group may be a free carboxylic acid group or a methyl ester. Rhamnolipids are produced by two rhamnosyltransferases encoded by rhlA, rhlB and rhlC. The rhlA and rhlB genes form an operon, encoding subunits A and B of rhamnosyltransferase 1, while rhlC encodes rhamnosyltransferase 2. RhlC is part of an operon together with a gene (PA1131) of so far unknown function. Rhamnosyltransferase 1A is responsible for the synthesis of the fatty acid dimer moiety of rhamnolipids and free 3-(3-hydroxyalkanoyloxy)alkanoic acids (HAAs), the precursors for rhamnolipid production. Mono-rhamnolipids are then synthesized by Rhamnosyltransferase 1B, which links a rhamnose molecule to a hydroxyalkanoic acid. Rhamnosyltransferase 2 generates di-rhamnolipis by adding a second rhamnose molecule to mono-rhamnolipids. Rhamnolipids have been found to be produced by a number of different bacteria (for an overview see Abdel-Mawgoud, A. M., et al., Appl. Microbiol. Biotechnol (2010) 86, 1323-1336) and potential Rhamnosyltransferase 1 and 2 genes keep being reported.

Industrial efforts to use microorganisms instead of traditional chemical processes increase, as biocatalysis typically allows the use of more moderate temperatures and ambient pressure and enzymes generally have a high selectivity directing reactions to the formation of a particular product. In fermentation whole cells carry out complex reaction cascades leading to a desired product. A fermentation based process thus only requires downstream processing, whereas upstream operations such as precursor synthesis are mostly dispensable. Nevertheless, bacteria usually do not feature the needed resistance against substrates or even products and capacity to produce precursors. Good knowledge of the metabolic network is thus essential, as metabolic engineering is often the only way of achieving the optimal strain. Unwished generation of by-products can thus be eliminated and substrate utilization can be optimized. Essential when applying metabolic engineering is an adequate organism with a well-known metabolism.

Efforts to produce rhamnolipids in a fermentation process have previously been reported (Trummler et al., Eur J Lipid Sci Technol (2003) 105, 536-571; Cha et al., Bioresour Technol (2008) 99, 7, 2192-2199; Ochsner et al., Appl. Environ. Microbiol. (1995) 61, 3503-3506; Müller et al., Applied Microbiological Biotechnology (2010) 87, 1, 167-174); Cabrera-Valladares et al., Applied Microbiological Biotechnology (2006) 73, 187-194 and Wang et al., Biotechnol Bioeng. (2007) 98, 4:842-53). These approaches have largely been aimed at the use of a non-pathogenic organism, and based on employing *Pseudomonas aeruginosa* or recombinant *Pseudomonas putida*, albeit production in genetically modified *Pseudomonas* is so far marginal. Further, yields have so far been unsatisfactorily and no attempts have been made in achieving control over the variety of rhamnolipids formed. For example, Ochsner et al., overexpressed rhlAB genes and obtained 0.6 g/l in *Pseudomona putida* KT2442 and suggested this strain to be particularly useful, since it accumulates 3-hydroxy fatty acids which may serve as precursors for poly(3-hydroxyalkanoates) and rhamnolipid synthesis. Furthermore, these authors suggest optimizing rhamnolipid synthesis by medium induction and bioprocess optimization in order to industrially apply such optimized strains. In sum, the carbon yield in Cmol rhamnolipid in relation to Cmol substrate, i.e., Cmol rhamnolipid/Cmol substrate achieved by Müller et al. when using *P. aeruginosa* PAO1 and sunflower oil as substrate is 0.07, by Trummler et al. using *Pseudomonas* sp. DSM2874 and oleic acid as substrate is 0.18, by Cha et al. using *P. putida* KCTC1067 and soybean oil as substrate is 0.17, by Ochsner et al. using *P. aeruginosa* PG201 and gylcerol as substrate is 0.17 or 0.09 when using *P. putida* KT2442 and glucose a substrate, by Wang et al. using *E. coli* TnERAB and glucose as a substrate is 0.07 and 0.06 when using *P. aeruginosa* PEER02 and glucose as a substrate.

The following table shows relevant carbon yield values (Cmol rhamnolipid/Cmol substrate and % of the theoretical maximum Cmol rhamnolipid/Cmol substrate). Note that when "oils" such as sunflower oil was used as carbon source, the theoretical maximum yield is given in relation to octanoate.

|  | Organism | Carbon Yield[1] [$Cmol_{rhamnolipid}$/$Cmol_{substrate}$] | % of theoretical maximum | Reference |
|---|---|---|---|---|
| Wildtypes | *P. aeruginosa* PAO1 | 0.07 | 7.6% | Müller et al. 2010b |
|  | *Pseudomonas* sp. DSM 2874 | 0.18 | 19.8% | Trummler et al. 2003 |

-continued

| | Organism | Carbon Yield[1] [Cmol$_{rhamnolipid}$/ Cmol$_{substrate}$] | % of theoretical maximum | Reference |
|---|---|---|---|---|
| Recombinants | P. putida KCTC 1067 | 0.17 | 17.9% | Cha et al. 2008 |
| | P. aeruginosa PEER02 | 0.04 | 4.4% | Wang et al. 2007 |
| | E. coli HB101 | 0.01 | 1.1% | Cabrera-Valladares et al. 2006a |
| | P. aeruginosa PG201 | 0.17 | 23.9% | Ochsner et al. 1995 |
| | E. coli TnERAB | 0.07 | 9.3% | Wang et al. 2007 |
| | P. aeruginosa PEER02 | 0.06 | 8.3% | Wang et al. 2007 |
| | P. putida KT2442 | 0.09 | 12.7% | Ochsner et al. 1995 |
| | E. coli W3110 | 0.04 | 5.1% | Cabrera-Valladares et al. 2006a |
| | E. coli TnERAB | 0.03 | 4.0% | Wang et al. 2007 |
| | P. fluorescens ATCC 15453 | 0.02 | 2.7% | Ochsner et al. 1995 |
| | E. coli DH5α | <0.01 | 0.7% | Ochsner et al. 1995 |
| | P. oleovorans GPo1 | 0.00 | 0.0% | Ochsner et al. 1995 |

However, none of these authors, apart from suggesting optimization of, for example, growth conditions or the carbon source; suggest other ways to optimize rhamnolipid production in a bacterial host. Indeed, in particular Ochsner et al., despite the use of the strong tac promoter which drives expression of the rhlAB operon did not achieve satisfying yields of rhamnolipids and suggested therefore either the optimization of growth conditions or the use of Pseudomona strains which produce large amounts of rhamnolipid precursors.

It is thus an object of the present invention to provide a method of producing rhamnolipids and an organism suitable for such a method that when used in rhamnolipid production overcomes at least one of the draw backs of the prior art. This object is solved by the method and the bacterial host cell according to the independent claims.

SUMMARY OF THE INVENTION

The present invention provides a genetically modified host cell that may be employed for production of rhamnolipids (RL) in high yields. This is achieved by expressing rhlA, rhlB and/or rhlC gene(s) that encode enzymes which are responsible for the production of rhamnolipids under the control of a heterologous promoter which, without being bound by theory, effects preferably such a gene expression level and, thus, increased level of the translation products (proteins) of the rhlA, rhlB and/or rhlC gene(s) that the host cell is capable to achieve a carbon yield of more than 0.18 Cmol rhamnolipid/Cmol substrate. The rhlA gene encodes the RhlA protein (3-hydroxyacyl-ACP O-3-hydroxyacyl-transferase), the rhlB gene encodes RhlB (rhamnosyltransferase I) and the rhlC gene encodes RhlC (rhamnosyltransferase II). A host cell according to the invention may thus be a recombinant cell, preferably a bacterial cell. Use of the modified host cell allows production of various rhamnolipids, e.g. mono- or dirhamnolipids.

In a first aspect the present invention provides a host cell, preferably a bacterial host cell. The bacterial host cell includes a rhlA gene or an ortholog thereof. The rhlA gene or the ortholog thereof is under the control of a heterologous promoter. The host cell also includes a rhlB gene or an ortholog thereof. The rhlB gene or the ortholog thereof is under the control of a heterologous promoter. The host cell is preferably capable of achieving a carbon yield of more than 0.18 Cmol rhamnolipid/Cmol substrate. This carbon yield coefficient has the advantage that the yield of C atoms comprised by a rhamnolipid is set in relation to the number of C atoms comprised by a substrate. Accordingly, comparability of the results can be ensured by choosing the unit Cmol, since it normalizes the rhamnolipid production rate to the amount of carbon atoms present in the carbon substrate. Indeed, different substrates, i.e., carbon sources have a different number of carbon atoms and, thus, for example, sun flower oil, soy bean oil or oleic acid that have more carbon atoms than, for example, glucose would result in a higher number of mole rhamnolipids. However, a carbon yield coefficient should allow the comparison between different substrates and host cells, for example, different bacteria such as Pseudomonas and Escherichia or bacterial species such as Pseudomonas aeruginosa and Pseudomonas putida. This is accomplished by the coefficient Cmol rhamnolipid/Cmol substrate.

The prior art did not achieve a carbon yield of more than 0.18 Cmol rhamnolipid/Cmol substrate. In particular, Ochsner et al. or Cabrera-Valladares et al. merely achieved 0.17 or only 0.01 and were not able to suggest a way to increase the carbon yield as was done by the present inventors. Rather, Ochsner et al. teach to modify culturing conditions or carbon sources, since these authors have already used a strong promoter. Hence, they did not think of or suggest an even stronger promoter. However, the present inventors thought of an even stronger promoter and were successful.

In a second aspect the present invention provides a method of producing a rhamnolipid. The method includes culturing a host cell according to the first aspect under conditions that allow rhamnolipid production. The method further includes recovering the rhamnolipid produced by the host cell. Optionally the method may include isolating the rhamnolipid.

In a related third aspect the present invention relates to the use of a host cell according to the first aspect for the production of rhamnolipids In a fourth aspect the present invention provides a rhamnolipid preparation that is obtainable by the method according to the second aspect. The preparation includes rhamnolipids that have more than 80% (w/w) fatty acids of a fatty acid selected from 3-hydroxy-n-octanoic acid, 3-hydroxy-n-decanoic acid, 3-hydroxy-n-decanoic acid, 3-hydroxy-n-dodecanoic acid, 3-hydroxy-n-tetradecanoic acid, 3-hydroxy-n-hexadecanoic acid and 3-hydroxy-n-octadecanoic acid.

In a fifth aspect the present invention provides a method of producing a rhamnolipid. The method includes culturing a host cell at a temperature above 30° C. The host cell includes a rhlA gene, or an ortholog thereof, and a rhlB gene, or an ortholog thereof. The host cell is cultured in a suitable medium. The method further includes allowing the host cell to produce the rhamnolipid. Also in said fifth aspect, the host cell may preferably also contain a rhlC gene, or an ortholog thereof.

BRIEF DESCRIPTION OF THE DRAWINGS

The invention will be better understood with reference to the detailed description when considered in conjunction with the non-limiting examples and the accompanying drawings.

FIG. 2 depicts toxicity studies with di-rhamnolipids using different bacteria: (a) Inhibitory effect of di-rhamnolipids on *E. coli*. Di-Rhamnolipid concentrations tested were 0 g/L (■), 5 g/L (▲), 10 g/L (♦), 25 g/L (□), 50 g/L (○), and 90 g/L (◊); (b) Inhibitory effect of di-rhamnolipids on *B. subtilis*. Di-Rhamnolipid concentrations tested were 0 mg/L (■), 2.5 mg/L (●), 5 mg/L (▲), 10 mg/L (♦), 25 mg/L (□), 50 mg/L (○), 75 mg/L (Δ), and 90 mg/L (◊); (c) Inhibitory effect of di-rhamnolipids on *C. glutamicum*. Di-Rhamnolipid concentrations tested were 0 mg/L (■), 2.5 mg/L (●), 5 mg/L (▲), 10 mg/L (♦), 25 mg/L (□), 50 mg/L (○), 75 mg/L (Δ), and 90 mg/L (◊); (d) Growth rates resulting from toxicity experiments with *B. subtilis* (■) and *C. glutamicum* (●); (e) growth rates in toxicity experiments with *E. coli*.

FIG. 8 depicts the uncoupling of rhamnolipid production and cell growth of *P. putida* in a 50 mL baffled flask. A: Fermentation characteristics including cell growth (■) and course of rhamnolipid (▲) and glucose (♦) concentrations and their respective fitted courses. CDW, cell dry weight; B: Specific rates resulting from the fitted experimental data. The black line represents the course of the growth rate, while the dashed line ( - - - ) and the dotted line (• • • •) show the specific glucose uptake rate and the specific rhamnolipid production rate, respectively.

FIG. 9 depicts the kinetics of rhamnolipid-production in *P. putida* in a stirred 3.2 L reactor. A: Development of biomass (■) and glucose (▲) concentration. The experimental data is depicted by symbols, while the lines present the fits using eq. (1) to (3). CDW, cell dry weight. B: Specific rates characterizing rhamnolipid production in *P. putida*. The solid line (——) shows the measured $^{13}CO_2$ production rate, originating from $^{13}$C-labeled glucose. The dashed line ( - - - ) shows the glucose uptake rate and was calculated on the basis of the aligned glucose concentration fit. The dotted line (• • • •) shows the expected amount of $CO_2$ produced from glucose, based on the calculated yield of 0.728 mol rhamnolipid/mol glucose.

The latest retention time of 20.11 min correlates with a molecular mass of 789.6 m/z and a di-rhamnolipid Rha-Rha-$C_{14}$-$C_{16}$ (or Rha-Rha-$C_{16}$-$C_{14}$).

Figures 13, 14A:
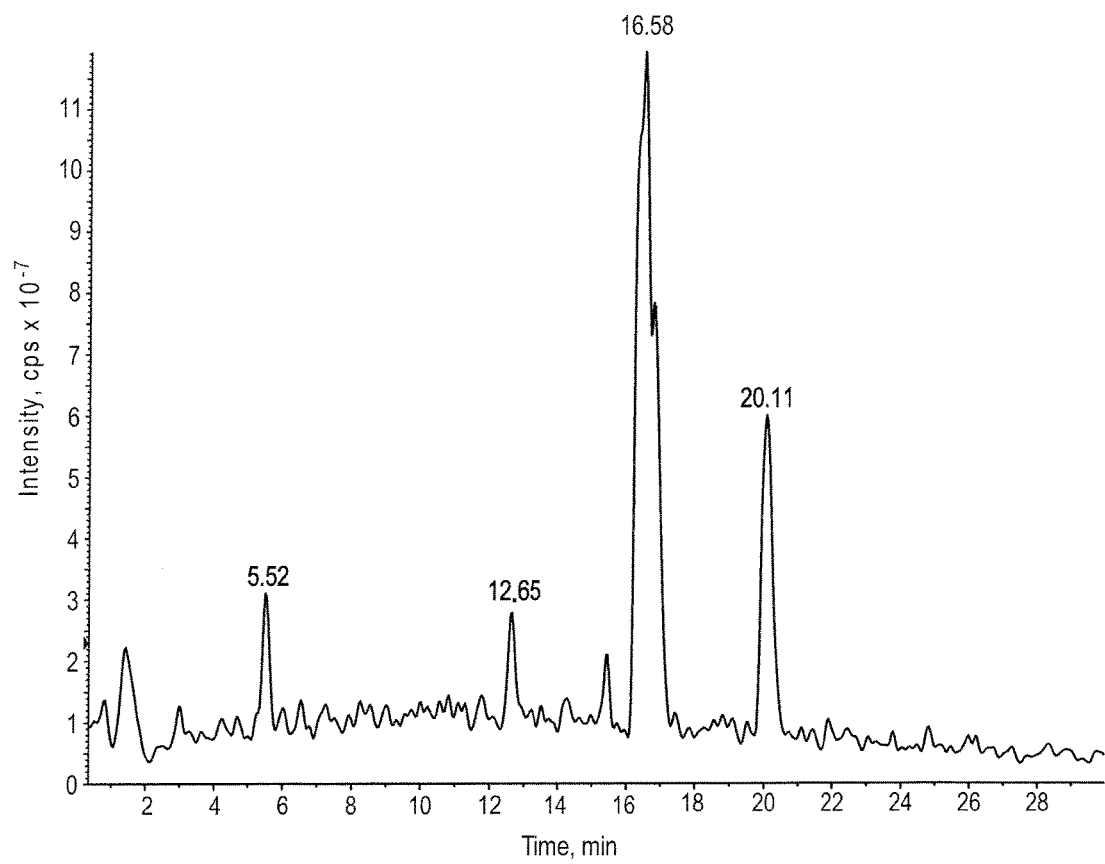

FIG. 13 depicts the minimal inhibitory concentration (MIC) of a rhamnolipid mixture produced by *B. glumae* against selected microorganisms. The Gram-positive bacteria are affected at particularly low levels, whereas the selected Gram-negative bacteria showed no inhibition of growth throughout the tested concentrations.

FIG. 14 shows averaged mass spectra of rhamnolipids of *B. glumae* PG1. The highest signal appears at a retention time of 16.58 min (A) indicating a molecular mass of 761.7 m/z (B), 12.65 min (A) accords to a molecular mass of 733.5 m/z (C) and 20.11 min (A) correlates with a molecular mass of 789.6 m/z (D).

Figure 15:
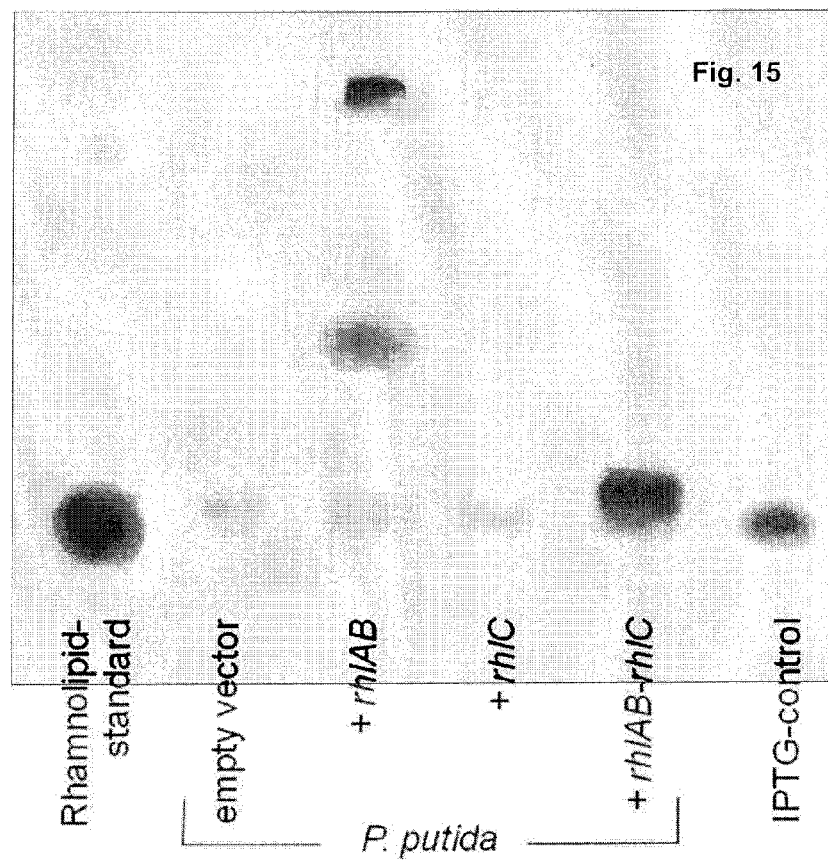

FIG. 15 shows analysis of recombinant rhamnolipid production in *P. putida* by thin-layer-chromatography. Rhamnolipids were extracted 24 hours after induction of gene expression by adding of IPTG. Heterologous expression of rhlAB genes from *B. glumae* resulted in mono-rhamnolipid production (lane 3), whereas expression of rhlAB and rhlC resulted in production of mainly di-rhamnolipid (lane 5). In contrast, there is no detectable amount of rhamnolipids when using the empty vector or when only rhlC was expressed (lanes 2 and 4). These rhamnolipids originating from *Burkholderia* contain longer fatty acid chains and can be analytically distinguished from rhamnolipids obtained from *P. aeruginosa* (lane 1) in TLC. Extraction of IPTG containing media (lane 6) was spotted to confirm the origin of violet spots in all *P. putida* samples (lanes 2-5). Extraction and thin-layer-chromatography were done threefold from independent cultures.

Figure 16:
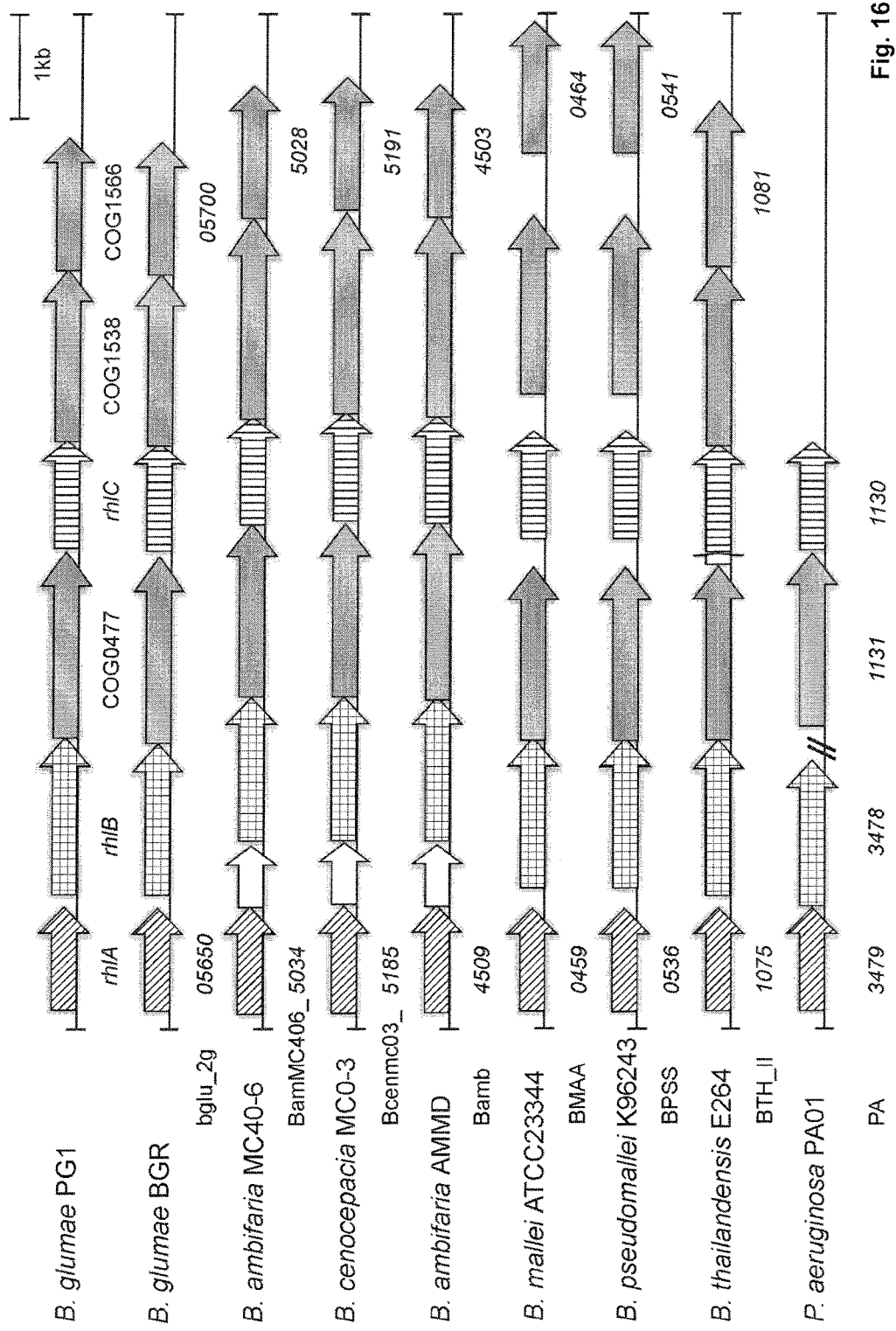

FIG. 16 depicts genetic organisation of rhlA, rhlB and rhlC in the genomes. The regions of different *Burkholderia* species are schematically shown, which contain the rhlA, rhlB and rhlC genes within a single gene cluster. In contrast thereto, in *P. aeruginosa* the rhlAB operon and the PA113'-rhlC operon are located at different regions of the chromosome. For *B. cenocepacia, B. mallei, B. pseudomallei* and *B. thailandensis* only one of two existing identical gene clusters is shown. Orthologous genes are symbolised in the same manner, neighbouring genes are shown in white. The genes are indicated by the locus Tag ID (e.g. Bamb) and the number of annotated genes. The nucleotide sequences obtained for the rhlA-C genes from *B. glumae* PG1 are deposited in the GenBank database under the accession numbers GU808765 (rhlA), GU808766 (rhlB) and GU808767 (rhlC), respectively.

Figure 17:
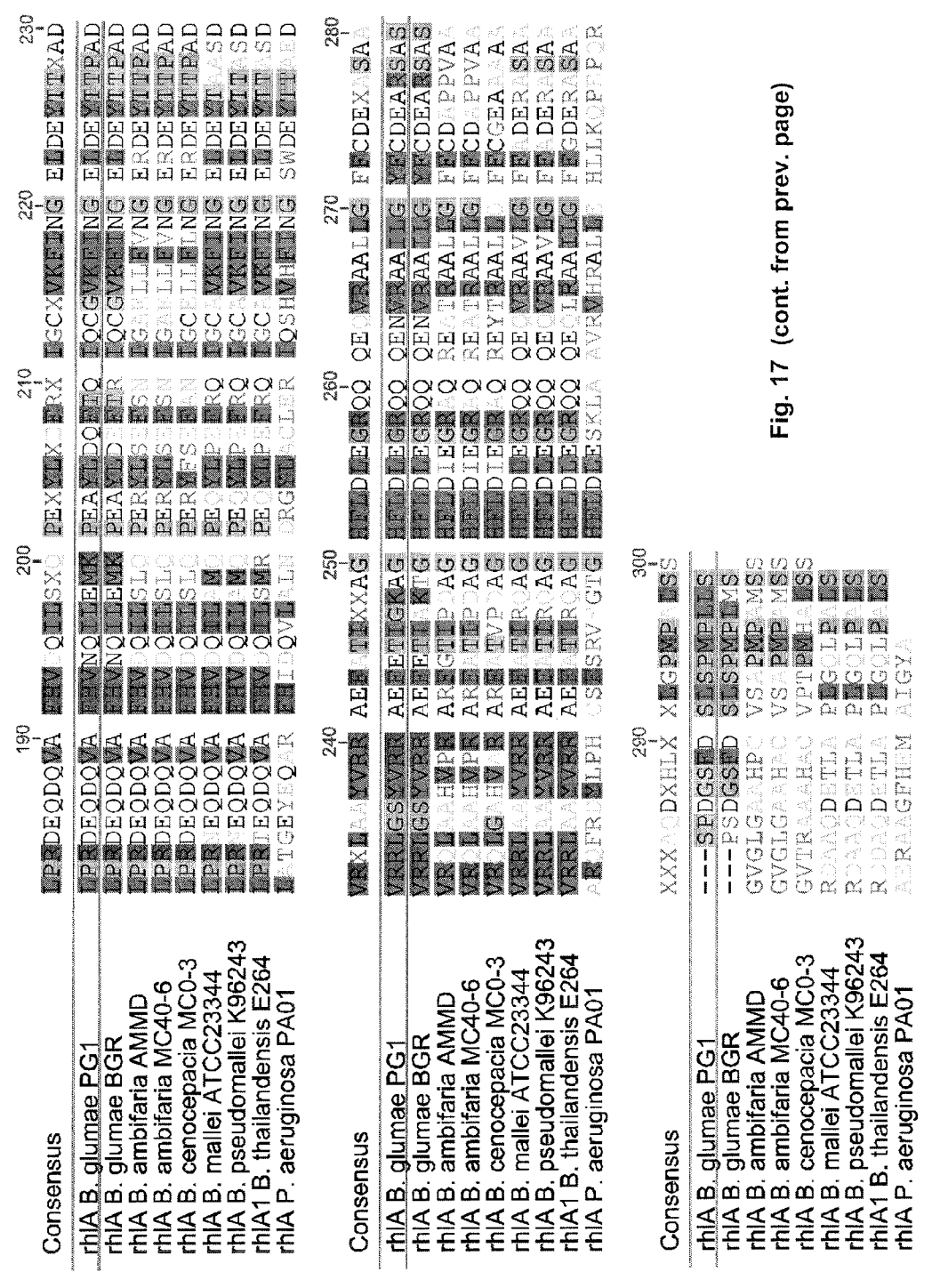

FIG. 17 depicts the alignment of protein sequences of RhlA homologous of eight different *Burkholderia* strains (SEQ ID NOs: 1-8), and *P. aeruginosa* (SEQ ID NO: 9). Different amino acids are depicted in grey. The homology of the RhlA is high within the *Burkholderia*-family, the comparison of amino acids between *B. glumae* and *P. aeruginosa* shows an identity of 45%.

FIG. 18 shows rhamnolipid production after 24 h of *P. putida* carrying a synthetic promoter library. *P. putida* with the empty promoter library vector ("0") and *P. putida* transformed with pVLT31 (plasmid with tac-promoter driven rhlA and rhlB genes) ("Ref.") as well as 22 *P. putida* strains having rhlA and B genes driven by synthetic promoters.

FIG. 19 depicts sequences of synthetic promoters that conferred high expression of rhlA and rhlB in a heterologous host (*P. putida*). The −35 and −10 sequences are highlighted in bold and larger letters. Also shown is a degenerate nucleotide sequence of a promoter sequence (SEQ ID NO:16). Each of the sequences shown in SEQ ID NO:17 (SynPro8), SEQ ID NO:18 (SynPro5), SEQ ID NO:19 (SynPro1) and SEQ ID NO:20 (SynPro11) is a preferred promoter sequence of the present invention that can preferably drive expression of a rhlA, rhlB and/or rhlC gene or of an ortholog thereof.

Figure 20:
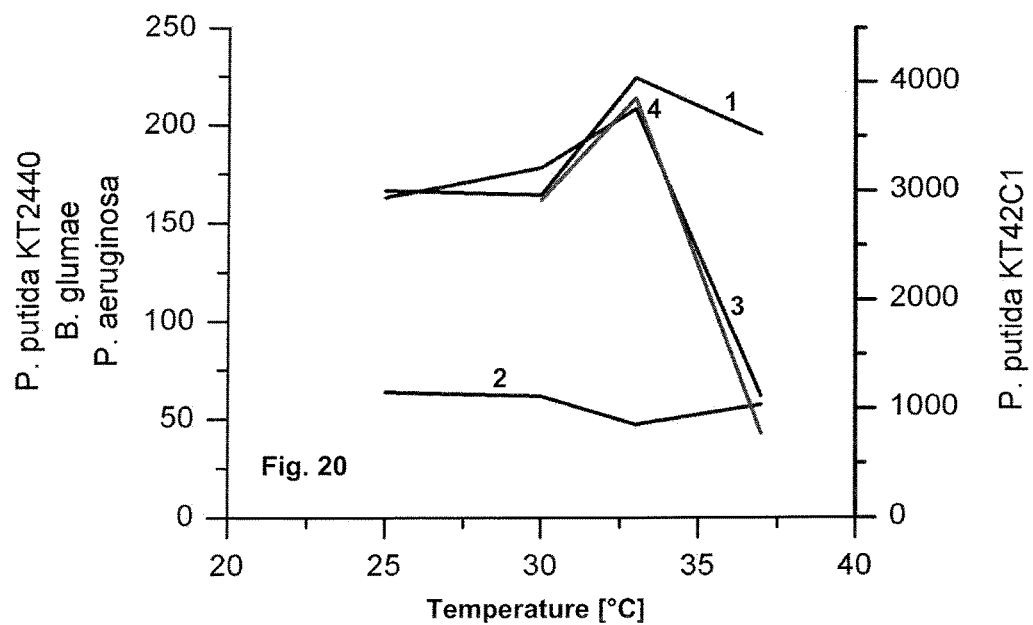

FIG. 20 shows the impact of the fermentation temperature on rhamnolipid production of *P. putida* KT2440 (1), *B. glumae* (2), *P. aeruginosa* (3), and *P. putida* KT42C1 (4).

Figure 21:
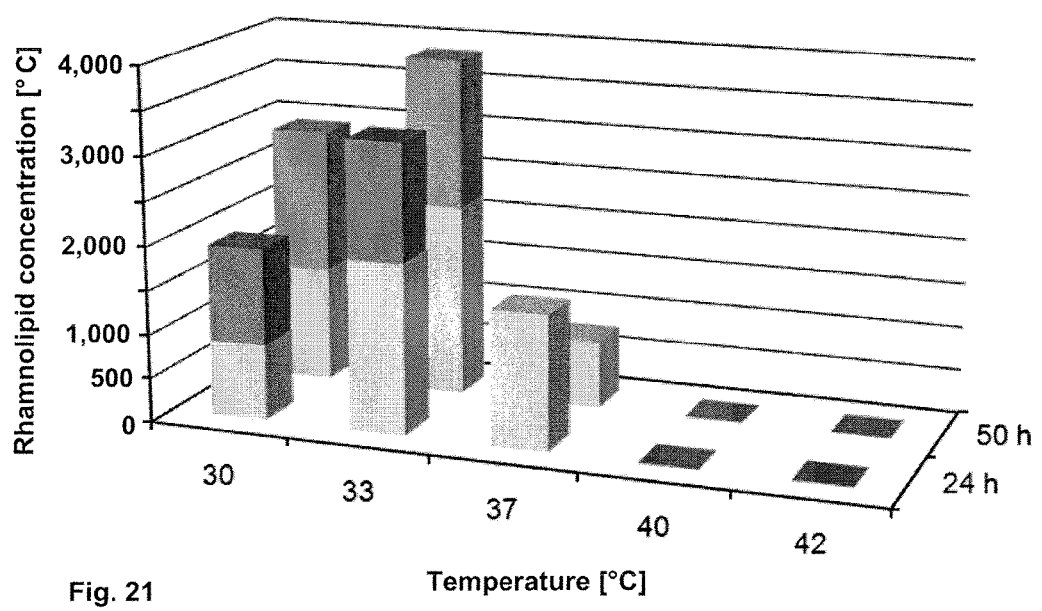

FIG. 21 depicts the quantification of alternate product formed by *P. putida* KT2440 at the indicated temperatures. The concentrations of the products after 24 h and 50 h in the temperature dependent experiments are presented. While the concentrations of the mono-rhamnolipid are presented in the light colors, the dark colors present the concentrations of the differing product, the duplicate cultures provided.

DETAILED DESCRIPTION OF THE INVENTION

The present inventors have found that uncoupling rhamnolipid production, which is mainly governed by the rhlAA and rhlB genes, from its natural regulation including quorum sensing and expressing said genes under the control of a strong heterologous promoter increases rhamnolipid production in a bacterial host cell. This finding is unexpected. Choi et al., Journal of Biotechnology (2001), 151, 30-42 teach that quorum sensing is important for rhamnolipid production. However, Ochsner et al., loc. cit., have overexpressed rhlA and rhlB by using the tac promoter (thereby uncoupling the quorum sensing regulation) and have not observed the yield that the present inventors have observed. Accordingly, these authors teach that medium induction and bioprocess optimization should be undertaken to obtain higher biosurfactant productivities with strains which can be industrially applied. However, Ochsner et al. do not suggest applying a stronger promoter than the tac promoter in order to increase rhlA and rhlB expression and, thus, rhamnolipid production. This is so because, the T7 promoter provides an excess of transcripts and thus a further increase of transcripts, if possible at all, would probably not help. Moreover, Ochnser et al. teaches that the strain they used would be beneficial for rhamnolipid production in that it accumulates 3-hydroxy fatty acids which may serve as precursore for poly(3-hydroxyalkanoates) (PHA) and rhamnolipid synthesis. However, in contrast, the present inventors found that removing PHA formation as competing pathway to rhamnolipid production is indeed beneficial, since such strains show an even more enhanced rhamnolipid production.

As indicated above, in the context of the invention a "rhamnolipid" refers to a glycolipid that has a lipid portion that includes one or more, typically linear, saturated or unsaturated β-hydroxy-carboxylic acid moieties and a saccharide portion of one or more units of rhamnose or an ester thereof. The saccharide portion and the lipid portion are linked via an O-glycosidic bond between the 1-OH group of a rhamnose-moiety of the saccharide portion and the 3-OH group of a β-hydroxy-carboxylic acid of the lipid portion. Thus the carboxylic group of one carboxylic acid moiety defines the end of the rhamnolipid. This carboxylic group may be either a free carboxylic group or it may define an ester with an aliphatic alcohol. Where more than one rhamnose-moiety is included in a rhamnolipid, each of the rhamnose moieties not linked to the lipid portion is linked to another rhamnose moiety via an 1,2-glycosidic bond. Thus the 3-OH group of a rhamnose-moiety can be taken to define an end of the rhamnolipid. This hydroxy group may be either a free hydroxy group or it may define an ester with an aliphatic carboxylic acid. In embodiments where two or more β-hydroxy-carboxylic acids are present in a rhamnolipid, the β-hydroxy-carboxylic acid moieties are selected independently from each other. β-hydroxy-carboxylic acid moieties of a respective plurality of β-hydroxy-carboxylic acid moieties may be in some embodiments be identical. In some embodiments they are different from each other.

Generally a rhamnolipid can be represented by the following formula (I).

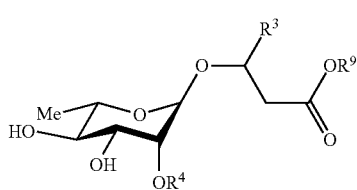

(I)

In this formula $R^9$ is a hydrogen atom (H) or an aliphatic group that has a main chain of one to about 46, such as one to about 42, one to about 40, one to about 38, one to about 36, one to about 34, one to about 30, one to about 28, including e.g. 2, 3, 4, 5, 6, 7, 8, 9, 10, 11, 12, 13, 14, 15, 16, 17, 18, 19, 20, 21, 22, 23, 24, 25, 26, 27 or 28 carbon atoms and one to about three, including two, oxygen atoms. In some embodiments the main chain of the respective aliphatic group carries a terminal carboxylic acid group and/or an internal ester group. As an illustrative example in this regard, $R^9$ may be of the formula —CH($R^5$)—CH$_2$—COOR$^6$, including of the formula —CH($R^5$)—CH$_2$—COO—CH($R^7$)—CH$_2$—COOR$^8$. In these illustrative moieties, $R^5$ may be an aliphatic moiety with a main chain that has a length from 1 to about 19, such as from 1 to about 17, from 1 to about 15, from 1 to about 13, about 2 to about 13, about 3 to about 13 or about 4 to about 13, including e.g. 2, 3, 4, 5, 6, 7, 8, 9, 10, 11 or 12 carbon atoms. $R^6$ and $R^8$ are independent from one another a hydrogen atom (H) or an aliphatic group that has a main chain of one to about five, such as 2, 3 or 4 carbon atoms. $R^7$ is a hydrogen atom (H) or an aliphatic group that has a main chain of one to about 19 carbon atoms, such as two to about 19 or three to about 19, e.g. 3, 4, 5, 6, 7, 8, 9, 10, 11, 12, 13, 14, 15, 16, 17 or 18 carbon atoms.

The term "aliphatic" means, unless otherwise stated, a straight or branched hydrocarbon chain, which may be saturated or mono- or poly-unsaturated and include heteroatoms. The term "heteroatom" as used herein means an atom of any element other than carbon or hydrogen. An unsaturated aliphatic group contains one or more double and/or triple bonds (alkenyl or alkinyl moieties). The branches of the hydrocarbon chain may include linear chains as well as non-aromatic cyclic elements. The hydrocarbon chain, which may, unless otherwise stated, be of any length, and contain any number of branches. Typically, the hydrocarbon (main) chain includes 1 to 5, to 10, to 15 or to 20 carbon atoms. Examples of alkenyl radicals are straight-chain or branched hydrocarbon radicals which contain one or more double bonds. Alkenyl radicals generally contain about two to about twenty carbon atoms and one or more, for instance two, double bonds, such as about two to about ten carbon atoms, and one double bond. Alkynyl radicals normally contain about two to about twenty carbon atoms and one or more, for example two, triple bonds, such as two to ten carbon atoms, and one triple bond. Examples of alkynyl radicals are straight-chain or branched hydrocarbon radicals which contain one or more triple bonds. Examples of alkyl groups are methyl, ethyl, propyl, butyl, pentyl, hexyl, heptyl, octyl, nonyl, decyl, the n isomers of these radicals, isopropyl, isobutyl, isopentyl, sec-butyl, tert-butyl, neopentyl, 3,3-dimethylbutyl. Both the main chain as well as the branches may furthermore contain heteroatoms as for instance N, O, S, Se or Si or a carbon atom may be replaced by one of these heteroatoms. An aliphatic moiety may be substituted or unsubstituted with one or more functional groups. Substituents may be any functional group, as for example, but not limited to, amino, amido, carbonyl, carboxyl, hydroxyl, nitro, thio and sulfonyl.

$R^4$ in formula (I) is a hydrogen atom (H), a substituted or unsubstituted rhamnopyranosyl moiety, or an aliphatic group having a main chain of one to about 12, such as 2, 3, 4, 5, 6, 7, 8, 9, 10 or 11 carbon atoms that may be saturated or unsaturated or an acyl group —C(O)$R^{10}$, wherein $R^{10}$ is a hydrogen atom (H) an aliphatic group having a main chain of one to about 11, such as 2, 3, 4, 5, 6, 7, 8, 9 or 10 carbon atoms. A respective aliphatic group of $R^2$ may include a keto group at the α-position. In the above formulae n is an integer selected in the range from 1 to about 17, such as from 1 to about 15, from 1 to about 13, about 2 to about 13, about 3 to about 13 or about 4 to about 13, including e.g. 2, 3, 4, 5, 6, 7, 8, 9, 10, 11 or 12. β-hydroxy-carboxylic acid moieties of a respective plurality of β-hydroxy-carboxylic acid moieties may be identical or different. Where $R^4$ is a substituted rhamnopyranosyl moiety, it is typically substituted at the hydroxyl group at the 2 position in the form of an ester group or an ether group replacing the hydroxyl group. A respective ester group may include an aliphatic moiety with a main chain of one to about 11, such as 2, 3, 4, 5, 6, 7, 8, 9 or 10 carbon atoms. A corresponding ether group may be a further substituted or unsubstituted rhamnopyranosyl moiety or include an aliphatic group that has a main chain of one to about 12, such as 2, 3, 4, 5, 6, 7, 8, 9, 10 or 11 carbon atoms that may be saturated or unsaturated.

$R^3$ in the above formula (I) is an aliphatic group having a main chain of about 3 to about 19, such as 4, 5, 6, 7, 8, 9, 10, 11, 12, 13, 14, 15, 16, 17 or 18 carbon atoms.

In typical embodiments where a rhamnolipid includes only saturated β-hydroxy-carboxylic acid moieties a respective rhamnolipid can be represented by one of the following general formulae (II), (III), (IV), (V) or (VI):

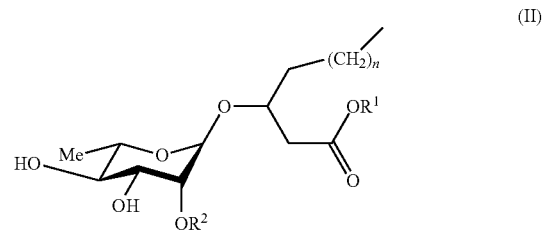

(II)

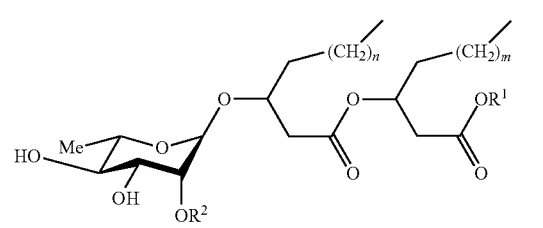

(III)

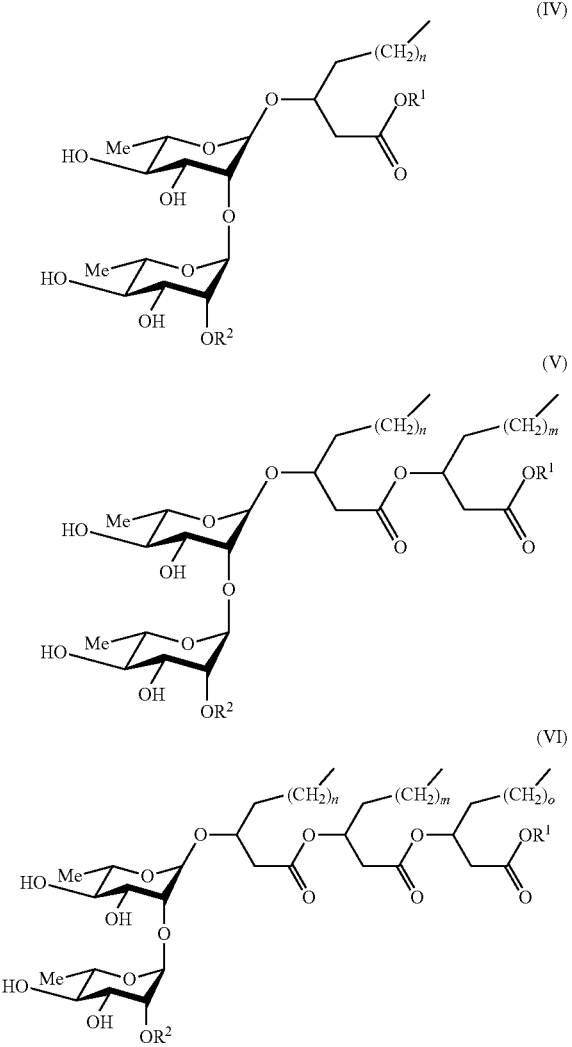

R[1] in the above formulae is a hydrogen atom (H) or an aliphatic group having a main chain of one to about five, such as 2, 3 or 4 carbon atoms. R[2] in the above formulae is a hydrogen atom (H), an aliphatic group having a main chain of one to about 12, such as 2, 3, 4, 5, 6, 7, 8, 9, 10 or 11 carbon atoms that may be saturated or unsaturated or an acyl group —C(O)R[3], wherein R[10] is a hydrogen atom (H) an aliphatic group having a main chain of one to about 11, such as 2, 3, 4, 5, 6, 7, 8, 9 or 10 carbon atoms. A respective aliphatic group of R[2] may include a keto group at the α-position. In the above formulae n is an integer selected in the range from 1 to about 17, such as from 1 to about 15, from 1 to about 13, about 2 to about 13, about 3 to about 13 or about 4 to about 13, including e.g. 2, 3, 4, 5, 6, 7, 8, 9, 10, 11 or 12. Likewise in formulae (III), (V), and (VI) m is an integer selected in the range from 1 to about 17, such as from 1 to about 15, from 1 to about 13, about 2 to about 13, about 3 to about 13 or about 4 to about 13, including e.g. 2, 3, 4, 5, 6, 7, 8, 9, 10, 11 or 12. In formula (VI) o is an integer selected in the range from 1 to about 17, such as from 1 to about 15, from 1 to about 13, about 2 to about 13, about 3 to about 13 or about 4 to about 13, including e.g. 2, 3, 4, 5, 6, 7, 8, 9, 10, 11 or 12.

In embodiments where a rhamnolipid includes one or more unsaturated β-hydroxy-carboxylic acid moieties a respective rhamnolipid may resemble the above formulas, however, include one or more unsaturated carboxylic acid moieties instead of the saturated carboxylic acid moieties depicted above. Such a rhamnolipid may for instance include a 3-hydroxy-n-octenoic acid moiety, a 3-hydroxy-n-octadienoic acid moiety, a 3-hydroxy-n-decenoic acid moiety, a 3-hydroxy-n-dodecenoic acid moiety, a 3-hydroxy-n-dodecadienoic acid moiety, a 3-hydroxy-n-tetradecenoic acid moiety or a 3-hydroxy-n-tetradecadienoic acid moiety (e.g. Abdel-Mawgoud, et al., 2010, supra; Arutchelvi, J., & Doble, M., J. Letters in Applied Microbiology (2010) 51, 75-82; Sharma, A., et al., J. Nat. Prod. (2007) 70, 941-947).

A rhamnolipid is soluble in both polar and non-polar fluids and is thus an amphiphilic compound. The amphiphilic properties of a rhamnolipid are due to the presence of both polar and non-polar moieties, i.e. hydroxy- and carboxy groups as well as a hydrocarbon chain that does not carry a functional group, within the same molecule. In this regard a rhamnolipid is generally of surfactant nature. Using neutron scattering techniques of SANS and NR, Chen et al. (Langmuir (2010) 26, 23, 18281-18292) have studied solution self-assembly and adsorption at the air-water interface of rhamnolipids. In dilute solutions of less than 20 mM the rhamnolipids analysed formed small globular micelles, while at higher concentrations, the monorhamnolipid examined formed unilamellar or bilamellar vesicles.

The rhamnolipid may have a net charge at physiological pH. The term "physiological pH" is known to those in the art to refer to the pH value of blood, which has typically a pH value of about 7.4. In embodiments where the rhamnolipid has a free terminal carboxylic acid group the rhamnolipid may have a negative net charge of −1 at physiological pH. In embodiments where the rhamnolipid has a terminal ester group the rhamnolipid may be of neutral net charge and may thus be defined as having no net charge at physiological pH.

Rhamnolipids are a group of glycolipids with biosurfactant activity. Glycolipids such as rhamnolipids, trehalosolipids or sophorolipids are biosurfactants of low molecular weight. They can be contrasted to lipopeptides such as surfactin, strepofactin, polymyxin or gramicidin, which include polymers of high molecular weight, e.g. polysaccharides or lipopolysaccharides. As for rhamnolipids, depending on the particular combination of the lipid portion and the saccharide portion there are various glycolipids with differing polarity. It is known that for example various strains of *Pseudomonas* are capable of extracellular secretion of rhamnolipids, when growing on soluble and insoluble carbon sources. Rhamnolipids have initially been known to be produced by bacteria of the genus *Pseudomonas*; with most reports focusing on strains of the opportunistic pathogen *P. aeruginosa*. Rhamnolipids are the main constituents of a biosurfactant produced by *P. aeruginosa*. A surface motility of this microorganism termed "swarming", a collective behaviour, is based on the action of the rhamnolipids, where they function as a wetting agent, reducing surface tension. Rhamnolipids also act as virulence factors and play a role in shielding of bacteria such as *P. aeruginosa* cells from the host defense.

Rhamnolipids produced by the host cells of the present invention can be used as detergents in washing agents, cas emulsifiers in the cosmetic and food industry or for the treatment of bacterial and/or fungal infections of mammals, in particular humans and/or plants.

Rhamnolipids produced by the host cell of the present invention may be subject to modifications by enzymes that are capable to modify rhamnolipids, such as lipases and/or esterases. In particular, enzymes that are capable to modify rhamnolipids are preferably used to modify rhamnolipids after they have been synthesized. More particularly, these enzymes can trim rhamnolipids such that one or more lipids are cut off and/or ester linkages are broken up in order to modify the rhamnolipid as is desired.

A host cell of the present invention includes any suitable host cell that is capable of producing rhamnolipids. Accordingly, the present invention envisages as a host cell preferably non-pathogenic host cells (non-pathogenic for humans) including a unicellular host cell such as a fungal host cell, for example, a yeast. Preferably, however, the host cell of the present invention is a bacterial host cell including non-pathogenic bacterial host cells such as bacterial host cells capable of producing rhamnolipids.

A bacterial host cell according to the invention includes a rhlA gene or an ortholog thereof. The rhlA gene or the respective ortholog is under the control of a heterologous promoter. In some embodiments the rhlA gene is an endogenous gene of the bacterial host cell. In some embodiments the rhlA gene is a heterologous gene. In some embodiments the rhlA gene or the respective ortholog is under the control of a promoter that is different from the promoter that controls the rhlB gene. In some embodiments the rhlA gene or the respective ortholog is under the control of a promoter that is similar or identical to the promoter that controls the rhlB gene. Likewise, the rhlB gene or the respective ortholog is under the control of a heterologous promoter. In some embodiments the rhlB gene is an endogenous gene of the bacterial host cell. In some embodiments the rhlB gene is a heterologous gene. Where present, the rhlC gene or the respective ortholog may in some embodiments be under the control of a heterologous promoter. In some embodiments the rhlC gene is an endogenous gene of the bacterial host cell. In some embodiments the rhlC gene is a heterologous gene. As should be apparent from the above, each of the promoters that controls the rhlB gene, the rhlB gene and in some embodiments the promoters that control the rhlC gene are selected independently from both the gene the respective promoter controls and from any other heterologous promoter that controls a gene of a Rhamnosyltransferase peptide or protein.

An ortholog of rhlA encodes a protein having 3-hydroxyacyl-ACP O-3-hydroxyacyltransferase activity, an ortholog of rhlB a protein having rhamnosyltransferase I activity and an ortholog of rhlC gene encodes a protein having rhamnosyltransferase II activity. These activities are well known in the art and are explained in WO 2012/013554 on pages 4 and 5. Similarly, an otholog of RhlA, RhlB or RhlC has 3-hydroxyacyl-ACP O-3-hydroxyacyltransferase activity, rhamnosyltransferase I activity, and rhamnosyltransferase II activity, respectively.

A wide variety of transcriptional and translational regulatory sequences may be employed, depending upon the nature of the host, as long as a desired yield of rhamnolipid(s) is obtained. The transcriptional and translational regulatory signals may be derived from viral sources, such as adenovirus, bovine papilloma virus, cytomegalovirus or simian virus, where the regulatory signals are associated with a particular gene sequence which has a high level of expression. Alternatively, promoters from mammalian expression products, such as actin, collagen and myosin may be employed. Transcriptional initiation regulatory signals may be selected which allow for repression or activation, so that expression of the gene sequences can be modulated. Of interest may in some embodiments also be regulatory signals which are temperature-sensitive so that by varying the temperature, expression can be repressed or initiated, or are subject to chemical (such as metabolite) regulation.

A nucleic acid molecule encoding a rhamnolipid and an operably linked promoter may be introduced into a recipient prokaryotic cell either as a nonreplicating DNA or RNA molecule, which may be a linear molecule or a closed covalent circular molecule. Since such molecules are incapable of autonomous replication, the expression of the gene may occur through the transient expression of the introduced sequence. Alternatively, permanent expression may occur through the integration of the introduced DNA sequence into the host chromosome.

A vector may be employed which is capable of integrating the desired gene sequences into the host cell chromosome. Cells which have stably integrated the introduced DNA into their chromosomes can be selected by also introducing one or more markers which allow for selection of host cells which contain the expression vector. The marker may provide for prototrophy to an auxotrophic host, biocide resistance, e.g., antibiotics, or heavy metals, such as copper, or the like. The selectable marker gene sequence can either be directly linked to the DNA gene sequences to be expressed, or introduced into the same cell by co-transfection. Additional elements may also be needed for optimal synthesis of mRNA. These elements may include splice signals, as well as transcription promoters, enhancers, and termination signals.

The introduced nucleic acid molecule can be incorporated into a plasmid or viral vector capable of autonomous replication in the recipient host. Any of a wide variety of vectors may be employed for this purpose. Factors of importance in selecting a particular plasmid or viral vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species.

An illustrative example of a prokaryotic vector is a plasmid, such as a plasmid capable of replication in *E. coli* (such as, for example, pBR322, ColEl, pSC101, pACYC 184, VX). *Bacillus* plasmids include pC194, pC221, pT127, and the like. Suitable *Streptomyces* plasmids include p1J101 (Kendall et al., J. Bacteriol. (1987) 169, 4177-4183), and *streptomyces* bacteriophages such as C31. *Pseudomonas* plasmids are for instance reviewed by John et al. (Rev. Infect. Dis. 8:693-704, 1986).

Once the vector or nucleic acid molecule that contains the construct(s) has been prepared for expression, the DNA construct(s) may be introduced into the host cell by any of a variety of suitable means, i.e., transformation, transfection, conjugation, protoplast fusion, electroporation, particle gun technology, calcium phosphate-precipitation, direct microinjection, and the like. After the introduction of the vector, recipient cells are grown in a selective medium, which selects for the growth of vector-containing cells. Expression of the cloned gene(s) results in the production of a kinase of the invention, or fragments thereof. This can take place in the transformed cells as such, or following the induction of these cells to differentiate. A variety of incubation conditions can be used to form the peptide of the present invention. It may be desired to use conditions that mimic physiological conditions.

The terms "expression" and "expressed", as used herein, are used in their broadest meaning, to signify that a sequence included in a nucleic acid molecule and encoding a peptide/protein is converted into its peptide/protein product. Thus, where the nucleic acid is DNA, expression refers to the transcription of a sequence of the DNA into RNA and the translation of the RNA into protein. Where the nucleic acid is RNA, expression may include the replication of this RNA into further RNA copies and/or the reverse transcription of the RNA into DNA and optionally the transcription of this DNA into further RNA molecule(s). In any case expression of RNA includes the translation of any of the RNA species provided/produced into protein. Hence, expression is performed by translation and includes one or more processes selected from the group consisting of transcription, reverse transcription and replication. Expression of the protein or peptide of the member of the plurality of peptides and/or proteins may be carried out using an in vitro expression system. Such an expression system may include a cell extract, typically from bacteria, rabbit reticulocytes or wheat germ. Many suitable systems are commercially available. The mixture of amino acids used may include synthetic amino acids if desired, to increase the possible number or variety of proteins produced in the library. This can be accomplished by charging tRNAs with artificial amino acids and using these tRNAs for the in vitro translation of the proteins to be selected. A nucleic acid molecule, such as DNA, is said to be "capable of expressing" a peptide/protein if it contains nucleotide sequences which contain transcriptional and translational regulatory information and such sequences are operably linked to nucleotide sequences which encode the polypeptide. A suitable embodiment for expression purposes is the use of a vector, in particular an expression vector. Thus, the present invention also provides a host cell transformed/transfected with an expression vector.

An expression vector, which may include one or more regulatory sequences and be capable of directing the expression of nucleic acids to which it is operably linked. An operable linkage is a linkage in which a coding nucleotide sequence of interest is linked to one or more regulatory sequence(s) such that expression of the nucleotide sequence sought to be expressed can be allowed. Thus, a regulatory sequence operably linked to a coding sequence is capable of effecting the expression of the coding sequence, for instance in an in vitro transcription/translation system or in a cell when the vector is introduced into the cell. A respective regulatory sequence need not be contiguous with the coding sequence, as long as it functions to direct the expression thereof. Thus, for example, intervening untranslated yet transcribed sequences may be present between a promoter sequence and the coding sequence and the promoter sequence can still be considered "operably linked" to the coding sequence.

The term "regulatory sequence" includes controllable transcriptional promoters, operators, enhancers, silencers, transcriptional terminators, 5' and 3' untranslated regions which interact with host cellular proteins to carry out transcription and translation and other elements that may control gene expression including initiation and termination codons. The regulatory sequences can be native (homologous), or can be foreign (heterologous) to the cell and/or the nucleotide sequence that is used. The precise nature of the regulatory sequences needed for gene sequence expression may vary from organism to organism, but shall in general include a promoter region which, in prokaryotes, contains both the promoter (which directs the initiation of RNA transcription) as well as the DNA sequences which, when transcribed into RNA, will signal synthesis initiation. Such regions will normally include those 5'-non-coding sequences involved with initiation of transcription and translation, such as the TATA box, capping sequence or CAAT sequence. These regulatory sequences are generally individually selected for a certain embodiment, for example for a certain cell to be used. The skilled artisan will be aware that proper expression in a prokaryotic cell also requires the presence of a ribosome-binding site upstream of the gene sequence-encoding sequence.

The term "transfecting" defines a number of methods to insert a nucleic acid vector or other nucleic acid molecules into a cellular organism. These methods involve a variety of techniques, such as treating the cells with high concentrations of salt, an electric field, detergent, or DMSO to render the outer membrane or wall of the cells permeable to nucleic acid molecules of interest or use of various viral transduction strategies.

The terms "rhlA gene" and "rhlB gene", as well as the term "rhlC gene", include variants. The term "variant" or "altered" in reference to a nucleic acid or polypeptide refers to polymorphisms, i.e. the exchange, deletion, or insertion of one or more nucleotides or amino acids, respectively, compared to the predominant form of the respective nucleic acid or polypeptide. A variant may be a polypeptide that includes a germline alteration. Such an alteration may be a deletion, insertion or substitution of one or more amino acids, and may include single nucleotide polymorphisms (SNPs). In the context of the present invention, a variant in some embodiments refers to a contiguous sequence of at least about 50, such as about 100, about 200, or about 300 amino acids set forth in the amino acid sequence of a protein named herein (cf. e.g. below), or the corresponding full-length amino acid sequence, with the proviso that said alteration is included in the respective amino acid sequence. In case the mutation leads to a premature stop codon in the nucleotide sequence encoding the protein, the sequence may even be shorter than the corresponding wild type protein. As a rough guidance, subunit A of rhamnosyltransferase I typically has an amino acid sequence with a length of about 200 to about 400, such as about 250 to about 350 amino acids, subunit B of rhamnosyltransferase I typically has an amino acid sequence with a length of about 350 to about 550 such as about 400 to about 500 amino acids, while rhamnosyltransferase II typically has an amino acid sequence with a length of about 100 to about 400, such as about 150 to about 350 amino acids. The rhamnosyltransferase polypeptide can be encoded by a full-length nucleic acid sequence, i.e. the complete coding sequence of the respective gene, or any portion of the full-length nucleic acid sequence, as long as the alteration of the polypeptide is retained.

The amino acid sequence of a variant is substantially similar to a known Rhamnosyltransferase sequence such as a sequence referred to below. A sequence that is substantially similar to rhamnosyltransferase will in some embodiments have at least about 65%, at least about 65%, the amino acid sequence of a variant is substantially similar to a sequence referred to below. A sequence that is substantially similar to rhamnosyltransferase will in some embodiments have at least 60%, at least 70%, at least 80%, such as at least 90% identity, including at least 95%, at least 97%, at least 98%, at least 99%, or at least 99.5% identity to the sequence of a known rhamnosyltransferase, with the proviso that the altered position or sequence is retained.

By "identity" is meant a property of sequences that measures their similarity or relationship. Identity is measured by dividing the number of identical residues by the total number of residues and gaps and multiplying the product by 100. Preferably, identity is determined over the entire length of the sequences being compared. "Gaps" are spaces in an alignment that are the result of additions or deletions of amino acids. Thus, two copies of exactly the same sequence have 100% identity, but sequences that are less highly conserved, and have deletions, additions, or replacements, may have a lower degree of identity. Those skilled in the art will recognize that several computer programs are available for determining sequence identity using standard parameters, for example Blast (Altschul, et al. (1997) Nucleic Acids Res. 25:3389-3402), Blast2 (Altschul, et al. (1990) J. Mol. Biol. 215:403-410), and Smith-Waterman (Smith, et al. (1981) J. Mol. Biol. 147:195-197). The term "mutated" or "mutant" in reference to a nucleic acid or a polypeptide refers to the exchange, deletion, or insertion of one or more nucleotides or amino acids, respectively, compared to the naturally occurring nucleic acid or polypeptide. The term "altered" or "variant" in reference to a nucleic acid or polypeptide refers to polymorphisms, i.e. the exchange, deletion, or insertion of one or more nucleotides or amino acids, respectively, compared to the predominant form of the respective nucleic acid or polypeptide.

The term "position" when used in accordance with the disclosure means the position of either an amino acid within an amino acid sequence depicted herein or the position of a nucleotide within a nucleic acid sequence depicted herein. The term "corresponding" as used herein also includes that a position is not only determined by the number of the preceding nucleotides/amino acids, but is rather to be viewed in the context of the circumjacent portion of the sequence. Accordingly, the position of a given amino acid in accordance with the disclosure which may be substituted may very due to deletion or addition of amino acids elsewhere in a (mutant or wild-type) virus. In this regard it is also noted that data base entries on a nucleic acid sequence of a Rhamnosyltransferase may vary in their coverage of non-translated regions, thereby identifying different nucleic acid positions, even though the length of the coding region is unchanged/the same. Similarly, the position of a given nucleotide in accordance with the present disclosure which may be substituted may vary due to deletions or additional nucleotides elsewhere in a non-translated region of a virus, including the promoter and/or any other regulatory sequences or gene (including exons and introns).

Thus, when a position is referred to as a "corresponding position" in accordance with the disclosure it is understood that nucleotides/amino acids may differ in terms of the specified numeral but may still have similar neighbouring nucleotides/amino acids. Such nucleotides/amino acids which may be exchanged, deleted or added are also included in the term "corresponding position".

Specifically, in order to determine whether an amino acid residue of the amino acid sequence of a Rhamnosyltransferase different from a known strain corresponds to a certain position in the amino acid sequence of the known strain, a skilled artisan can use means and methods well-known in the art, e.g., alignments, either manually or by using computer programs such as BLAST2.0, which stands for Basic Local Alignment Search Tool or ClustalW or any other suitable program which is suitable to generate sequence alignments. Accordingly, a known wild-type virus strain may serve as "subject sequence" or "reference sequence", while the amino acid sequence or nucleic acid sequence of a virus different from the wild-type virus strain described herein can serve as "query sequence". The terms "reference sequence" and "wild type sequence" are used interchangeably herein.

In general, the term "fragment", as used herein with respect to an Influenza virus according to the disclosure, relates to shortened nucleic acid or amino acid sequences that correspond to a certain Influenza virus but lack a portion thereof. They may for example be an N-terminally and/or C-terminally shortened sequence, of which a nucleic acid sequence retains the capability of being expressed and of which an amino acid sequence retains the capability of being recognized and/or bound by an immunoglobulin in a mammalian or avian body.

A bacterial host cell according to the invention may include an ortholog of the rhlA gene, of the rhlB gene and/or the rhlC gene. An ortholog, or orthologous gene, is a gene with a sequence that has a portion with similarity to a portion of the sequence of a known gene, but found in a different species than the known gene. An ortholog and the known gene originated by vertical descent from a single gene of a common ancestor. As used herein an ortholog encodes a protein that has a portion of at least about 50%, such as at least about 55%, at least about 60%, at least about 65%, at least about 70%, at least about 75%, at least about 80% or at least about 80% of the total length of the sequence of the encoded protein that is similar to a portion of a length of at least about 50%, such as at least about 55%, at least about 60%, at least about 65%, at least about 70%, at least about 75%, at least about 80% or at least about 80% of a known protein. The respective portion of the ortholog and the respective portion of the known protein to which it is similar may be a continuous sequence or be fragmented into 1 to about 3, including 2, individual regions within the sequence of the respective protein. These 1 to about 3 regions are arranged in the same order in the amino acid sequence of the ortholog and the amino acid sequence of the known protein. Such a portion of an ortholog has an amino acid sequence that has at least about 40%, at least about 45%, such as at least about 55%, at least about 60%, at least about 65%, at least about 70%, at least about 75% or at least about 80% sequence identity to the amino acid sequence of the known protein encoded by a rhlA gene, a rhlB gene or a rhlC gene, respectively.

The protein encoded by an ortholog of the rhlA gene, the rhlB gene or the rhlC gene may be identified in a database as a Rhamnosyltransferase. An ortholog of a Rhamnosyltransferase encoded by an ortholog of a rhlA gene may also be identified as an alpha/beta hydrolase fold protein in a database. An ortholog of a Rhamnosyltransferase encoded by an ortholog of a rhlB gene may in a database also be identified as a glycosyl transferase. An ortholog of a Rhamnosyltransferase encoded by an ortholog of a rhlC gene may in a database also be identified as a Rhamnosyltransferase chain C. An ortholog of the rhlA gene, the rhlB gene or the rhlC gene may also be indicated as being of unknown function in a database. Accordingly, a lack of classification as a Rhamnosyltransferase in a database does not exclude a protein with a portion of similar sequence to a known Rhamnosyltransferase from being an ortholog.

Any rhlA gene may be included in the bacterial host cell according to the invention. Examples include, but are not limited to, a gene encoding the rhlA protein of *Pantoea ananatis*, strain LMG 20103, with SwissProt accession no. D4GK92 (Version 6 of 11 Jan. 2011), of *Pantoea ananatis* AJ13355, with SwissProt accession no. F2EY06 (Version 1 of 31 May 2011), *Pseudomonas aeruginosa*, with SwissProt accession no. Q51559 (30 Nov. 2010, version 60), of *Burkholderia thailandensis*, strain E264/ATCC 700388/DSM 13276/CIP 106301, SwissProt accession no. Q2T424 (version 25 of 30 Nov. 2010), of *Burkholderia pseudomallei*, strain 1106a, SwissProt accession no. A3P349 (version 19 of 11 Jan. 2011), of *Burkholderia pseudomallei*, strain 1710a, SwissProt accession no. C6U4Y4 (version 5 of 11 Jan. 2011), of *Burkholderia pseudomallei*, strain 1710b, SwissProt accession no. Q3JGQ8 (version 30 of 11 Jan. 2011), of *Burkholderia pseudomallei* 1106b, SwissProt accession no. C5ZMA0 (Version 4 of 11 Jan. 2011), of *Burkholderia pseudomallei*, strain 668, SwissProt accession no. A3NHI8 (version 20 of 11 Jan. 2011), *Burkholderia pseudomallei* 406e, SwissProt accession no. A8EAW6 (version 5 of 11 Jan. 2011), of *Burkholderia mallei*, SwissProt accession no. Q62CH3 (Version 32 of 11 Jan. 2011), of *Burkholderia mallei*, strain SAVP1, SwissProt accession no. A1UVS0 (version 18 of 11 Jan. 2011), of *Burkholderia mallei*, strain NCTC 10247, SwissProt accession no. A3MEC2, (version 19 of 11 Jan. 2011), of *Burkholderia mallei* JHU, SwissProt accession no. A5XJN3 (Version 7 of 11 Jan. 2011), of *Burkholderia glumae*, strain BGR1, SwissProt accession no. C5AMF7 (version 9 of 30 November 30), of *Burkholderia gladioli* BSR3, SwissProt accession no. F2LKI9 (version 1 of 31 May 2011), of *Burkholderia ambifaria*, strain MC40-6, SwissProt accession no. B1Z031 (version 13 of 30 Nov. 2010) of *Dickeya dadantii*, strain 3937, SwissProt accession no. EOSMT5 (version 5 of 5 Apr. 2011), of *Pseudomonas fluorescens*, strain SBW25, SwissProt accession no. C3K3D6 (version 10 of 11 Jan. 2011), of *Pseudomonas* sp. DHT2, SwissProt accession no. A1YW88 (Version 5 of 19 Jan. 2010) and of *Pseudomonas aeruginosa*, strain PA7, SwissProt accession no. A6V1U6 (version 19 of 30 Nov. 2010), to name a few. As four examples of a respective rhlA gene may serve the gene of EMBL-Bank accession no. CP000744.1 of *Pseudomonas aeruginosa* PA7, the gene of NCBI Gene ID 4888867 of *Burkholderia pseudomallei* strain 668, the gene of NCBI GeneID 8894591 of the *Pantoea* ananatis LMG 20103 chromosome (NCBI reference sequence NC_013956.2), the gene of NCBI GeneID: 9733431 of the *Dickeya dadantii* 3937 chromosome (NCBI reference sequence NC_014500.1).

Further proteins have been identified that are likely to define rhamnosyltransferase 1A subunits. A gene encoding such a protein can likewise be employed as long as it results in the formation of a functional rhamnosyltransferase subunit. Based on sequence similarity on the protein level, examples of genes encoding probable rhamnosyltransferase 1A subunits include, but are not limited to, a gene encoding the protein of *Pseudomonas putida*, strain W619, SwissProt accession no. B1J418 (version 14 of 30 Nov. 2010), the protein of *Pseudomonas mendocina*, strain ymp, SwissProt accession no. A4XS03 (version 20 of 31 May 2011), the protein of *Pseudomonas* sp. TJI-51, SwissProt accession no. FOE3C8 (version 2 of 31 May 2011), the protein of *Pseudomonas* sp. DHT2, SwissProt accession no. A1YW88 (version 5 of 19 Jan. 2010), the protein of *Pseudomonas syringae* pv. *Phaseolicola*, strain 1448A/Race 6, SwissProt accession no. Q48HB4 (Version 29 of 11 Jan. 2011), the protein of *Pseudomonas savastanoi* pv. *savastanoi* NCPPB 3335, SwissProt accession no. D71414 (version 2 of 5 Apr. 2011), the protein of *Pseudomonas* sp. USM 4-55, SwissProt accession no. B7SJG2 (version 4 of 10 Aug. 2010), the protein of *Pseudomonas nitroreducens*, SwissProt accession no. Q93LI7 (version 18 of 5 Oct. 2010), the protein of *Pseudomonas entomophila*, strain L48, SwissProt accession no. Q115S9 (version 27 of 11 Jan. 2011), the protein of *Pseudomonas brassicacearum* subsp. *brassicacearum* NFM421, SwissProt accession no. F2KE24 (version 1 of 31 May 2011), the protein of *Pseudomonas stutzeri* (*Pseudomonas perfectomarina*), SwissProt accession no. Q8KSD5 (version 1 of 5 Oct. 2010), the protein of *Pseudomonas fluorescens*, SwissProt accession no. B1PWE2 (version 6 of 5 Oct. 2010), the protein of *Pseudomonas oleovorans*, SwissProt accession no. Q9KJH8 (version 33 of 31 May 2011), the protein of *Pseudomonas* sp. USM 4-55, SwissProt accession no. B7SJG2 (version 4 of 10 Aug. 2010), the protein of *Pseudomonas pseudoalcaligenes*, SwissProt accession no. Q93MS5 (version 25 of 5 Oct. 2010), the protein of *Burkholderia ambifaria*, strain MC40-6, SwissProt accession no. B1Z031 (version 1 of 30 Nov. 2010), the protein of *Burkholderia ambifaria*, strain ATCC BAA-244/AMMD, SwissProt accession no. Q0B714 (version 22 of 11 Jan. 2011), the protein of *Burkholderia ambifaria* MEX-5, SwissProt accession no. B1T5A9 (version 5 of 10 Aug. 2010), the protein of *Burkholderia ambifaria* 10P40-10 with SwissProt accession no. B1FHM8 (version 6 of 5 Oct. 2010), the protein of *Burkholderia* sp. TJI49, SwissProt accession no. FOGF54 (Version 2 of 31 May 2011), the protein of *Burkholderia cenocepacia*, strain AU 1054, SwissProt accession no. Q1BQD9 (Version 21 of 30 Nov. 2010), the protein of *Burkholderia cenocepacia*, strain MCO-3, SwissProt accession no. B1K710 (30 Nov. 2010), the protein of *Burkholderia cepacia*, strain J2315/LMG 16656, SwissProt accession no. B4EHI9 (version 13 of 11 Jan. 2011), the protein of *Burkholderia* sp. strain 383 (*Burkholderia cepacia* strain ATCC 17760/NCIB 9086/R18194 (version 26 of 30 November), the protein of *Burkholderia caryophylli*, SwissProt accession no. Q93LI6 (Oct. 5, 2010. Version 20), the protein of *Burkholderia ubonensis* Bu, NCBI accession no. ZP_02376540.1 (as of 9 Dec. 2010), the protein of *Brevundimonas* sp. BAL3, SwissProt accession no. B4WER6 (version 6 of 10 Aug. 2010), the protein of *Acidovorax ebreus*, strain TPSY, SwissProt accession no. B9MA04 (version 12 of 30 Nov. 2010), the protein of *Acidovorax* sp. strain JS42, SwissProt accession no. A1W249 (version 26 of 30 Nov. 2010), the protein of *Dickeya dadantii*, strain Ech703, SwissProt accession no. C6C8B4 (version 8 of 30 Nov. 2010), the protein of *Dickeya dadantii*, strain Ech586, SwissProt accession no. D2C1P1 (version 7 of 30 Nov. 2010), the protein of *Dickeya dadantii*, strain 3937 (*Erwinia chrysanthemi*, strain 3937), SwissProt accession no. EOSMT5 (Version 5 of 5 Apr. 2011), the protein of *Dickeya zeae*, strain Ech1591, SwissProt accession no. C6CKC2 (version 8 of 30 Nov. 2010), the protein of *Serratia odorifera* DSM 4582, SwissProt accession no. D4E5A8 (version 4 of 5 Apr. 2011), the protein of *Nocardia farcinica* with SwissProt accession no. Q5YPG5 (version 35 of 30 Nov. 2010), the protein of *Anaeromyxobacter dehalogenans*, strain 2CP-C, with SwissProt accession no. Q21K44 (version 33 of 30 Nov. 2010), the protein of *Anaeromyxobacter dehalogenans*, strain 2CP-1/ATCC BAA-258, with SwissProt accession no. B8J5U1 (version 11 of 30 Nov. 2010), the protein of *Amycolatopsis mediterranei*, strain U-32, with SwissProt accession no. D81794 (version 4 of 11 Jan. 2011) and the protein of *Halothiobacillus neapolitanus*, strain ATCC 23641/c2 (*Thiobacillus neapolitanus*), SwissProt accession no. D0KWX9 (version 6 of 30 Nov. 2010).

Any rhlB gene may be included in the bacterial host cell according to the invention. Examples include, but are not limited to, a gene encoding the rhlB protein of *Pseudomonas aeruginosa*, with SwissProt accession no. D2EDM4 (version 5 of 8 Mar. 2011), of *Pseudomonas aeruginosa*, strain UCBPP-PA14, with SwissProt accession no. Q02QW7 (version 27 of 8 Mar. 2011), of *Pseudomonas aeruginosa*, strain PA7, with SwissProt accession no. A6V1U7 (Version 23 of 8 Mar. 2011), of *Pseudomonas* sp. BSFD5, with SwissProt accession no. D91V58 (Version 4 of 8 Mar. 2011), of *Pseudomonas aeruginosa* 2192 with SwissProt accession no. A3LDS3 (Version 17 of 8 Mar. 2011), of *Burkholderia mallei*, strain SAVP1, with SwissProt accession no. A1UVR8 (version 20 of 8 Mar. 2011), of *Burkholderia mallei* ATCC 10399, SwissProt accession no. A9K2T0 (version 14 of 8 Mar. 2011), of *Burkholderia mallei* JHU, SwissProt accession no. A5XJN5 (version 14 of 8 Mar. 2011), of *Burkholderia mallei* PRL-20, SwissProt accession no. C5NA24 (version 5 of 8 Mar. 2011), of *Burkholderia pseudomallei*, strain 1106a, SwissProt accession no. A3P351 (Version 21 of 8 Mar. 2011), of *Burkholderia pseudomallei*, strain 1106b, SwissProt accession no. C5ZMA2 (Version 6 of 8 Mar. 2011), of *Burkholderia thailandensis*, strain E264/ATCC 700388/DSM 13276/CIP 106301, SwissProt accession no. Q2T425 (Version 32 of 8 Mar. 2011), of *Dickeya dadantii*, strain 3937 (*Erwinia chrysanthemi*, strain 3937), SwissProt accession no. E0SJM9 (Version 6 of 5 Apr. 2011), of *Pantoea ananatis* AJ13355, SwissProt accession no. F2EY05 (Version 1 of 13 May 2011), of *Pantoea ananatis*, strain LMG 20103, SwissProt accession no. D4GK91 (Version 7 of 8 Mar. 2011), of *Blastopirellula marina* DSM 3645, SwissProt accession no. A4A1V5 (Version 13 of 8 Mar. 2011) and of *Acidobacterium* sp. MP5ACTX8, SwissProt accession no. D6UX52 (Version 3 of 11 Jan. 2011).

As a few examples of a respective rhlB gene may serve the *Pantoea ananatis* LMG 20103gene of EMCBI Gene ID 8894590 (as of 12 May 2011), the *Pseudomonas aeruginosa* PAO1 gene of EMCBI Gene ID 878954 (as of 10 Mar. 2011), the *Burkholderia pseudomallei* 1106a gene of EMCBI Gene ID 4905917 (as of 14 Jan. 2011), the *Burkholderia mallei*, strain SAVP1, gene of EMCBI Gene ID 4678088 (as of 12 Mar. 2010), the *Burkholderia mallei*, strain ATCC 23344, gene of EMCBI Gene ID 3086474 (as of 22 Mar. 2011), the *Burkholderia mallei*, strain ATCC 23344, gene of EMCBI Gene ID 3087541 (as of 22 Mar. 2011)

Similar to the rhamnosyltransferase 1A protein, further proteins have been identified that are likely to define rhamnosyltransferase 1B subunits. A gene that encodes such a protein can likewise be employed as long as it results in the formation of a functional rhamnosyltransferase subunit. On the basis of sequence similarity on the protein level, examples of genes encoding probable rhamnosyltransferase 1B subunits include, but are not limited to, a gene encoding the protein of *Burkholderia pseudomallei* with SwissProt accession no. Q63KL0 (Version 35 of 8 Mar. 2011), the protein of *Burkholderia pseudomallei* 305, SwissProt accession no. A4LRW4 (Version 13 of 11 Jan. 2011), the protein of *Burkholderia cenocepacia*, strain HI2424, SwissProt accession no. A0B2F2 (Version 24 of 8 Mar. 2011), the protein of *Burkholderia cenocepacia*, strain MCO-3, SwissProt accession no. B1K712 (Version 13 of 8 Mar. 2011), the protein of *Burkholderia cepacia*, strain J2315/LMG 16656 (Burkholderia cenocepacia, strain J2315), SwissProt accession no. B4EHI7 (Version 13 of 8 Mar. 2011), the protein of *Burkholderia cenocepacia*, strain AU 1054, SwissProt accession no. Q1BQD7 (Version 31 of 8 Mar. 2011), the protein of *Burkholderia ambifaria*, strain ATCC BAA-244/AMMD, (*Burkholderia cepacia*, strain AMMD), SwissProt accession no. Q0B716 (Version 28 of 8 Mar. 2011), the protein of *Burkholderia glumae*, strain BGR1, SwissProt accession no. C5AMF8 (Version 10 of 8 Mar. 2011), the protein of *Burkholderia gladioli* BSR3, SwissProt accession no. F2LT33 (Version 1 of 31 May 2011), the protein of *Burkholderia* sp. TJI49, SwissProt accession no. FOGF56 (Version 2 of 31 May 2011), the protein of *Burkholderia multivorans* CGD2M with SwissProt accession no. B9C4N0 (Version 6 of 8 May 2011), the protein of *Dickeya dadantii*, strain Ech586, SwissProt accession no. D2BRY4 (Version 8 of 8 Mar. 2011), the protein of *Dickeya dadantii*, strain Ech703, SwissProt accession no. C6C959 (Version 9 of 8 Mar. 2011), the protein of *Dickeya zeae*, strain Ech1591, SwissProt accession no. C6CEW6 (Version 9 of 8 Mar. 2011), the protein of *Polaromonas* sp. strain J5666/ATCC BAA-500, SwissProt accession no. Q121J6 (Version 32 of 8 Mar. 2011), the protein of *Methylobacterium extorquens*, strain PA1, SwissProt accession no. A9W4M1 (Version 19 of 8 Mar. 2011), the protein of *Methylocystis* sp. ATCC 49242, SwissProt accession no. E8KZV1 (Version 2 of 31 May 2011), the protein of *Methylobacterium chloromethanicum*, strain CM4/NCIMB 13688, SwissProt accession no. B7L372 (Version 12 of 8 Mar. 2011), the protein of *Acidobacterium* sp. MP5ACTX8, SwissProt accession no. D6UZE1 (Version 4 of 8 Mar. 2011), the protein of *Acidobacterium capsulatum*, strain ATCC 51196/DSM 11244/JCM 7670, SwissProt accession no. C1F8F6 (Version 11 of 8 Mar. 2011), the protein of *Solibacter usitatus*, strain Ellin6076, SwissProt accession no. Q023U1 (Version 25 of 8 Mar. 2011) and the protein of *Maritimibacter alkaliphilus* HTCC2654, SwissProt accession no. A3VBK0 (Version 15 of 8 March 2011).

Without being bound by theory, it is speculated that placing a rhlA gene and a rhlB gene, as well as optionally an a rhlC gene, under the control of a heterologous promoter overcomes a major barrier in terms of high expression of rhamnolipids during fermentation. The endogenous promoters of the a rhlA gene, the rhlB gene, and the rhlC gene of a bacterial cell are subject to control of expression activity by signaling pathways. The inventors have found that the use of heterologous promoters avoids this signaling regulation. For *P. aeruginosa* the pathways controlling expression of rhamnolipids has been well characterized (for an overview see e.g. Daniels, R., FEMS Microbiology Reviews (2004) 28, 261-289). The expression of all three genes involved in rhamnolipid synthesis, i.e. the rhlA gene, the rhlB gene and the rhlC gene, is transcriptionally regulated by two hierarchical "quorum sensing" systems. Quorum sensing is a general term characterising a specific type of regulation of bacterial gene expression that operates under conditions of high cell density of the bacterial population. It can be taken to represent a form of communication between cells belonging to the same or different species, genera, and even families. This "social" behaviour is widespread among bacteria of various taxonomic groups and promotes the survival of bacteria under alternating environmental conditions. Signaling in quorum sensing is initiated by the action of low-molecular weight regulators, readily diffusible through the cytoplasmic membrane, and receptor proteins, which interact with these regulators.

In rhamnolipid synthesis the rhlAB operon is regulated by lasI/lasR and rhlI/rhlR composed of the rhlR and rhlI gene products which are clustered with rhlAB. In the context of rhamnolipid synthesis quorum sensing ensures that biosurfactant synthesis is delayed until cultures reach a high cell density, thus limiting its impact doubling timing. These quorum sensing systems are particularly active when *P. aeruginosa* is cultivated under phosphate or nitrogen limiting conditions. Under these conditions signaling induces rhamnolipid synthesis. Likewise, under iron-limiting conditions twitching motility of *P. aeruginosa* is known to be induced (cf. also above). A *P. aeruginosa* mutant that is incapable of synthesizing rhamnolipids has been reported not to show twitching motility under iron-limiting conditions (Glick, R., et al., Journal of Bacteriology (2010) 192, 12, 2973-2980). It rather formed a structured bio film under these conditions.

The $\sigma^{54}$ factor is responsible for the expression of rhlA/B under these conditions (Medina, G., et al., Microbiology (2003) 149, Pt 11, 3073-3081). LasI/R and RhlI/R are also regulating transcription of many virulence factors (Pearson, J. P., et al., Journal of Bacteriology (1997) 179, 18, 5756-5767). Rhamnolipid expression is known to be induced in the late stages of logarithmic growth (Xavier, J. B., Molecular Microbiology (2011) 79, 1, 166-179). Accordingly, the quorum sensing systems ensure that rhamnolipid synthesis is initiated when growth decreases, but kept at low levels when cells are in logarithmic growth. Since culture of bacterial cells is often carried out under conditions that favour growth in a manner resembling logarithmic growth, the quorum sensing systems prevent high expression of rhamnolipid genes that are under the control of their endogenous promoter.

The heterologous promoters, which may also be addressed as "exogenous" promoters, to which the rhlA gene and the rhlB gene are operationally linked may be any desired promoter. The term "promoter" as used herein, refers to a nucleic acid sequence needed for gene sequence expression. Promoter regions vary from organism to organism, but are well known to persons skilled in the art for different organisms. For example, in prokaryotes, the promoter region contains both the promoter (which directs the initiation of RNA transcription) as well as the DNA sequences which, when transcribed into RNA, will signal synthesis initiation. Such regions will normally include those 5'-non-coding sequences involved with initiation of transcription and translation, such as the TATA box, capping sequence or the CAAT sequence. "Heterologous" when used in the context of a promoter that drives expression of a rhl gene/operon such as rhlaA, rhlaB, or rhlC as described herein means that the promoter is not from the host cell in which it is/will be active, i.e., it is/was not isolated from and/or does naturally occur in said host cell where it is/will be active, e.g., the promoter may be an artificial or synthetic promoter that will be active in a host cell of the invention. Such a promoter is neither isolated from the host cell nor does it naturally occur therein. A heterologous promoter can be introduced before the rhlA, rhlB and/or rhlC gene(s) into the genome of a host cell which may naturally harbour these genes or the heterologous promoter may be in front of the rhl gene(s) which may be inserted as expression cassette/unit into the genome of a host cell. Also, the expression cassettes may be harboured by an extrachromosomal element that is capable of free replication such as a plasmid that is capable of replication, either as low copy or high copy plasmid.

A nucleic acid molecule, such as DNA, is said to be "capable of expressing" a polypeptide if it contains nucleotide sequences which contain transcriptional and translational regulatory information and such sequences are "operably linked" to nucleotide sequences which encode the polypeptide. An operable linkage is a linkage in which the regulatory DNA sequences and the DNA sequence sought to be expressed are connected in such a way as to permit gene sequence expression. The precise nature of the regulatory regions needed for gene sequence expression may vary from organism to organism, but shall in general include a promoter region which, in prokaryotes, contains both the promoter (which directs the initiation of RNA transcription) as well as the DNA sequences which, when transcribed into RNA, will signal synthesis initiation. Such regions will normally include those 5'-non-coding sequences involved with initiation of transcription and translation, such as the TATA box, capping sequence or CAAT sequence.

The terms "nucleic acid" and "nucleic acid molecule" as used herein refer to any nucleic acid in any possible configuration, such as single stranded, double stranded or a combination thereof. Nucleic acids include for instance DNA molecules, RNA molecules, analogues of the DNA or RNA generated using nucleotide analogues or using nucleic acid chemistry, locked nucleic acid molecules (LNA), protein nucleic acids molecules (PNA) and tecto-RNA molecules (e.g. Liu, B., et al., *J. Am. Chem. Soc.* (2004) 126, 4076-4077). A PNA molecule is a nucleic acid molecule in which the backbone is a pseudopeptide rather than a sugar. Accordingly, PNA generally has a charge neutral backbone, in contrast to for example DNA or RNA. Nevertheless, PNA is capable of hybridising at least complementary and substantially complementary nucleic acid strands, just as e.g. DNA or RNA (to which PNA is considered a structural mimic). An LNA molecule has a modified RNA backbone with a methylene bridge between C4' and O2', which locks the furanose ring in a N-type configuration, providing the respective molecule with a higher duplex stability and nuclease resistance. Unlike a PNA molecule an LNA molecule has a charged backbone. DNA or RNA may be of genomic or synthetic origin and may be single or double stranded. Such nucleic acid can be e.g. mRNA, cRNA, synthetic RNA, genomic DNA, cDNA synthetic DNA, a copolymer of DNA and RNA, oligonucleotides, etc. A respective nucleic acid may furthermore contain non-natural nucleotide analogues and/or be linked to an affinity tag or a label.

Many nucleotide analogues are known and can be used in nucleic acids used in the methods of the invention. A nucleotide analogue is a nucleotide containing a modification at for instance the base, sugar, or phosphate moieties. As an illustrative example, a substitution of 2'-OH residues of siRNA with 2'F, 2'O-Me or 2'H residues is known to improve the in vivo stability of the respective RNA. Modifications at the base moiety include natural and synthetic modifications of A, C, G, and T/U, different purine or pyrimidine bases, such as uracil-5-yl, hypoxanthin-9-yl, and 2-aminoadenin-9-yl, as well as non-purine or non-pyrimidine nucleotide bases. Other nucleotide analogues serve as universal bases. Universal bases include 3-nitropyrrole and 5-nitroindole. Universal bases are able to form a base pair with any other base. Base modifications often can be combined with for example a sugar modification, such as for instance 2'-O-methoxyethyl, e.g. to achieve unique properties such as increased duplex stability.

Two nucleic acid sequences (such as a promoter region sequence and a sequence encoding a Rhamnosyltransferase) are said to be operably linked if the nature of the linkage between the two DNA sequences does not (1) result in the introduction of a frame-shift mutation, (2) interfere with the ability of the promoter region sequence to direct the transcription of a gene sequence encoding a Rhamnosyltransferase, or (3) interfere with the ability of the gene sequence of a Rhamnosyltransferase to be transcribed by the promoter region sequence.

Thus, a promoter region would be operably linked to a DNA sequence if the promoter were capable of effecting transcription of that DNA sequence. Thus, to express a rhlA gene, a rhlB gene, or optionally a rhlC gene, transcriptional and translational signals recognized by the bacterial host are necessary.

The term "heterologous" refers to the relationship between two or more nucleic acid or protein sequences that are derived from different sources. For example, a promoter is heterologous with respect to a transcribable polynucleotide sequence if such a combination is not normally found in nature. In addition, a particular sequence may be "heterologous" with respect to a host cell in that it encodes a protein or is included in a protein, for example a recombinant protein, that is not normally expressed by the host cell. Such a heterologous protein accordingly generally is or has been inserted into the respective host cell, tissue, or species. Accordingly, a heterologous promoter is not normally coupled in vivo transcriptionally to the coding sequence of the rhlA gene, the rhlB gene, or the rhlC gene.

Other preferred promoters are synthetic promoters generated by using synthetic degenerated primers as described, for example, in U.S. Pat. No. 7,199,233 and US 2006/0014146. In some embodiments, the promoter strength may be tuned to be appropriately responsive to activation or inactivation. Yet in other embodiments, the promoter strength is tuned to constitutively allow an optimal level of expression of a gene of interest or of a plurality of gene of interest. A preferred example of a synthetic promoter has the following consensus sequence (the sequence is shown from 5' to 3', the last nucleotide at the 3' is immediately before the start codon):

```
                                                                  (SEQ ID NO: 16)
(A/T/G) (G/T/A) (C/T/G) (T/C/A/G) (C/G) TTGACA (A/T/C) (G/T/A) (G/C) (T/C/G)

(C/T) (G/A/T) (G/T/C) (A/T/G) (A/T/G) (A/T/C/G) (A/C/T) (T/G/A) (T/C/G) (G/C) (A/T/C)

(A/T/C) (G/T) TATAAT (A/G/T) (T/A/C) (C/A/T) (A/T/G/C) (G/C) (T/G/C) .
```

In some embodiments the heterologous promoter is a strong promoter. A strong promoter may for example be selected according to the approach disclosed by Dekhtyar et al. (Biotechnol Lett (2010) 32, 243-248) or according to the approach disclosed by Eskin et al. (Pacific Symposium on Biocomputing (2003) 8, 29-40). Illustrative examples of a strong promoter include, but are not limited to, the T7 and the T5 promoters, which are two bacteriophage promoters, the *Escherichia coli* lac promoter, the trc promoter or the tac promoter, which are two functional hybrid promoters derived from the trp and lac promoters, the recA promoter, which is the promoter of a repair protein, the *Escherichia coli* ribosomal RNA rrnB P1 promoter, the adenyl methyltransferase (AMT) promoters AMT-1 and AMT-2, and a synthetic promoter based on the promoter of b-glucanase Pcp7 as disclosed by Spexard et al (Biotechnol Lett (2010) 32, 243-248).

A preferred heterologous promoter is one which confers stronger (higher) expression than the tac promoter (see FIG. 18 for the strength of the tac promoter), preferably when driving expression of rhlAB gene(s). A "stronger (higher) expression than the tac promoter" means that when rhlAB gene(s), in particular those described in Example A, i.e., the rhlAB operon from *P. aeruginosa* PAO1, are driven by a promoter in a host cell, in particular in *P. putida* KT2440 at least 0.25, 0.26, 0.27, 0.28, 029, 0.30, 0.35, 0.40, 0.45, 0.5, or 0.6 g/l of one or more rhamnolipids (irrespective which rhamnolipid(s)) are produced by said host cell under the conditions described in particular in Example A. Additionally or alternatively, a preferred heterologous promoter (preferably stronger than the tac promoter) confers preferably an expression of an rhlA gene or an ortholog thereof and/or of an rhlB gene or an ortholog thereof and/or of an rhlC gene or an ortholog that leads to a maximal theoretical value of rhamnolipid production with glucose, glycerol, sucrose, octanoate or a mixture of sucrose and octanoate as sole carbon source (C mol Rl/C mol carbonsource) as described herein below. Another particularly preferred promoter is the T7 promoter. Further particularly preferred promoters are shown in SEQ ID NOs: 17, 18, 19 or 20. A still further particularly preferred promoter sequence is shown in SEQ ID NO:16 (consensus promoter sequence). Strength of expression can, for example, be determined by the amount/yield of RL production as described herein and/or by quantitative reverse transcriptase PCR (qRT-PCR) as described in the appended Examples.

Other particularly promoter sequences have the following sequences: AGCTCTTGACAAGGTCGGAAAATT-GAAGTATAAATATCAGT (SEQ ID NO:17), TTTCCTT-GACAAGCCTAGTTTCGCCATTTATAATGACTCG (SEQ ID NO:18), GGTGGTTGACATTGGCATTA-CAACGTATTATAATTTAGCG (SEQ ID NO:19) or TAGAGTTGACACACCTTCGGGTGGGCCT-TATAATACTCGC (SEQ ID NO:20). All sequences are shown from 5' to 3', the last nucleotide at the 3' is immediately before the start codon).

The heterologous promoter may also be equipped with a regulatory sequence/element that makes the promoter inducible and/or repressible.

The host cell of the present invention has (or is capable of achieving) preferably a carbon yield Cmol rhamnolipid/Cmol substrate ($Cmol_{rhamnolipid}/Cmol_{substrate}$, with "C" meaning carbon) of more than 0.18, more preferably more than 0.19, even more preferably more than 0.20, even yet more preferably more than 0.21, particularly preferable more than 0.22 or 0.23. This yield is higher than the yield achieved in the prior art thus far (see Trummler et al. (0.18), Cha et al. (0.17), Müller et al. (0.07), Wang et al. (0.07), Ochsner et al. (0.17), Cabrera-Valladares et al. (0.04)). Substrates can be glucose, oleic acid, soybean oil, or glycerol, with glucose being preferred. The host cell of the present invention that is capable of achieving a carbon yield of more than 0.18 Cmol rhamnolipid/Cmol substrate achieves the carbon yield, since the rhlA and/or rhlB and/or rhlC gene(s) is/are expressed under the control of a heterologous promoter that confers strong (high) expression of said gene(s). It is no undue burden for the skilled person to put such a promoter into practice, since strong promoters, even stronger promoters than the tac promoter (used by Ochsner et al.) are known or can be easily synthesized and screened for strong (high) expression. For example, it can be tested as to whether a promoter confers a stronger expression than the tac promoter as described elsewhere herein. If so, such a promoter is encompassed by the present invention. It is a preferred embodiment that the rhlA, rhlB and/or rhlC gene(s) is/are driven by the same heterologous promoters.

The calculation of the carbon yield coefficient Cmol rhamnolipid/Cmol substrate is preferably done as described in Stephanopoulos, Aristidou and Nielsen in Metabolic engineering: principles and methodologies (San Diego: Acad. Press, 1998), Chapter 4 and/or Chapter 8. Other sources for the calculation and application of the carbon yield coefficient are, for example, Koch et al. (1991), J. Bacteriol 173(13):4214.4219 or Heyd et al. (2008), Anal Bioanal Chem 391:1579-1590. To ensure comparability of the results, the unit Cmol is preferably chosen, since it normalizes the rhamnolipid production rate to the amount of carbon atoms present in the carbon substrate.

Alternatively, the carbon yield can be indicated as % of the theoretical maximum of the yield Cmol rhamnolipid/Cmol substrate. Accordingly, the host cell of the present invention has preferably more than 23.9, 24.0, 24.5, or 25.0% of the theoretical maximum of the carbon yield Cmol rhamnolipid/Cmol substrate ($Cmol_{rhamnolipid}/Cmol_{substrate}$, with "C" meaning carbon). More preferably the host cell of the present invention has more than 26, 27, 28, 29, 30, or 31% of the theoretical maximum of the carbon yield Cmol rhamnolipid/Cmol substrate ($Cmol_{rhamnolipid}/Cmol_{substrate}$, with "C" meaning carbon). The theoretical maximum is calculated by the assumption that all C atoms of the substrate (i.e., carbon source) are incorporated into a rhamnolipid. The percent value of the theoretical maximum of the carbon yield Cmol rhamnolipid/Cmol substrate of the host cell of the present invention is preferably higher than that achieved by the prior art ((see Trummler et al. (19.8%), Cha et al. (17.9%), Müller et al. (7.6%), Wang et al. (4.4%), Ochsner et al. (23.9%), Cabrera-Valladares et al. (1.1%)). Note that when "oils" such as soybean oil or sunflower oil is used as substrate, for example, in Müller et al., Trummler et al., Cha et al., Wang et al., or Cabrera-Valladares et al., the theoretical maximum is given in relation to octanoate. Substrates can be glucose, oleic acid, soybean oil, or glycerol, with glucose being preferred.

In some embodiments the bacterial host cell further includes a rhlC gene or an ortholog thereof, that is under the control of a heterologous promoter, preferably a promoter as described herein. In some embodiments the rhlC gene or the respective ortholog is under the control of a promoter that is different from the promoter of the rhlC gene. In some embodiments the rhlC gene is a homologous, including an endogenous gene of the bacterial host cell. In some embodiments the rhlC gene is a heterologous gene.

A rhlC gene included in the bacterial host cell according to the invention may be any rhlC gene. Examples of a suitable gene include, but are not limited to, a gene encoding the rhlC protein of *Pseudomonas aeruginosa* with SwissProt accession no. D2EDP8 (version 6 of 31 May 2011), of *Pseudomonas aeruginosa*, strain UCBPP-PA14 with SwissProt accession no. Q021V0 (Version 22 of 31 May 2011), of *Pseudomonas aeruginosa* with SwissProt accession no. D2EDQ3 (Version 4 of 31 May 2011), of *Burkholderia mallei* ATCC 10399 with SwissProt accession no. A9K2T2 (Version 14 of 31 May 2011), of *Burkholderia mallei*, strain NCTC 10247, SwissProt accession no. A3MEB8 (Version 21 of 31 May 2011), of *Burkholderia pseudomallei* Pasteur 52237 with SwissProt accession no. A8 KHX2 (Version 13 of 31 May 2011) and of *Burkholderia pseudomallei* S13 with SwissProt accession no. B1HLL2 (Version 8 of 31 May 2011).

Further rhamnosyltransferases have been identified that are, based on sequence identity, likely a rhamnosyltransferase-2 and thus encoded by a rhlC gene. A gene that encodes a respective protein may likewise be used as a rhlC gene as long as it results in the formation of a functional rhamnosyltransferase. Examples of a gene encoding a probable rhamnosyltransferase-2 subunits include, but are not limited to, a gene encoding the protein of *Burkholderia thailandensis*, strain E264/ATCC 700388/DSM 13276/CIP 106301 with SwissProt accession no. Q2T428 (version 26 of 31 May 2011), the protein of *Burkholderia pseudomallei* with SwissProt accession no. Q63MV9 (version 26 of 31 May 2011), of *Burkholderia glumae*, strain BGR1 with SwissProt accession no. C5AMG0 (version 9 of 31 May 2011), of *Burkholderia glumae*, strain BGR1, with SwissProt accession no. C5ABW1 (version 8 of 30 Nov. 2010), of *Burkholderia gladioli* BSR3 with SwissProt accession no. F2LKJ2 (version 1 of 31 May 2011), of *Burkholderia cenocepacia*, strain MCO-3, SwissProt accession no. B1K714 (version 14 of 31 May 2011), of *Burkholderia cenocepacia* PC184, SwissProt accession no. A2W519 (version 14 of 5 Oct. 2010), of *Burkholderia ambifaria*, strain MC40-6, SwissProt accession no. B1Z027 (Version 14 of 31 May 2011), of *Burkholderia* sp. TJI49 with SwissProt accession no. F0G014 (version 2 of 31 May 2011), of *Burkholderia phytofirmans*, strain DSM 17436/PsJN, SwissProt accession no. B2T0J7 (version 13 of 31 May 2011), of *Burkholderia phymatum*, strain DSM 17167/STM815, SwissProt accession no. B2JFC2 (version 12 of 30 Nov. 2010), of *Burkholderia multivorans* CGD2M, SwissProt accession no. B9CFN7 (version 3 of 1 Sep. 2009), of *Lautropia mirabilis* ATCC 51599, SwissProt accession no. E7RXL2 (version 2 of 31 May 2011), of *Variovorax paradoxus* EPS, SwissProt accession no. E6UV89 (version 2 of 5 Apr. 2011), of *Ralstonia solanacearum* (*Pseudomonas solanacearum*), SwissProt accession no. Q8Y1K3 (version 37 of 30 Nov. 2010), of *Ralstonia* sp. 5_7_47FAA, SwissProt accession no. E2SY52 (version 3 of 31 May 2011), of *Acidobacterium* sp. MP5ACTX8, SwissProt accession no. D6UX48 (version 2 of 5 Oct. 2010), of *Klebsiella pneumonia*, SwissProt accession no. C9K1E5 (Version 3 of 20 Apr. 2010), of *Planctomyces maris* DSM 8797, SwissProt accession no. A6C912 (version 10 of 31 May 2011), of *Ralstonia pickettii*, strain 12J, SwissProt accession no. B2U7B8 (version 14 of 31 May 2011), of *Alteromonas macleodii*, strain DSM 17117/Deep ecotype, SwissProt accession no. F2 GBW7 (version 1 of 31 May 2011), of *Methylobacterium populi*, strain ATCC BAA-705/NCIMB 13946/BJ001, SwissProt accession no. B1ZKT2 (version 15 of 30 Nov. 2010), of *Methylobacterium nodulans*, strain ORS2060/LMG 21967, SwissProt accession no. B81SX9 (version 11 of 30 Nov. 2010), of *Methylobacterium chloromethanicum*, strain CM4/NCIMB 13688, SwissProt accession no. B7 KW88 (version 11 of 30 Nov. 2010), of *Methylobacterium extorquens*, strain PA1, SwissProt accession no. A9W727 (version 13 of 30 Nov. 2010), of *Methylobacterium radiotolerans*, strain ATCC 27329/DSM 1819/JCM 2831, SwissProt accession no. B1M512 (version 14 of 30 Nov. 2010), of *Methylobacterium* sp. strain 4-46, SwissProt accession no. B0ULR4 (version 12 of 30 Nov. 2010), of *Methylotenera mobilis*, strain JLW8/ATCC BAA-1282/DSM 17540, SwissProt accession no. C6WVJ5 (version 9 of 31 May 2011), of *Lautropia mirabilis* ATCC 51599, SwissProt accession no. E7RXL2 (version 2 of 31 May 2011), of *Acidovorax* sp., strain J542, SwissProt accession no. A1W3G6 (version 27 of 31 May 2011) and of *Planctomyces maris* DSM 8797, SwissProt accession no. A6C912 (version 10 of 31 May 2011). Other rhamnosyltransferase-2 sequences are disclosed in WO 2012/013554 as enzymes "E3", "E3a", "E3b", "E3c", or "E3d".

Rhamnosyltransferase-2 catalyzes the transfer of a further rhamnosyl moiety to a mono-rhamnolipid, thereby providing a di-rhamnolipid. Accordingly, the presence of a rhlC gene and its control by a heterologous promoter may be desired in embodiments where the production of di-rhamnolipids is desired.

The present invention also provides a method for producing, preferably screening a bacterial host cell capable of producing one or more rhamnolipids in a yield as described herein, comprising (a) introducing a rhlA gene or an ortholog thereof, being under the control of a heterologous promoter;

(b) introducing a rhlB gene or an ortholog thereof, being under the control of a heterologous promoter; and (c) determining the yield of rhamnolipid production from said host cell.

Said rhamnolipid production is preferably in the yield as described herein.

In the last step, a bacterial host cell is, so to say, selected which is capable of producing one or more rhamnolipids in a yield as described herein.

In a further method step, PHA activity is preferably removed from the thus-obtainable (obtained) bacterial host cell as described herein.

In a method according to the invention a host cell is cultured under conditions that allow rhamnolipid production. Suitable conditions are within the routine knowledge of the skilled artisan. The formation of rhamnolipids can further be easily analysed and/or monitored since rhamnolipids are generally being secreted by a host cell. Accordingly, standard techniques of cell culture broth analysis, including chromatographic techniques such as HPLC, can be applied in this regard. Suitable conditions for culturing the host cell typically include culturing the same in an aqueous medium that is suitable for sustaining cell viability and cell growth. Illustrative examples of a suitable cell culture medium, for example for culturing a bacterial host such as a *Pseudomonas* sp. host or a *Burkholderia* sp. host, include, but are not limited to, Luria-Bertani (LB) complex medium, Inkasmedium, phosphate-limited protease peptone-glucose-ammonium salt medium (PPGAS), Minimal medium E (MME), nitrogen-limited minimal medium or mineral salt medium. In some embodiments, the media used may include a factor selected from growth factors and/or attachment factors. In some embodiments the media used may be void of such a factor. In some embodiments it may be sufficient to add such a factor only to the media used for the seeding of the cells and/or the growing of the cells, for example under logarithmic conditions. In some embodiments serum may be included in a media used. In some embodiments the media may be serum-free, i.e. void of any sera from animal or human origin. Suitable cell culture media may further include salts, vitamins, buffers, energy sources, amino acids and other substances.

The term "cultivation of cells" or "culturing of cells" in medium in the context of the host cells of the present invention generally refers to the seeding of the cells into a culture vessel, to the growing of the cells in medium in the logarithmic phase until a sufficient cell density is established and/or to the maintenance of the cells in medium, respectively. Culturing can be done in any container suitable for culturing cells.

In some embodiments the host cells may be removed, for example by way of centrifugation or filtration, before recovering the one or more rhamnolipids produced in a method according to the invention. In some embodiments host cells may be recovered, e.g. concentrated, captured, harvested and/or enriched in/on a separation or filter unit. For example, it is envisaged that host cells as employed in the present invention may be enriched before they are collected and/or are concentrated before they are collected and/or are captured before they are collected. Enriching may, for example, be achieved by batch centrifugation, flow through centrifugation and/or tangential flow filtration.

The rhlAA gene or ortholog thereof and the rhlB gene or ortholog thereof which are both under the control of a heterologous promoter are preferably contained in a rhlA-library comprising one or more rhlA genes and/or orthologs thereof as described herein which are operably fused with synthetic promoters and/or in a rhlB-library comprising one or more rhlB genes and/or orthoogs thereof as described herein which are operably fused with synthetic promoters. Accordingly, a rhlA-library and a rhlB library is transformed into a bacterial host cell as described herein and the bacterial host cell that produces the desired yield of one or more rhamnolipids is selected.

Thus, in a preferred aspect the present invention relates to a method for producing, preferably screening a host cell, preferably a bacterial host cell capable of producing one or more rhamnolipids in a yield as described herein, comprising (a) introducing a rhlA-library into a host cell, preferably bacterial host cell;

(b) introducing a rhlB-library into a host cell, preferably bacterial host cell; and (c) determining the yield of rhamnolipid production from said host cell as described herein.

The yield of rhamnolipid production of the host cell is preferably as described herein, i.e., of more than 0.18 Cmol rhamnolipid/Cmol substrate.

The rhlA, rhlB and/or rhlC genes of the each of the library is preferably driven by a heterologous promoter that is preferably stronger than the tac promoter. An appropriate test for a promoter that is stronger than the tac promoter is described herein elsewhere. In another preferred embodiment, a rhlA, rhlB and/or rhlC gene is fused with a promoter library such as a synthetic promoter library. A starting basis for a promoter library could be the consensus sequence shown in SEQ ID NO: 16. Said consensus sequence can be randomized and cloned into vectors and used for the purposes of the present invention.

In another aspect, the present invention provides a bacterial host cell obtainable (obtained) by the methods of producing, preferably selecting or screening a bacterial host cell a described herein, in particular above.

In some embodiments the bacterial host cell according to the invention is able to produce poly(3-hydroxyalkanoates) (PHA) only to a much lower extent than a corresponding native, wild type bacterial host cell. The bacterial host cell may for example include a mutation in the gene of an enzyme that catalyses the formation of PHA, or a mutation in a regulatory sequence to which the respective gene is operably linked. The respective mutation may in some embodiments give rise to the formation of a polyhydroxyalkanoic acid synthase that has a reduced activity when compared to a corresponding wild type polyhydroxyalkanoic acid synthase. In some embodiments a capability of the bacterial host cell according to the invention to produce PHA is reduced in comparison to a wild type cell, including entirely absent. In some embodiments the bacterial host cell according to the invention is incapable of synthesizing PHA. The PHA biosynthetic pathway of the bacterial host cell may for example be curtailed, including inactive. The bacterial host cell may for example have one or more genes in the PHA synthesis pathway, such as polyhydroxyalkanoic acid synthase gene(s), that is/are disrupted (cf. FIG. 1). The cell may for instance have a knock-out mutation in an endogenous polyhydroxyalkanoic acid synthase gene. Such a polyhydroxyalkanoic acid synthase gene, which may be partially or fully inactivated, disrupted or otherwise blocked, may for example be a poly(3-hydroxyalkanoic acid) synthase gene such as the poly(3-hydroxyalkanoic acid) synthase 1 gene (phaC1).

Any means known in the art may be used to achieve a gene-silencing effect of the phaC1 gene, i.e. to achieve a reduction of the phaC1 gene in the host cell. In some embodiments the amount of PHA-synthase 1, the product of the phaC1 gene, in the host cell is reduced by introducing a heterologous molecule into the cell, such as a nucleic acid molecule. As an illustrative example reduction, including suppression of expression of the phaC1 gene can be achieved by introduction of a silencing RNA. "Expression of a target nucleic acid" refers to transcription of the nucleic acid in the cell, and the reduced expression may be observed or measured by a reduced level of production or accumulation of the transcript or a processed product, for example of an mRNA, or of a translation product of the mRNA. The transcript may or may not be processed, for example by removal of introns, and it may or may not be translated. In this regard the term "expression" encompasses transcription with or without such processes. The reduction of expression may be the result of reduction of transcription, including via methylation of chromatin remodelling, or post-transcriptional modification of the RNA molecules, including via RNA degradation, or both. As indicated above, gene-silencing does not necessarily amount to abolishing the expression of the phaC1 gene. It is generally sufficient that the level expression of the phaC1 gene, for example in the presence of a silencing RNA, is lower than in a wild type host cell, e.g. in the absence of a silencing RNA. The level of expression may in some embodiments be reduced by at least about 10%, by at least about 15%, by at least about 20%, by at least about 25%, at least about 30%, at least about 35%, at least about 40%, at least about 45%, at least about 50%, at least about 55%, at least about 60%, at least about 65%, at least about 70%, at least about 75%, at least about 80%, at least about 85% or more, including about 90% or more, about 95% or more including about 100%.

In this regard, a "silencing RNA" or "silencing RNA molecule", which may also be referred to as "inhibitory RNA" or an "inhibitory RNA molecule" may be any RNA molecule which upon introduction into a host cell reduces the expression of a target gene, typically through transcriptional and/or post-transcriptional silencing. Such silencing RNA may e.g. be so-called "antisense RNA", whereby the RNA molecule includes a sequence of at least 20 consecutive nucleotides having at least 95% sequence identity to the complement of the sequence of the target nucleic acid, such as the coding sequence of the target gene. Nevertheless, antisense RNA may also be directed to regulatory sequences of target genes, including the promoter sequences and transcription termination and polyadenylation signals. Silencing RNA further includes so-called "sense RNA" whereby the RNA molecule includes a sequence of at least 20 consecutive nucleotides having at least 95% sequence identity to the sequence of the target nucleic acid. Sense RNA may also be directed to regulatory sequences of target genes, including the promoter sequences and transcription termination and polyadenylation signals.

In some embodiments the amount of PHA-synthase 1 in the host cell is reduced by introducing a non-coding nucleic acid molecule into the host cell, such as for example an aptamer or a Spiegelmer® (described in WO 01/92655). A non-coding nucleic acid molecule may also be an nc-RNA molecule (see e.g. Costa, F F, *Gene* (2005), 357, 83-94 for an introduction on natural nc-RNA molecules). Examples of nc-RNA molecules include, but are not limited to, an anti-sense-RNA molecule, an L-RNA Spiegelmer®, a silencer-RNA molecule (such as the double-stranded Neuron Restrictive Silencer Element), a micro RNA (miRNA) molecule, a short hairpin RNA (shRNA) molecule, a small interfering RNA (siRNA) molecule, a repeat-associated small interfering RNA (rasiRNA) molecule or an RNA that interacts with Piwi proteins (piRNA) (for a brief review see e.g. Lin, H., *Science* (2007) 316, 397). Such non-coding nucleic acid molecules can for instance be employed to direct mRNA degradation or disrupt mRNA translation.

The use of small interfering RNAs has become a tool to "knock down" specific genes. An overview on the differences between the use of synthetic small organic compounds and RNAi has been given by Weiss et al. (Nature Chem. Biol. (2007) 3, 12, 739-744). Small interfering RNA makes use of gene silencing or gene suppression through RNA interference (RNAi), which occurs at the posttranscriptional level and involves mRNA degradation. RNA interference represents a cellular mechanism that protects the genome. SiRNA molecules mediate the degradation of their complementary RNA by association of the siRNA with a multiple enzyme complex to form what is called the RNA-induced silencing Complex (RISC). The siRNA becomes part of RISC and is targeted to the complementary RNA species which is then cleaved. This leads to the loss of expression of the respective gene (for a brief overview see Zamore, P D, & Haley, B, *Science* (2005) 309, 1519-1524). This technique has for example been applied to silencing parasitic DNA sequences, such as the cleavage of HIV RNA, as disclosed in US patent application 2005/0191618.

While a siRNA molecule is formed from heterologous double stranded RNA, a miRNA molecule is a RNA molecule transcribed from the genome, although it is structurally similar to siRNA molecules. Principally a miRNA molecule can operate in the same way as a siRNA molecule (for an overview see e.g. Liu, J., *Current Opinion in Cell Biology* (2008) 20, 214-221). While initially only miRNA was known that acted on the 3'-untranslated regions of transcripts, meanwhile miRNA has been described that can simultaneously target several sites in the coding sequence of a single mRNA molecule or the CDSs of different mRNA molecules (Tay, Y., et al., *Nature* (2008) doi:10.1038/nature07299). It was also suggested that short interfering RNA molecules can modulate gene expression through sites within the coding sequence with only partial complementarity to the siRNA (ibid.). These findings open the possibility of directing degradation or disrupting translation of selected iso forms, splice variants or mutants of a protein.

A typical embodiment of a siRNA or miRNA for the current invention includes an in vitro or in vivo synthesized molecule of about 10 to 35 nucleotides, in some embodiments about 15 to 25 nucleotides. A respective siRNA or miRNA molecule may be directly synthesized within a cell of interest, including a cell that is part of a microorganism and an animal. It may also be introduced into a respective cell and/or delivered thereto. An illustrative example of delivering a siRNA molecule into selected cells in vivo is its non-covalent binding to a fusion protein of a heavy-chain antibody fragment (Fab) and the nucleic acid binding protein protamin (Song, E. et al., *Nature Biotech.* (2005) 23, 6, 709-717). In an embodiment of the present invention siRNA and/or miRNA molecules are used to induce a degradation of mRNA molecules encoding one or more a polyhydroxyalkanoic acid synthase genes of the bacterial host cell.

As an example of a phaC1 gene, where the host cell is *Pseudomonas aeruginosa*, the respective phaC1 gene may the gene encoding the protein of SwissProt accession no. Q51513 (version 59 of 8 Feb. 2011). Where the host cell is *Pseudomonas stutzeri* (*Pseudomonas perfectomarina*), the respective phaC1 gene may be the gene encoding the protein of SwissProt accession no. Q84850 (version 12 of 10 Aug. 2010). Where the host cell is *Pseudomonas oleovorans*, the phaC1 gene may the gene encoding the protein with SwissProt accession no. P26494 (version 38 of 10 Aug. 2010). Where the host cell is *Pseudomonas putida* (*Arthrobacter siderocapsulatus*) the phaC1 gene may be the gene encoding the protein of SwissProt accession no. Q5Y153 (version 15 of 31 May 2011). Where the host cell is *Pseudomonas mediterranea* the phaC1 gene may be the gene encoding the protein of SwissProt accession no. Q2NM19 (version 7 of 22 Jul. 2008). Where the host cell is *Pseudomonas fluorescens* WH6, the phaC1 gene may be the gene encoding the protein of SwissProt accession no. E2XK22 (version 59 of 8 Mar. 2011). Where the host cell is *Pseudomonas mendocina*, strain ymp, the phaC1 gene may be the gene encoding the protein of SwissProt accession no. A4XPN2 (version 18 of 30 Nov. 2010). Where the host cell is *Pseudomonas corrugate* the phaC1 gene may be the gene encoding the protein of SwissProt accession no. Q2NM24 (version 7 of 22 Jul. 2008). Where the host cell is *Pseudomonas* sp. LDC-5 MNNG mutant, the phaC1 gene may be the gene encoding the protein of SwissProt accession no. QOZIH8 (version 12 of 13 Jul. 2010). Where the host cell is *Pseudomonas chlororaphis* (*Pseudomonas aureofaciens*), the phaC1 gene may be the gene encoding the protein of SwissProt accession no. C0LD26 (version 59 of 31 May 2011). Where the host cell is *Pseudomonas resinovorans*, the phaC1 gene may be the gene encoding the protein of SwissProt accession no. Q9X5X7 (version 25 of 10 Aug. 2010). Where the host cell is *Comamonas testosteroni* (*Pseudomonas testosteroni*), the phaC1 gene may be the gene encoding the protein of SwissProt accession no. Q5Q139 (version 14 of 10 Aug. 2010). Where the host cell is *Burkholderia caryophylli*, the phaC1 gene may be the gene encoding the protein of SwissProt accession no. Q93MW5 (version 23 of 10 Aug. 2010). Where the host cell is *Burkholderia glumae*, strain BGR1, the phaC1 gene may be the gene encoding the protein of SwissProt accession no. C5AFL2 (version 8 of 30 Nov. 2010). Where the host cell is *Burkholderia* sp. strain CCGE1002, the phaC1 gene may be the gene encoding the protein of SwissProt accession no. D5WFT4 (version 5 of 30 Nov. 2010). Where the host cell is *Burkholderia* sp. strain CCGE1003, the phaC1 gene may be the gene encoding the protein of SwissProt accession no. E1T796 (version 5 of 31 May 2011). Where the host cell is *Burkholderia phytofirmans*, strain DSM 17436/PsJN, the phaC1 gene may be the gene encoding the protein of SwissProt accession no. B2T3U0 (version 10 of 30 Nov. 2010). Where the host cell is *Burkholderia phymatum*, strain DSM 17167/STM815, the phaC1 gene may be the gene encoding the protein of SwissProt accession no. B2JT72 (version 9 of 30 Nov. 2010). Where the host cell is *Burkholderia multivorans*, strain ATCC 17616/249, the phaC1 gene may be the gene encoding the protein of SwissProt accession no. A9AH16 (version 22 of 8 Mar. 2011). In some embodiments where the host cell is *Burkholderia mallei*, the phaC1 gene may be the gene encoding the protein of SwissProt accession no. Q62JY7 (version 30 of 30 Nov. 2010). Where the host cell is *Burkholderia xenovorans*, strain LB400, the phaC1 gene may be the gene encoding the protein of SwissProt accession no. Q13Z62 (version 23 of 30 Nov. 2010). Where the host cell is *Burkholderia graminis* C4D1M, the phaC1 gene may be the gene encoding the protein of SwissProt accession no. B1FYV4 (version 3 of 8 Jul. 2008). Where the host cell is *Rhodobacter* sp. gl32, the phaC1 gene may be the gene encoding the protein of SwissProt accession no. B6UV88 (version 3 of 30 Nov. 2010). Where the host cell is *Ahrensia* sp. R2A130, the phaC1 gene may be the gene encoding the protein of SwissProt accession no. E0MTK8 (version 3 of 11 Jan. 2011). Where the host cell is *Erythrobacter* sp. NAP1, the phaC1 gene may be the gene encoding the protein of SwissProt accession no. A3WBL7 (version 7 of 3 Nov. 2009). Where the host cell is *Erythrobacter litoralis*, strain HTCC2594, the phaC1 gene may be the gene encoding the protein of SwissProt accession no. Q2N9U1 (version 29 of 8 Feb. 2011). Where the host cell is *Erythrobacter* sp. SD-21, the phaC1 gene may be the gene encoding the protein of SwissProt accession no. A5P842 (version 10 of 5 Oct. 2010). Where the host cell is gamma proteobacterium NOR51-B, the phaC1 gene may be the gene encoding the protein of SwissProt accession no. B8KX71 (version 5 of 22 Sep. 2009). Where the host cell is *Methylobacterium* sp. strain 4-46, the phaC1 gene may be the gene encoding the protein of SwissProt accession no. B0UA99 (version 15 of 30 Nov. 2010). Where the host cell is *Methylobacterium nodulans*, strain ORS2060/LMG 21967, the phaC1 gene may be the gene encoding the protein of SwissProt accession no. B81FS7 (version 11 of 30 Nov. 2010). Where the host cell is *Aeromonas* sp. KC011, the phaC1 gene may be the gene encoding the protein of SwissProt accession no. A4K5H0 (version 7 of 19 Jan. 2010).

As six examples of a respective phaC gene may serve the *Pseudomonas* sp. MBEL 6-19 PHA synthase 1 gene that has GenBank accession no FJ626663.1, the gene that has on the *Pseudomonas aeruginosa* PAO1 chromosome with NCBI Reference Sequence NC_002516.2 the positions 5695366-5697045 and the locus tag PA5056, the gene of *Pseudomonas putida* strain LS46 with location 315-1995 in GenBank accession no HQ662163.1, the *Comamonas testosteroni* gene with positions 110-1789 in the sequence of GenBank accession no AY790326.1, the phaC1 gene of *Pseudomonas* sp. HJ-2 MCL with GenBank accession no AY370934.1 and the phaC gene of *Burkholderia mallei* SAVP1, chromosome 1, located on positions 1796438-1798252 of GenBank accession no CP000526.1 and having locus tag BMASAVP1_A1811.

Again, numerous proteins, in this case PHA-synthases, have been identified that are, based on sequence identity, likely to be a poly(3-hydroxyalkanoic acid) synthase 1 and thus encoded by a phaC1 gene. Accordingly, a corresponding gene that encodes such a PHA-synthase may likewise be mutated, disrupted or otherwise downregulated inactivated. As an example, if the cell is *Burkholderia* sp. strain 383 (Burkholderia cepacia, strain ATCC 17760/NCIB 9086/R18194), the respective gene may be the gene encoding the protein of SwissProt accession no. Q396V7 (version 30 of 8 Feb. 2011). If the cell is *Burkholderia pseudomallei* the respective gene may be the gene encoding the protein of SwissProt accession no. Q63UR2 (version 32 of 30 Nov. 2010). Where the host cell is *Burkholderia pseudomallei*, strain 668, the PHA-synthase gene may be the gene encoding the protein of SwissProt accession no. A3NA30 (version 20 of 30 Nov. 2010). Where the cell is *Burkholderia caryophylli*, the respective gene may be the gene encoding the protein of SwissProt accession no. Q93MW3 (version 27 of 10 Aug. 2010). Where the cell is *Burkholderia* sp. H160, the respective gene may be the gene encoding the protein of SwissProt accession no. B5WLS2 (version 3 of 10 Feb. 2009). Where the cell is *Burkholderia multivorans* CGD2M, the PHA-synthase gene may be the gene encoding the protein of SwissProt accession no. B9C6T2 (version 3 of 1 Sep. 2009). Where the cell is *Burkholderia gladioli* BSR3, the respective gene may be the gene encoding the protein of SwissProt accession no. F2LBJ5 (version 1 of 31 May 2011). Where the cell is *Cupriavidus pinatubonensis*, strain JMP134/LMG 1197 (*Alcaligenes eutrophus*) (*Ralstonia eutropha*), the respective gene may be the gene encoding the protein of SwissProt accession no. Q46ZD1 (version 25 of 8 Feb. 2011). Where the cell is *Rhodococcus corallines* the respective gene may be the gene encoding the protein of SwissProt accession no. O52072 (version 31 of 5 Oct. 2010).

In this regard, two illustrative examples of further genes that are likely to be a respective phaC1 gene are the gene of poly(R)-hydroxyalkanoic acid synthase class I on the *Burkholderia cenocepacia* HI2424 chromosome 1, which has positions 1987918-1989783 in GenBank accession no CP000458.1 and locus tag Bcen2424_1791, as well as the gene of *Burkholderia pseudomallei* strain K96243, located on positions 1777009-1778814 of chromosome 1 with GenBank accession no BX571965.1.

Figure 1:
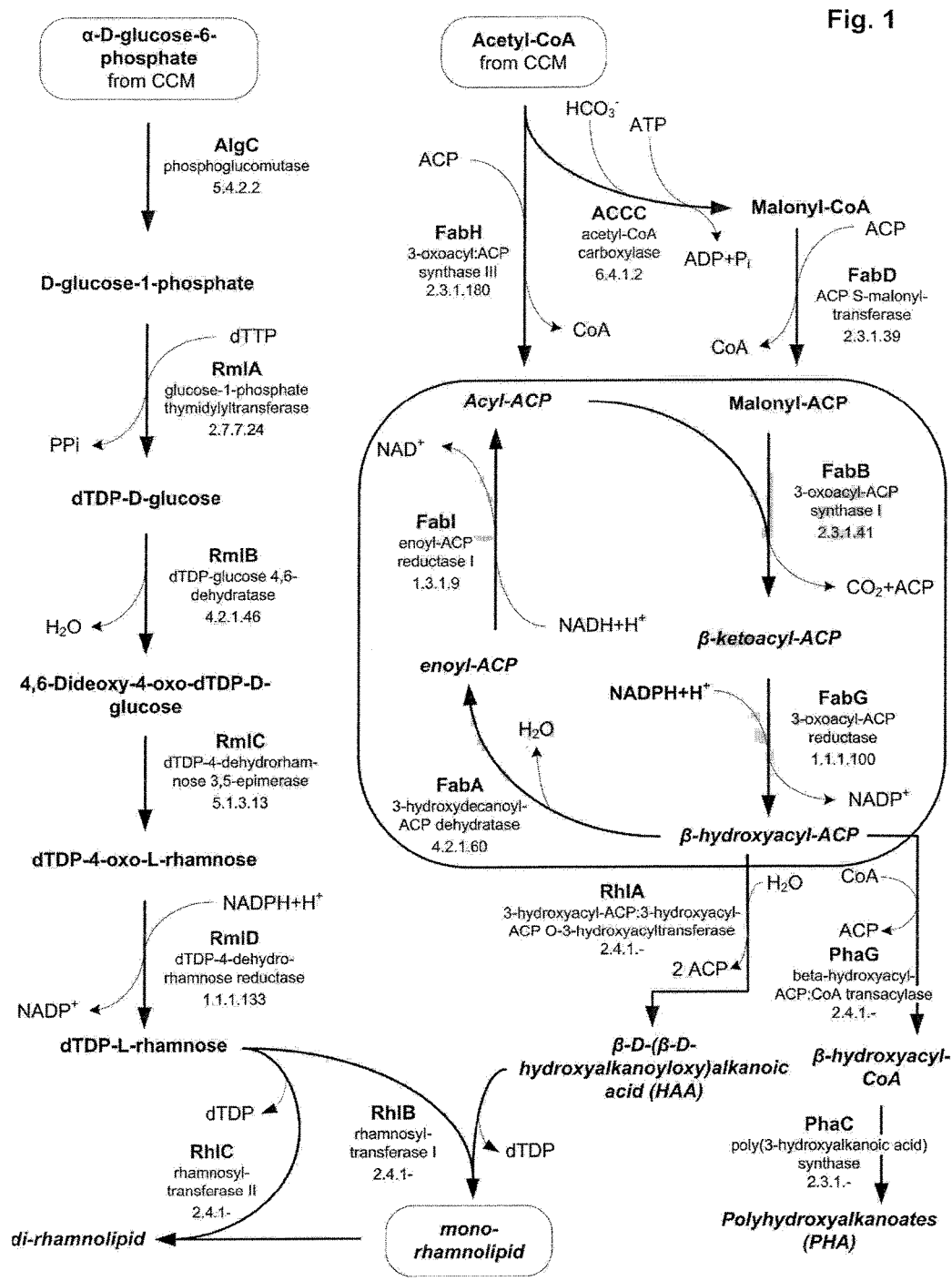
FIG. 1 depicts the rhamnolipid production network pathway in *P. putida*. All enzymatic steps required for the synthesis of essential precursors including host-intrinsic biocatalysts enzymes and heterologous RhlA and RhlB are shown.

As depicted in FIG. 1, metabolism of a bacterial cell such as *P. putida* uses β-hydroxyacyl-ACP from de-novo fatty acid synthesis as a precursor in PHA biosynthesis. The β-hydroxyacyl-ACP is converted to β-hydroxyacyl-CoA by PhaG β-hydroxyacyl-ACP:CoA transacylase. The enzyme PhaC1 poly(3-hydroxyalkanoic acid) synthase 1 catalyzes the reaction leading to PHA. Choi et al. (Journal of Biotechnology (2011) 151, 30-42) reported that rhamnolipid production was slightly decreased or at similar levels in PHA-defective mutants of *P. aeruginosa* PA14 and PAO1, carrying a mutation in the gene of poly(3-hydroxyalkanoic acid) synthase, when compared to the wild-type. It thus appeared that a change in carbon flux into PHA biosynthesis has no effect on the rate of rhamnolipid synthesis. The inventors, however, made the surprising finding that reducing or blocking PHA synthesis in a host cell according to the invention, that is with a rhlA gene and a rhlB gene under the control of a heterologous promoter, however, stimulates rhamnolipid production.

Host cells which may be used in the expression systems of the present invention are not strictly limited, provided that they are suitable for use in the expression of subunits A and B of rhamnosyltransferase 1. The host cell is preferably non-pathogenic for humans. The non-pathogenic host cell is preferably a soil bacterium. Where both a homologous rhlA gene and/or a homologous rhlB gene are to be placed under the control of a heterologous promoter, a bacterial host may be selected that has a respective endogenous rhlA gene and/or endogenous rhlB gene. A suitable host having both endogenous rhlA gene and rhlB genes may for example be selected from a bacterial isolate that has been found to produce rhamnolipids, for example of *Acinetobacter calcoaceticus*, *Renibacterium salmoninarum*, *Cellulomonas cellulans*, *Nocardioides* sp., *Tetragenococcus koreensis*, *B. glumae*, *B. pseudomallei*, *B. plantarii*, *B. thailandensis*, *Myxococcus* sp., *Acinetobacter calcoaceticus*, *Enterobacter asburiae*, *Enterobacter hormaechei*, *Pantoea stewartii*, *Pseudomonas alcaligenes*, *Pseudomonas aeruginosa*, *Pseudomonas cepacia*, *Pseudomonas* sp. EP-3, *Pseudomonas chlororaphis*, *Pseudomonas clemancea*, *P. collierea*, *P. fluorescens*, *P. putida*, *P. luteola*, *P. stutzeri* or *P. teessidea* (Abdel-Mawgoud, et al., 2010, supra). Where for example only an endogenous rhlA gene is desired to be included in the host cell various bacteria may be selected, of which *Serratia* sp. ATCC 39006 may serve as an illustrative example (Williamson, N. R., et al., Environmental Microbiology (2008) 10, 5, 1202-1217, see above for further examples).

The bacterial host cell may in some embodiments be of a phylum selected from Proteobacteria, Planctomycetes, Actinobacteria and Firmicutes. The host cell may for example be a *Pseudomonas* sp. proteobacterium of one of the classes Alphaproteobacteria, Betaproteobacteria, Gammaproteobacteria and Deltaproteobacteria. As a further example, the host cell may be an *Acidobacterium* of one of the classes Acidobacteriales and Solibacteres. The host cell may for instance be one of an *Acinetobacter* sp., *Enterobacter* sp., *Pantoea* sp., *Pseudomonas* sp, *Burkholderia* sp., *Myxococcus* sp., *Nocardioides* sp., *Pseudoxanthomonas* sp., *Methylobacterium* sp. and *Acidobacterium* sp. In some embodiments the bacterial host cell is gram-negative. The bacterial host cell of any one of the preceding claims, wherein said host cell is selected from the group consisting of *Pseudomonas putida*, *Pseudomonas chlororaphis*, *Pseudomonas fluorescens*, *Pseudomonas alcaligenes*, *Pseudomonas aeruginosa*, *Pseudomonas cepacia*, *Pseudomonas clemancea*, *Pseudomonas collierea*, *Pseudomonas luteola*, *Pseudomonas stutzeri*, *Pseudomonas teessidea*, *Escherichia coli*, *Renibacterium salmoninarum*, *Cellulomonas cellulans*, *Tetragenococcus koreensis*, *Burkholderia glumae*, *Burkholderia mallei*, *Burkholderia pseudomallei*, *Burkholderia plantarii*, *Burkholderia thailandensis*, *Acinetobacter calcoaceticus*, *Enterobacter asburiae*, *Enterobacter hormaechei*, *Pantoea stewartii* and *Pantoea ananatis*. In some embodiments the bacterial host cell is non-pathogenic for a human subject.

Where a heterologous Rhamnosyltransferase gene or a heterologous ortholog of a Rhamnosyltransferase gene is to be introduced into the bacterial host cell, this can be achieved using standard techniques known in the art, as also illustrated above. A heterologous Rhamnosyltransferase gene or a heterologous ortholog of a Rhamnosyltransferase gene may be selected from any desired species. As a few examples, a rhlA gene, or an ortholog thereof, may be from a bacterium of one of the classes Alphaproteobacteria, Betaproteobacteria, and Gammaproteobacteria. A rhlA gene, or an ortholog thereof, may for example be from a *Pseudomonas* sp., *Burkholderia* sp., *Enterobacter* sp., *Pantoea* sp., *Dickeya* sp., or *Pantoea* sp. It may for example be from a strain of *Renibacterium salmoninarum*, *Cellulomonas cellulans*, *Tetragenococcus koreensis* or *Acinetobacter calcoaceticus*. In some embodiments the rhlA gene is from one of *Burkholderia glumae*, *Burkholderia mallei*, *Burkholderia pseudomallei*, *Burkholderia plantarii*, *Burkholderia gladioli*, *Burkholderia ubonensis*, *Burkholderia ambifaria*, *Burkholderia cenocepacia*, *Burkholderia caryophylli*, *Dickeya zeae*, *Pseudomonas aeruginosa*, *Pseudomonas fluorescens*, *Pseudomonas putida*, *Pseudomonas oleovorans*, *Pseudomonas chlororaphis*, *Pantoea stewartii*, *Pseudomonas mendocina*, *Pseudomonas nitroreducens*, *Pseudomonas entomophila*, *Pseudomonas brassicacearum*, *Pseudomonas stutzeri*, *Pseudomonas fluorescens*, *Pseudomonas oleovorans*, *Pantoea ananatis*, *Serratia odorifera*, *Halothiobacillus neapolitanus*, *Enterobacter asburiae* and *Enterobacter hormaechei*. Other rhlaA/RhlA sequences are disclosed in WO 2012/013554 as enzymes "E1", "E1a", "E1b", "E1c", "E1d" or "E1e".

A rhlB gene, or an ortholog thereof, may be from a bacterium of one of the classes Alphaproteobacteria, Betaproteobacteria, Gammaproteobacteria, Planctomycetacia, Acidobacteriales and Solibacteres. A rhlB gene, or an ortholog thereof, may for example be from a *Pseudomonas* sp., *Burkholderia* sp., *Enterobacter* sp., *Pantoea* sp., *Dick-* eya sp., Blastopirellula sp., Pantoea sp., Methylobacterium sp., or Acidobacterium sp. In some embodiments the rhlB gene is from one of Pseudomonas aeruginosa, Burkholderia glumae, Burkholderia mallei, Burkholderia pseudomallei, Burkholderia thailandensis, Burkholderia ambifaria, Burkholderia cepacia, Burkholderia cenocepacia, Burkholderia gladioli, Dickeya dadantii, Pantoea ananatis, Planctomyces limnophilus, Blastopirellula marina, Methylobacterium extorquens, Methylobacterium chloromethanicum, Maritimibacter alkaliphilus, Acidobacterium capsulatum and Solibacter usitatus. Other rhlab/Rhlb sequences are disclosed in WO 2012/013554 as enzymes "E2", "E2a", "E2b", "E2c", "E2d" or "E2e".

A rhlC gene, or an ortholog thereof, may be from a bacterium of one of the classes Alphaproteobacteria, Betaproteobacteria, Gammaproteobacteria, Acidobacteriales, and Planctomycetacia. A rhlC gene, or an ortholog thereof, may for example be from one of Pseudomonas aeruginosa, Ralstonia solanacearum, Burkholderia glumae, Burkholderia pseudomallei, Burkholderia mallei, Burkholderia thailandensis, Burkholderia gladioli, Burkholderia cenocepacia, Burkholderia ambifaria, Burkholderia phytofirmans, Burkholderia phymatum, Burkholderia multivorans, Lautropia mirabilis, Variovorax paradoxus, Methylobacterium populi, Methylobacterium chloromethanicum, Methylobacterium extorquens, Methylotenera mobilis and Planctomyces maxis. The source of the rhlA gene, or the ortholog thereof, of the rhlB gene, or the ortholog thereof and, where present, of the rhlC gene, or the ortholog thereof are independently selected. In some embodiments the rhlA gene, or the ortholog thereof, and the rhlB gene, or the ortholog thereof, are from the same organism, e.g. the same species or the same strain. In some embodiments the rhlA gene, or the ortholog thereof, and the rhlB gene, or the ortholog thereof, are from different organisms, e.g. different species or different strains. The selection of the rhlA gene, or the ortholog thereof, and the rhlB gene, or the ortholog thereof, may affect the structure of the rhamnolipids produced by the bacterial host cell. Andrä et al. (Biol. Chem. (2006) 387, 301-310) and Hörmann et al. (Eur. J. Lipid Sci. Technol. (2010) 112, 674-680) have for example reported that B. plantarii, strains DSM 6535 and DSM 9509 produce a dirhamnolipid with two saturated 3-hydroxy-n-tetradecanoic acid fatty acid chains, whereas P. aeruginosa produces a dirhamnolipid with two saturated 3-hydroxy-n-decanoic acid fatty acid chains. An overview of the different structures of rhamnolipids that can be expected to be formed can be found in Abdel-Mawgoud et al. (2010, supra).

A bacterial host cell as defined above may be used in a method of producing one or more rhamnolipids. The bacterial host cell is cultured under conditions that allow rhamnolipid production. A variety of carbon source may be used such as a monosaccharide, e.g. glucose, a disaccharide, e.g. sucrose, an alcohol, e.g. glycerol, an alkane, e.g. n-hexane (see e.g. Christova, N., et al., Zeitschrift für Naturforschung (2004) 59c, 70-74), a fatty acid such as caprylic acid (also termed octanoate) or mixtures thereof. The bacterial host cell will typically be exposed to a fermentation process. The bacterial host cell may for instance be in the logarithmic growth phase or in the stationary phase.

In the method the rhamnolipid is recovered. Typically the rhamnolipid is secreted by the bacterial host cell, so that recovering the fermentation/culture medium includes recovering the rhamnolipid(s). Further the method may include enriching, isolating and/or purifying the rhamnolipid(s). The term "enriched" means that the rhamnolipid(s) constitute a significantly higher fraction of the total lipids and saccharides present in the solution of interest than in the solution from which it was taken. An enrichment may for instance include membrane filtration, for example for clarification, buffer exchange or concentration purposes. It may also include filtration or dialysis, which may for instance be directed at the removal of molecules below a certain molecular weight, or a precipitation using organic solvents or ammonium sulphate. Chromatography may for example be carried out in the form of a liquid chromatography such as capillary electrochromatography, HPLC (high performance liquid chromatography) or UPLC (ultrahigh pressure liquid chromatography) or as a gas chromatography. The chromatography technique may be a process of column chromatography, of batch chromatography, of centrifugal chromatography or a method of expanded bed chromatography, as well as electrochromatographic, electrokinetic chromatography. It may be based on any underlying separation technique, such as adsorption chromatography, hydrophobic interaction chromatography or hydrophobic charge induction chromatography, size exclusion chromatography (also termed gel-filtration), ion exchange chromatography or affinity chromatography and may also be a method of capillary gas chromatography. Another example of a purification is an electrophoretic technique, such as preparative capillary electrophoresis including isoelectric focusing. Examples of electrophoretic methods are for instance free flow electrophoresis (FFE), polyacrylamide gel electrophoresis (PAGE), capillary zone or capillary gel electrophoresis. An isolation may include may include the combination of similar methods.

The present invention also relates to a recombinant nucleic acid molecule, including a vector, that includes 5' to 3', a promoter effective to initiate transcription in a host cell and the sequence of a rhlA gene and/or a rhlB gene. In some embodiments a single nucleic acid molecule encodes both the rhlA gene and the rhlB gene. In some embodiments a first nucleic acid molecule encodes the rhlA gene and a second nucleic acid molecule encodes the rhlB gene. In some embodiments a third nucleic acid molecule encodes a rhlC gene. In some embodiments a single nucleic acid molecule encodes the rhlA gene, the rhlB gene and a rhlC gene. Such a nucleic acid molecule includes a transcriptional region functional in a bacterial host cell and a transcriptional termination region functional in a bacterial host cell. The above-described molecules may be isolated and/or purified nucleic acid, e.g. DNA molecules.

A host cell according to the invention may also be used as a bacterial non-toxic insecticide against insect pests on crops on the basis of the rhamnolipids formed (Kim, S. K., et al., J. Agric. Food Chem. (2011) 59, 934-938). Rhamnolipids are able to penetrate the cuticle membrane of insects, which has been shown to cause aphid death. A host cell according to the invention may also be used as a non-toxic antimycelial or antifungal agent (Abalos, A., et al., Langmuir (2001) 17, 1367-1371), for example against fungus-caused damping-off (cf. Sharma, A., et al., J. Nat. Prod. (2007) 70, 941-947). A host cell according to the invention may also be used to provide rhamnolipids for a variety of applications, such as obtaining or maintaining cleanness of a surface such as a surface of any desired device or a body surface, e.g. skin or hair, increasing the stability of dough or batter, to improve microbial conservation of a baked product (see WO 2004/040984), to deodorize the skin or in producing a cream, ointment, emulsion, powder, lotion, gel, mist, spray or shampoo for cleaning purposes (e.g. WO 2008/013899), treatment of wounds, injuries, skin conditions, organ repairs, increasing the structure and tensile strength of the skin (WO 2011/056871). A host cell according to the invention may also be used in destruction of oil and oil products, including crude oil and petroleum or polycyclic aromatic hydrocarbons (Vetrova, A. A., et al., Microbiology (Pleiades Publishing) (2007) 76, 3, 310-316).

As noted above, in some embodiments a method of producing a rhamnolipid according to the invention includes culturing a host cell at a temperature above 30° C. in a suitable medium. Any medium may be used that is suitable to sustain cell viability and in which the selected host cell is capable of producing a rhamnolipid, as explained above. Any suitable cell may be used in such a method, as long as the cell has a rhlA gene, or an ortholog thereof, and a rhlB gene, or an ortholog thereof. In some embodiments the host cell is a cell as defined above. In some embodiments in the cell may at least one of the rhlA gene, or the ortholog thereof, and the rhlB gene, or the ortholog thereof, are under the control of a heterologous promoter. In a respective method the host cell is allowed to produce the rhamnolipid. Allowing the host cell to produce the rhamnolipid may include allowing the host cell to secrete the rhamnolipid. As explained above, the rhamnolipid may be recovered. In some embodiments the rhamnolipid may be isolated (supra).

Thus far, apart from Pseudomona aeruginosa, Pseudomona strains applied or tested for the production of rhamnolipids, i.e., non-pathogenic Pseudomonas strains have been cultured at temperatures below or at 30° C. (see Ochsner et al., Cha et al., and Trummler et al.), while Pseudomonas aeruginosa or also a modified Escherichia coli strain was cultured at a temperature of about 37° C. It was assumed that a temperature at or below 30° C. is optimal for non-pathogenic Pseudomonas strains, since this temperature, so to say, reflects the temperature which usually surrounds such bacteria, i.e., is present in their natural habitats. However, the present inventors have surprisingly found that host cells, in particular non-pathogenic host cells producing rhamnolipids such as Pseudomonas strains, for example, those described herein, produce rhamnolipids at temperatures above 30° C. in even larger amounts than at a temperature at or below 30° C. This surprising finding has advantageous implications. As fermentations are an exothermic process, the fermenter (reactor) requires cooling to ensure constant and optimal conditions for growth of the bacteria. Accordingly, the lower the temperature of the reactor, the more energy is required for cooling. Yet, increasing the temperature should lead to declining cooling demands, as the difference of the temperature of the cooling medium and reactor also increases. Hence, less cooling medium such as water would be required to withdraw the same amount of heat from the fermentation process. The present inventors made therefore experiments that go against the established and usually applied set-up of growing host cells capable of producing rhamnolipids and cultured these host cells at temperatures above 30° C. Strikingly, the present inventors did not only find that host cells, in particular non-pathogenic host cells producing rhamnolipids do grow at temperatures above 30° C., they also found that non-pathogenic bacteria producing rhamnolipids produce even more rhamnolipids at temperatures above 30° C. Thus, the finding of the present inventors does not only aid in saving energy, thereby rendering the production of rhamnolipids cheaper, but also in increasing the yield of rhamnolipids produced (producible) by non-pathogenic host cells capable of producing rhamnolipids.

The temperature applied in a method of producing a rhamnolipid comprising culturing a host cell at a temperature in a suitable medium and allowing the host cell to produce the rhamnolipid, wherein the host cell comprises a rhlA gene, or an ortholog thereof, and a rhlB gene, or an ortholog thereof, is above 30° C.

In other embodiments, the temperature applied in the methods of the present invention may also be about or at temperature of 31° C., 32° C., 33° C., 34° C., 35° C., 36° C. or 37° C., with about or at a temperature of 32° C., 33° C. or 34° C. being preferred. A temperature about or at 33° C. is even more preferred.

Alternatively, the temperature may be in a range of more than (>) 30° C.-37° C., 30° C.-36° C., 30° C.-35° C., 30° C.-34° C., 30° C.-33° C., 30° C.-32° C., 30° C.-31° C., with a range of more than (>) 30° C.-35° C., 30° C.-34° C., 30° C.-33° C. being preferred.

In a yet further alternative, the temperature may be in a range of 31° C.-37° C., 31° C.-36° C., 31° C.-35° C., 31° C.-34° C., 31° C.-33° C., 31° C.-32° C., with a range of 31° C.-35° C., 31° C.-34° C., 31° C.-33° C. being preferred.

The above explanations, for example on embodiments of cells or of the method, apply mutatis mutandis to the present method. In some embodiments the host cell used may for example be non-pathogenic.

Additional objects, advantages, and features of this disclosure will become apparent to those skilled in the art upon examination of the following examples thereof, which are not intended to be limiting. Thus, it should be understood that although the present disclosure is specifically disclosed by exemplary embodiments and optional features, modification and variation of the disclosures embodied therein herein disclosed may be resorted to by those skilled in the art, and that such modifications and variations are considered to be within the scope of this disclosure.

Items of the Invention

The present invention can also be characterized by the following items:

1. A host cell comprising
   (i) a rhlA gene or an ortholog thereof, being under the control of a heterologous promoter; and
   (ii) a rhlB gene or an ortholog thereof, being under the control of a heterologous promoter
   wherein said host cell is capable of achieving a carbon yield of more than 0.18 Cmol rhamnolipid/Cmol substrate.
2. The host cell of item 1, wherein the bacterial host cell further comprises a rhlC gene or an ortholog thereof, being under the control of a heterologous promoter.
3. The host cell of item 1 or 2, being a prokaryotic host cell or a yeast host cell.
4. The host cell of any one of the preceding items, wherein the host cell is incapable of producing poly(3-hydroxyalkanoates) (PHA).
5. The host cell of item 4, having a knock-out mutation in an endogenous sequence encoding poly(3-hydroxyalkanoic acid) synthase 1.
6. The host cell of any one of the preceding items, wherein the host cell is non-pathogenic for a human subject.
7. The host cell of any one of the preceding items, wherein the host cell is selected from the group consisting of Pseudomonas putida, Pseudomonas chlororaphis, Pseudomonas fluorescens, Pseudomonas alcaligenes, Pseudomonas aeruginosa, Pseudomonas cepacia, Pseudomonas clemancea, Pseudomonas collierea, Pseudomonas luteola, Pseudomonas stutzeri, Pseudomonas teessidea, Escherichia coli, Renibacterium salmoninarum, Cellulomonas cellulans, Tetragenococcus koreensis, Burkholderia glumae, Burkholderia mallei, Burkholderia pseudomallei, Burkholderia plantarii, Burkholderia thailandensis, Acinetobacter calcoaceticus, Enterobacter asburiae, Enterobacter hormaechei, Pantoea stewartii and Pantoea ananatis.
8. The host cell of any one of the preceding items, wherein said one or more rhamnolipids comprise a mono-rhamnolipid and/or a di-rhamnolipid.
9. The bacterial host cell of any one of the preceding items, wherein the one or more rhamnolipids comprise a fatty acid having a main chain comprising about six to about 18 carbon atoms.
10. The host cell of item 9, wherein the fatty acid is one of 3-hydroxy-n-octanoic acid, 3-hydroxy-n-octenoic acid, 3-hydroxy-n-octadienoic acid, 3-hydroxy-n-decanoic acid, 3-hydroxy-n-decenoic acid, 3-hydroxy-n-dodecanoic acid, 3-hydroxy-n-dodecenoic acid, 3-hydroxy-n-dodecadienoic acid, 3-hydroxy-n-tetradecanoic acid, 3-hydroxy-n-tetradecenoic acid, 3-hydroxy-n-tetradecadienoic acid, 3-hydroxy-n-hexadecanoic acid and 3-hydroxy-n-octadecanoic acid.
11. A method of producing a rhamnolipid, the method comprising
    (a) culturing a host cell according to any one of items 1-10 under conditions allowing rhamnolipid production;
    (b) recovering said rhamnolipid; and optionally
    (c) isolating said rhamnolipid.
12. The method of item 11, wherein the host cell is cultured at a temperature above 30° C.
13. A method of producing a rhamnolipid, the method comprising culturing a host cell at a temperature above 30° C. in a suitable medium and allowing the host cell to produce the rhamnolipid, wherein the host cell comprises a rhlA gene, or an ortholog thereof, and a rhlB gene, or an ortholog thereof.
14. The method of item 13, wherein the host cell is non-pathogenic.
15. A rhamnolipid preparation obtainable by the method of any one of items 11-14, said preparation comprising rhamnolipids having more than 80% (w/w) fatty acids of one of 3-hydroxy-n-octanoic acid, 3-hydroxy-n-decanoic acid, 3-hydroxy-n-decanoic acid, 3-hydroxy-n-dodecanoic acid, 3-hydroxy-n-tetradecanoic acid, 3-hydroxy-n-hexadecanoic acid and 3-hydroxy-n-octadecanoic acid.

EXAMPLES

A: Production of *Pseudomonas aeruginosa* Rhamnolipids in *Pseudomonas putida* KT2440
Materials and Methods
Bacterial Strains, Culture Conditions and Plasmids
The used bacteria strains *Pseudomonas aeruginosa* PAO1 (Hancock, R. E., & Carey, A. M., J. Bacteriol. (1979) 140, 902-910), *Pseudomonas putida* KT2440 (Nelson, K. E., et al., Environmental Microbiology (2002) 4, 12, 799-808; Ramos-Diaz, M. A., & Ramos, J. L., Journal of Bacteriology (1998) 180, 23, 6352-6363), *Escherichia coli* DH5α (Hanahan, D., Journal of Molecular Biology (1983) 166, 4, 557-580), *Bacillus subtilis* TEB1030 (Eggert, T., et al., FEBS Letters (2001) 502, 3, 89-92) and *Corynebacterium glutamicum* ATCC 13032 (Kalinowski, J., et al., J Biotechnol (2003) 104, 1-3, 5-25) were routinely cultivated in LB-medium (10 g/L tryptone, 5 g/L yeast extract, 10 g/L NaCl) at 37° C. and 30° C. for *P. putida* and *C. glutamicum* respectively. *P. putida* and *E. coli* containing the vector pVLT33 (Lorenzo et al. 1993a) and derivatives thereof were selected by adding 50 µg/mL kanamycine to LB-agar and liquid cultures. For selecting pVLT31 and derivates tetracycline with concentrations of 10 µg/L for recombinant *E. coli* and 25 µg/L for recombinant *P. putida* were added. Rhamnolipid production with *P. aeruginosa* and recombinant *P. putida* was carried out using LB-medium complemented with 10 g/L glucose.

Rhamnolipid Toxicity Determination
The experiments were carried out in the semiautomated BioLector 31 using 48 well Flowerplates (m2p-Labs, Aachen, Germany). The biomass concentration was quantified by online light scattering. All bacteria apart from *P. putida* KT2440 were cultivated in 800 µL to 1000 µL TB-medium. *P. putida* was grown in KT2440 in 500 µL LB-medium supplemented with 10% glucose and 90 mM potassium phosphate buffer (pH 7.4). The growth medium contained rhamnolipid concentrations between 0 g/L and 90 g/L. The cultures were shaken at 1,100 to 1,200 rpm and incubated at 37° C. or 30° C., for *E. coli* DH5α, *B. subtilis* TEB1030 and *C. glutamicum* ATCC13032 and *P. putida* KT2440, respectively.

Construction of the Rhamnolipid Production Module
The rhlAB operon was amplified from the genomic DNA of *P. aeruginosa* PAO1 that was isolated with the DNeasy Blood and Tissue Kit from QIAGEN (Hilden, Germany), using PfuTurbo DNA polymerase (Stratagene, Waldbronn, Germany) as described by the supplier. The used primer had the following sequences: sense 5'TTGAATTCCATCGGC-TACGCGTGAACACGG'3 (SEQ ID NO: 10), antisense 5'TTTTTCTAGATCAGGACGCAGCCTTCAGCC'3 (SEQ ID NO: 11). The oligonucleotides were obtained from Eurofins MWG Operon (Ebersberg, Germany). The rhlAB PCR product was digested with EcoRI/Acc65I and subsequently ligated into pVLT33, which was digested with the same enzymes, creating the plasmid pRL1. Restriction enzymes and T4 DNA ligase were obtained from Fermentas (St. Leon-Rot, Germany) and used as recommended. DNA manipulation was carried out according to standard procedures. Ligations were transformed into competent *E. coli* DH5α using a standard protocol (Hanahan, D., Journal of Molecular Biology (1983) 166, 4, 557-580). Transformed cells were selected on LB-agar plates containing 50 µg/mL kanamycine. Experiments with the kanamycine resistant single gene deletion strain *P. putida* KT42C1, lacking the poly(3-hydroxyalkanoic acid) synthase 1 encoded by phaC1, required subcloning of rhlAB into pVLT31, which contains a gene for tetracycline resistance.

Construction and Analysis of Rhamnolipid Producing *P. putida*
*P. putida* KT2440 was transformed using electroporation as described by Choi et al., Journal of Microbiological Methods (2006) 64, 391-397). Cells containing plasmid pVLT33 or the derivate pRL1 were selected on LB-Agar plates or liquid cultures containing 50 µg/mL kanamycine. For the production of rhamnolipids a main culture of 50 mL LB-medium supplemented with 1% glucose and 50 µg/mL kanamycine in a 500 mL Erlenmeyer flask was inoculated from a starter culture and incubated at 30° C. and 200 rpm. The expression of rhl genes was induced by adding IPTG (isopropyl β-D-1-thiogalactopyranoside) to a final concentration of 0.4 mM from the beginning of the fermentation. Rhamnolipids were extracted 24 h after induction.
*P. aeruginosa* was cultivated in 10 mL phosphate-limited protease peptone-glucose-ammonium salt medium (PPGAS, pH 7.2), which promotes the production of rhamnolipids (Wild, M., et al., FEMS Microbiology Letters (1997) 153, 2, 279-285), containing 5 g/L glucose, 10 g/L peptone 0.02 M $NH_4Cl$, 0.02 M KCl, 0.12 M Tris-HCl, and 0.0016 M $MgSO_4$. After 24 h at 37° C., with an agitation of 150 rpm, rhamnolipids were harvested.

Cultivations of *P. putida* KT2440 rhlAB carried out in order to supply rhamnolipid-characterization via thin layer chromatography (TLC) and HPLC-ESI-MS featured slightly different process parameters. Only 10 ml of LB-Medium, supplemented with 10 g/L glucose and 50 µg/mL kanamycine in a 100 mL Erlenmeyer flask, were inoculated with an $OD_{580}$ of 0.05 from a starter culture and incubated at 30° C. and 150 rpm. IPTG was added to a final concentration of 0.4 mM at an $OD_{580}$ of 0.5.

Rhamnolipid Production

The scale-up of rhamnolipid production was tested in a 3.2-liter fermenter vessel (KLF 2000, Bioengineering AG, Wald, Switzerland) with a working volume of 2 liters. The fermenter contains two 6-blade turbine stirrers, a temperature control, and a pH gas inlet. The operating conditions were set to pH 6.8 and a temperature of 30° C., a constant gassing rate of 0.5 vvm and a stirrer speed in the range from 300 to 900 rpm depending on the online-determined $pO_2$ signal. Additional glucose was fed using a peristaltic pump.

Quantification of Rhamnolipids

For analysis, rhamnolipids were extracted using 100 µL (for orcinol-assay) and 500 µL (for TLC) of cell-free culture broth and 500 µL of ethyl acetate. Samples were mixed by vortexing, with a subsequent phase separation by centrifugation in a tabletop centrifuge at maximum speed (30 sec). The upper, rhamnolipid-containing phase was transferred to a new reaction tube. This procedure was repeated three times. Finally, the organic solvent was removed by evaporation in a vacuum centrifuge.

Thin Layer Chromatography of Rhamnolipids

For detection of rhamnolipids using TLC, the dried rhamnolipids were dissolved in 10 µL ethanol. 5 µL of this solution were spotted on a silica 60 TLC-plate (Macherey-Nagel, Dueren, Germany). In addition, 5 µL of a 0.1% rhamnolipid standard (JBR425, Jeneil Biosurfactant Co., LCC, Saukville, USA) containing mono- and di-rhamnolipids were spotted. The running buffer was a mixture of chloroform, methanol and acetic acid in a ratio of 65:15:2, respectively. To visualize the rhamnolipids on the TLC-plates, the plates were covered with a detection agent consisting of 0.15 g orcinol, 8.2 mL sulfuric acid, and 42 mL deionized water. For preservation, dried plates were incubated at 110° C. for 10 min.

Rhamnolipid Quantification Using Orcinol Assay

The total amount of rhamnolipids was measured using the standard orcinol assay (see also below). The evaporated rhamnolipids were dissolved in 100 µL deionized water. Subsequently 100 µL orcinol solution (1.8% orcinol in deionized water) and 800 µL sulphuric acid (60%) were added. The samples were incubated at 80° C. for 30 min and 1000 rpm orbital shaking in a thermomixer (Eppendorf AG, Hamburg, Germany). After cooling to room temperature, the samples were measured at 421 nm in comparison to different concentrations of a rhamnolipid standard (JBR425, Jeneil Biosurfactant Co., LCC, Saukville, USA) using a Genesys 10 UV spectrophotometer (Thermo Fisher Scientific, Waltham, USA).

Rhamnolipid Quantification Using RP-HPLC-CAD

Culture samples were centrifuged at 17,700×g for 30 minutes. 100 µL supernatant were added to 900 µL deionized water, mixed on a vortex shaker, and analyzed on a isocratic reversed phase LaChrome HPLC system (VWR-Hitachi, Darmstadt, Germany). The system was equipped with an integrated Luna C8(2) silica based column (4.6×150 mm, 5µ, 100 Å) by Phenomenex, Inc. (Torrance, Calif., USA) and a corona charged aerosol detector (ESA Biosciences Inc., MA, USA). The sample volume was set to 20 µL. The sample was eluted at a flow rate of 800 µL per minute with a mixture of 80% methanol, 19.8% deionized water and 0.2% tetrafluoroacetic acid.

Rhamnolipid Composition Characterization by HPLC-ESI-MS

High performance liquid chromatography electrospray ionization mass spectrometry (HPLC-ESI-MS) was used for rhamnolipid characterization (Central Division of Analytical Chemistry/BioSpec, Forschungszentrum Jülich, Jülich, Germany). Rhamnolipids were extracted from 1 L culture broth (5 L Erlenmeyer flask) as described by Déziel et al. (1999) with small modifications. Cells were removed by centrifugation for 30 min at 9000×g and 10° C. The supernatant was acidified with 37% HCL to a pH of 3 and incubated overnight at 4° C. The precipitated rhamnolipids were recovered by centrifugation (9000×g, 45 min, 4° C.) and dissolved in 15 mL acidified water (pH 3). This solution was extracted three times with 15 mL ethyl acetate. The combined organic phases were evaporated in a vacuum centrifuge. The residue was dissolved in 15 mL of 0.05 M NaHCO3, acidified to pH 2 with 37% HCl and incubated overnight at 4° C. The precipitate was finally recovered by centrifugation for 60 min at 13,000×g and 4° C.

For characterization, an Agilent 1100 series binary HPLC system (Agilent Technologies, Waldbronn, Germany), assembled with a diode array detector (DAD) (190-400 nm), coupled with a triple quadrupole 4000QTRAP™ mass spectrometer (Applied Biosystem/MDS SCIEX, Foster City, Calif., USA) assembled with a turbo ion spray source was used.

For rhamnolipid separation, a ProntoSIL 120-C8-SH (Bischoff Chromatography, Leonberg, Germany) column (150×2 mm i.d., 3 µm particle size) was used at 20° C. The gradient elution was done with deionized water with 0.1% formic acid (solvent A) followed by different concentrations of acetonitrile with 0.1% formic acid (solvent B). The elution started with 60% B isocratic for 4 min, from 4 to 24 min a linear increase from 60% B to 90% B was applied, subsequently followed by a second isocratic step (90% B for 10 min) and ended by a return to 60% B in one min. The re-equilibration was done with 60% B isocratic for 10 min. All steps were performed at a constant flow rate of 300 µL/min. The injection volume was 20µL.

The MS was used in negative enhanced mass spectrum (EMS) mode scanning from 200-1000 Da. A flow injection analysis (FIA) with a standard was used at first to optimize the following parameters: IS −4500 V, declustering potential (DP) −100 V, curtain gas ($N_2$) 10 arbitrary units (au), source temperature 500° C., nebulizer gas ($N_2$) 50 au, and heater gas ($N_2$) 20 au. Collision Energy (CE) and third quadrupole (Q3)-entry barrier were set to −5 V and 8 V, respectively. The negative enhanced product ion (EPI) scan mode was used for structural elucidation MS/MS experiments, in which product ions are generated in the second quadrupole (Q2) by collision-activated dissociation of selected precursor ions of the first quadrupole (Q1) and mass analyzed in a linear ion trap. The CE ranged from 30 to 70 V.

The di-rhamnolipid standard (Rha-Rha-$C_{10}$-$C_{10}$) for HPLC analysis was a gift from Sanofi-Aventis Deutschland GmbH, former Hoechst AG (Frankfurt, Germany). Monorhamnolipid standard (Rha-$C_{10}$-$C_{10}$) was prepared as described before (Trummler et al. 2003).

Rhamnolipid Purification by Adsorption

The medium was centrifuged in 200 mL cups for 60 min at 4000 rpm (5810R Eppendorf AG, Hamburg, Germany) to remove cells and cell debris. The cell-free medium was loaded with five times the bed volume per hour by a peristaltic pump (MP-3 Micro Tube Pump, Eyela Inc., Tokyo, Japan) as specified by the manufacturer to a column packed with 90 g of conditioned Amberlite XAD-2 resin (GE Healthcare). After washing with bidistilled water, rhamnolipids were eluted with 99% isopropanol using a continuous flow (HPLC pump 114M, Beckman Coulter, Inc., Brea, USA). The organic solvent was evaporated in a freeze dryer (Alpha 1-5, Martin Christ Gefriertrocknungsanlagen GmbH, Osterode am Harz, Germany).

Theoretical Capacity Estimation

The flux balance analysis was carried out using the software Insilico Discovery (version 3.2.0, Insilico Biotechnology AG, Stuttgart, Germany). The provided metabolic network used for simulations was modified to represent the reaction network of *P. putida* (Appendix X).

The following reactions were added to the *P. putida* model:

α-D-Glucose-1-phosphate+NADPH+H⁺+
    dTTP ⇒ dTDP-L-rhamnose+PP$_i$+NADP⁺+H$_2$O     (A)

2β-3-hydroxydecanoyl-ACP+H$_2$O ⇔ β-3-hydroxydecanoyl-β-3-hydroxydecanoate+2ACP     (B)

dTDP-L-rhamnose+β-3-hydroxydecanoyl-β-3-hydroxydecanoate ⇔ rhamnosyl-β-3-hydroxydecanoyl-β-3-hydroxydecanoate+dTDP     (C)

A linear optimization for rhamnolipid-production with simultaneous minimization of total fluxes was carried out. The rhamnolipid production rate was simulated with different carbon substrates (glucose, glycerol, sucrose, and octanoate). To ensure comparability of the results, the inventors chose the unit Cmol, which normalizes the rhamnolipid production rate to the amount of carbon atoms present in the carbon substrate. The substrate uptake was varied between 0 and 120 mCmol/($g_{CDW}$ h). The maintenance metabolism, characterized through the simple reaction of ATP to ADP, was varied in the range of 0 to 50 mmol/($g_{CDW}$ h). Blank et al. (2008) described a value for the non growth-associated maintenance of 10.2 mmol ATP/($g_{CDW}$ h) for *P. putida* DOT-T1E. The considerably higher upper limit of 50 mmol ATP/($g_{CDW}$ h) accounts for scenarios of extra stress, e.g., for metabolic cost of handling high rhamnolipid concentrations. The chosen values for the growth rates were 0 l/h, 0.4 l/h and 0.8 l/h, reflecting ideal production condition, growth observed during rhamnolipid production, and maximal growth of *P. putida* on glucose (Castillo and Ramos 2007). Additionally all occurring fluxes were limited to a maximal value of 120 mCmol/($g_{CDW}$ h). Furthermore, variation of the fluxes through the pathways ED pathway, TCA cycle, and PP pathway were examined. In addition, an alternative glucose uptake system, the phosphotransferase system, and a complemented EMP pathway (insertion of a phosphofructokinase reaction for example encoded on a fructose utilization operon by fruK (PP0794), catalyzing the conversion of glucose-6P to glucose-1,6P) were simulated.

Determination of Fermentation Kinetics

The growth kinetic could be described mathematically using a logistic growth model. Logistic growth of pseudomonads had been previously reported for rhamnolipid producing wild type *P. aeruginosa* growing on sunflower oil (Müller, M. M., et al., Applied Microbiological Biotechnology (2010) 87, 1, 167-174).

The biomass concentration X was described using equation 1, where $X_0$ is the initial biomass concentration, $X_{add}$ the additional biomass concentration, $t_0$ the time after which half of $X_{add}$ is formed, and b is a curve form coefficient.

$$X(t) = X_0 + \frac{X_{add}}{1 + \left(\frac{t}{t_0}\right)^b} \quad (1)$$

The experimental data for the rhamnolipid and glucose concentrations could be described with equations 2 and 3, where $r_{RL}$ is the specific rhamnolipid production rate [g RL/$g_{CDW}$ h] and $r_{Glucose}$ is the specific glucose uptake rate [g Glucose/$g_{CDW}$ h].

$$\frac{dc_{RL}}{dt} = r_{RL} \cdot X \quad (2)$$

$$\frac{dc_{Glucose}}{dt} = r_{Glucose} \cdot X \quad (3)$$

A multivariable least squares fit was used to illustrate the development of all three fermentation parameters depending on each other.

Results

High Rhamnolipid Resistance as Prerequisite for the Production Host

The non-pathogenic host for rhamnolipid production from glucose has to withstand high rhamnolipid concentrations to sustain industrially relevant production titers. The industrial workhorses *Escherichia coli*, *Bacillus subtilis*, and *Corynebacterium glutamicum*, as well as the closely related, but non-pathogenic *Pseudomonas*, *Pseudomonas putida* were tested for resistance against di-rhamnolipids. Using a semi-automated microbioreactor platform, the BioLector (m2p-Labs, Aachen, Germany), the rate of growth of the species were monitored in the presence of up to 90 g/L di-rhamnolipids (purity of 95%, FIG. 2). The true inhibitory concentrations are difficult to determine, as foam formation decreases reliability of the determined growth rates at very high rhamnolipid concentrations.

The effect of rhamnolipids on Gram-positive *C. glutamicum* is dramatic, where concentrations of less than 100 mg reduce the rate of growth by 60% (FIG. 2D). *B. subtilis* on the other hand, being Gram-positive as well, features only slightly decreased growth rates, while the duration of the lag-phase increases significantly in the presence of rhamnolipids (FIG. 2B). *B. subtilis* excretes lipases, which might be able to disassemble di-rhamnolipid, by splitting off the fatty acids from the sugar molecules, reducing the toxic effect significantly. Then, *B. subtilis* is able to grow unaffected by the rhamnolipids derived residues, which explains the elongated lag-phase and the almost unimpaired growth rates. Possible candidates that might digest extracellularly rhamnolipids are the enzymes lipoyl synthase (EC 2.8.1.8) and triacylglycerol lipase (EC 3.1.1.3), being products of lipA and lipB, respectively (Eggert, T, et al. FEBS Lett (2001) 502, 3, 89-92)

In contrast, Gram-negative species appear to be less affected and can grow in the presence of high concentrations of rhamnolipids. At a concentration of 90 g/L di-rhamnolipids *E. coli* only grows with half the growth rate it features when growing in absence of rhamnolipids (FIG. 2E). Importantly, the GRAS classified *P. putida* KT2440 (Timmis 2002) showed little change in the rate of growth in dependence of rhamnolipid concentration as high as 90 g/L (data not shown). As this strain is closely related to *P. aeruginosa* and contains both necessary pathways for rhamnolipid precursor synthesis (i.e., de novo lipid synthesis, activated rhamnose) (Nelson K. E., et al., Environ Microbiol (2002) 4, 12, 799-808) and grows with a very high rate on glucose (Blank, L. M., et al., FEBS Journal (2008) 275, 5173-5190), *P. putida* KT2440 was chosen as host for rhamnolipid production using glucose as carbon source.

Blueprint of an Optimal Metabolic Network for Rhamnolipid Production

Having the chassis in hand, the design of a metabolic network with high capacity for rhamnolipid synthesis in *P. putida*, using flux balance analysis with the rate of rhamnolipid production as linear programming objective, was in focus. The constraints of the metabolic network were, besides its structure, the substrate uptake rate, the rate of biomass formation, and cell maintenance.

Figure 3B:
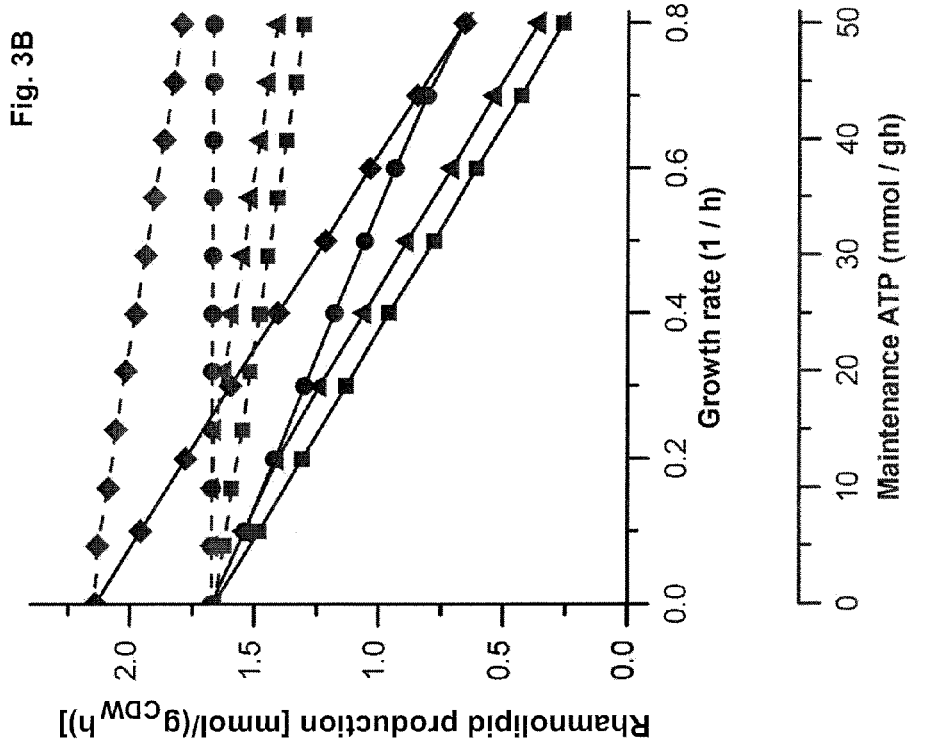
FIG. 3B shows rhamnolipid production as a function of biomass formation and maintenance metabolism for different carbon substrates. Squares represent the course of rhamnolipid production for glucose uptake (■), circles for glycerol (●), triangles represent sucrose (▲) and diamonds octanoate (♦). Black curves depict rhamnolipid production plotted against the rate of growth; grey dashed curves depict rhamnolipid production plotted against maintenance metabolism.

The theoretically achievable yields of rhamnolipids on industrial relevant substrates (glucose, sucrose, glycerol, and octanoate) were estimated. The computational results indicate that cell growth should be minimized to achieve high rhamnolipid yields (FIG. 3B). Without growth and no or low cell maintenance, rhamnolipid yields varied only slightly between the two sugars and glycerol. The choice of substrate had an effect during growth or high cell maintenance metabolism. Specifically, sucrose and glycerol were superior to glucose, as the glucose ABC-transporter requires one ATP per glucose transported, while glycerol is transported via an ion channel by diffusion (Hervas, A. B., et al., J Bacteriol (2008) 190, 1, 416-420; Nelson et al., 2002, supra). *P. putida* does not feature a sucrose uptake system, which therefore has to be established; utilizing a sucrose porin channel (Van Gelder, P., et al., Protein Eng (2001) 14, 11, 943-948) present in some *P. syringae* strains (Buell, C. R., et al., Proc Natl Acad Sci USA (2003) 100, 18, 10181-10186; Joardar, V., et al., J Bacteriol (2005) 187, 18, 6488-6498), would yield in a non-cellular energy consuming sucrose uptake. Octanoate enabled the highest yield (FIG. 2B). Octanoate requires only activation by ACP to form HAA (see FIG. 3A), thereby avoiding metabolic expensive de novo lipid synthesis. The rhamnose moiety requires β-oxidation and gluconeogenic reactions.

Notably, with low growth rates and maintenance metabolism, rhamnolipid yield on glycerol equaled yields on sugars; with higher growth rate and maintenance metabolism, the yield on glycerol equaled the yield on octanoate.

Figure 3A:
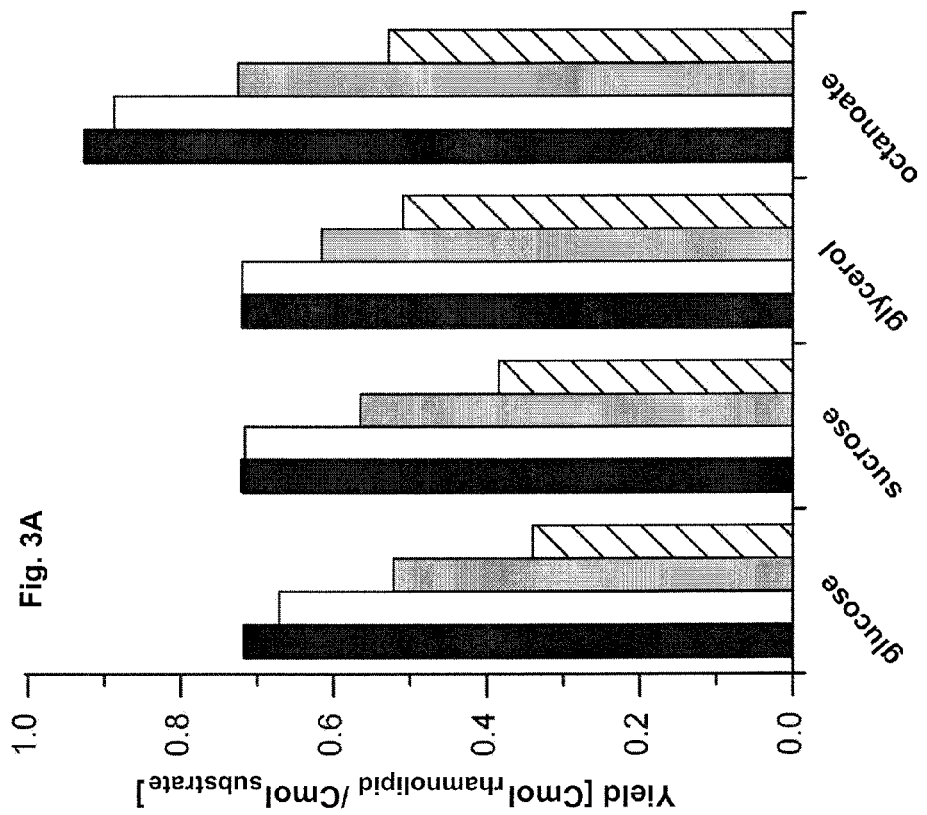
FIG. 3A shows rhamnolipid yields using different carbon substrates. Yields were calculated for zero growth (black bars), zero growth and 30 mmol ATP/($g_{CDW}$ h) maintenance metabolism (white bars), growth at a rate of 0.4 l/h with 30 mmol ATP/($g_{CDW}$ h) maintenance metabolism (gray bars), and a growth rate of 0.8 l/h with 50 mmol/($g_{CDW}$ h) maintenance metabolism (shaded bars). The substrate uptake rates were constrained to 180 mCmol/($g_{CDW}$ h).

This observation suggests that rhamnolipid production by non-growing cells is carbon limited, while production by growing cells can be energy limited. Glycerol feeds into central carbon metabolism at the level of glyceraldehyde-3-phosphate and thus does not utilize the pentose phosphate (PP) pathway, which squanders carbon via $CO_2$ production (FIG. 3A). Glucose and sucrose enter central carbon metabolism via the Entner-Doudoroff (ED) pathway. To supply the cell with the necessary energy for maintenance (via redox cofactor synthesis), the PP pathway was active, hence wasting carbon via $CO_2$ formation. In scenarios with very high energy demand (i.e., high growth rates and/or high maintenance metabolism), full oxidation via acetyl-CoA and the tricarboxylic acid (TCA) cycle was observed, again resulting in $CO_2$ formation and concomitant lowering of the rhamnolipid yield. The high rhamnolipid yield on octanoate is a result of the omitted reaction from pyruvate to acetyl-CoA (via the pyruvate dehydrogenase).

In summary, the carbon substrates used for rhamnolipid production by *P. aeruginosa* are theoretically ideal for achieving high yields of product. However, the cumbersome product purification from a second, hydrophobic phase is not desirable. The inventors therefore favor the industrially important carbon source glucose. It is desirable to produce rhamnolipids from glucose with a host that has low maintenance requirements and forms no side-product. Ideally such a host allows production during non-growth conditions, to maximize the yield of product on substrate.

Having the carbon substrate defined, subsequent simulations focused on a metabolic network that is optimal for rhamnolipid production from glucose. Possible reaction candidates include glucose uptake and glucose catabolism. The earlier via a newly introduced phosphotransferase system to improve the stoichiometry of glucose uptake and the latter via an artificial Embden-Meyerhof-Parnas (EMP) pathway by introducing a phosphofructokinase to improve ATP generation by substrate level phosphorylation, respectively. Notably, the improvements of the tested scenarios were minor (below 1% of additional rhamnolipid), again highlighting that carbon and not energy availability determines the yield of rhamnolipid production. Hence, these optimizations were not considered as valuable targets for improvement of rhamnolipid production. Instead, removing enzymatic reactions that are not necessary for rhamnolipid production, but potentially waste carbon moved into focus. As already mentioned, no side products were observed in the growth medium. Therefore, the avoidance of biomass components that are not necessary for survival and production are the only means for metabolic optimization. One such target is the storage polymer PHA.

Rhamnolipid Production from Glucose by Non-Pathogenic *P. Putida*

Figure 4:
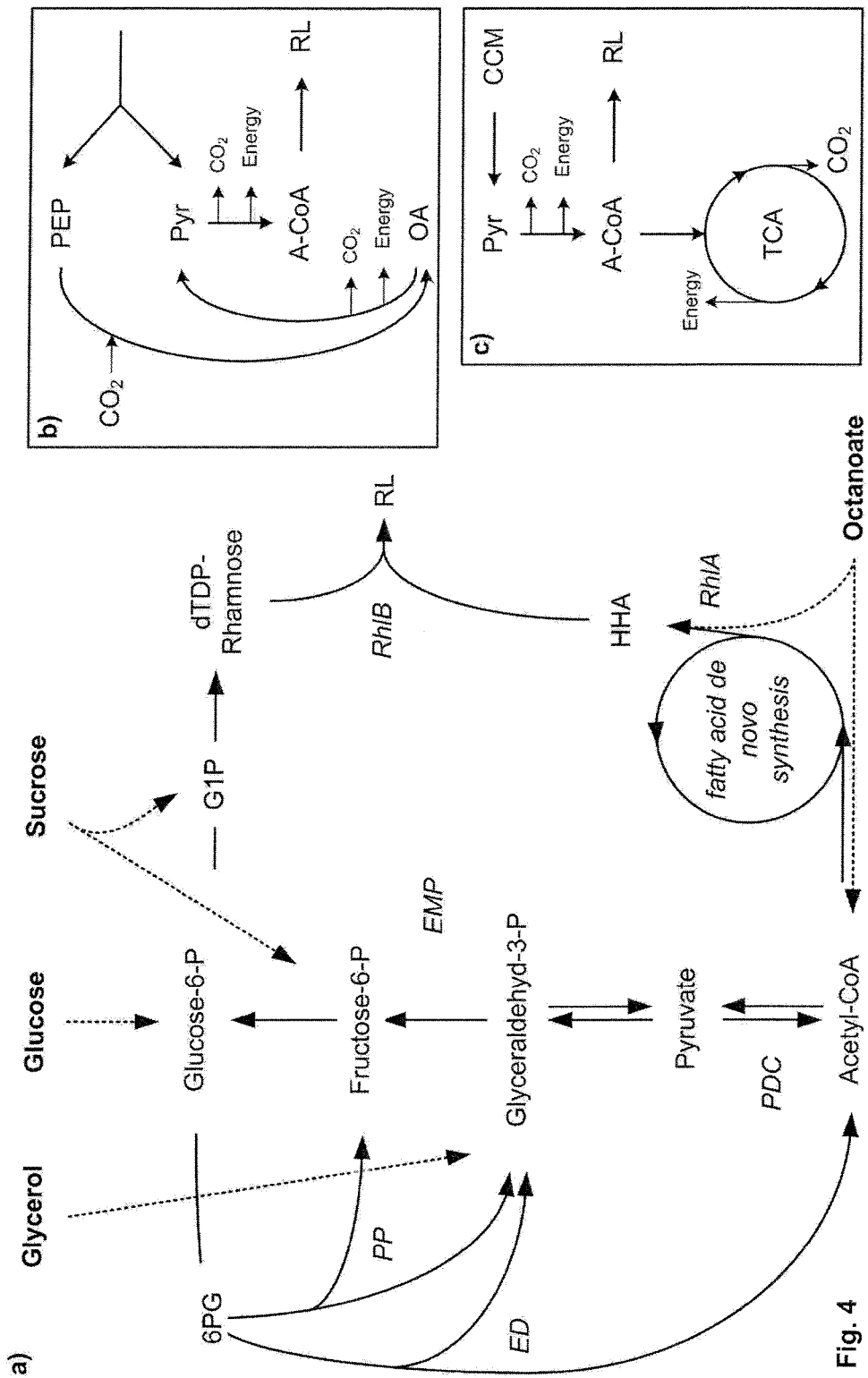
FIG. 4A depicts a schematic overview of utilized pathways during rhamnolipid production by *P. putida*. ED, Entner-Doudoroff pathway; PP, pentose phosphate pathway; PDC, pyruvate decarboxylation; G1P, glucose-1-phosphate; HAA, β-D-(β-D-hydroxyalkanoyloxy)alkanoic acid; RhlA, 3-hydroxyacyl-ACP:3-hydroxyacyl-ACP O-3-hydroxyacyl-transferase; RhlB, rhamnosyltransferase I.
FIG. 4B depicts anaplerotic reactions emerging while ingesting sucrose and sustaining maintenance metabolism. As energy was needed, redox-equivalent-generating reactions were activated.
FIG. 4C depicts reactions that occur in *P. putida* when grown on glucose. Acetyl-CoA was metabolized via the TCA cycle, thereby forming $CO_2$.

To enable the production of rhamnolipids in *P. putida*, the essential genes for rhamnolipid production, located in *P. aeruginosa* on the rhlAB operon (encoding RhlA and RhlB) were introduced. The rhlAB operon of *P. aeruginosa* PA01 was amplified starting at the natural transcription start (Rahim, R, et al., Molecular Microbiology (2001) 40, 3, 708-718) and was cloned into plasmid pVLT33 (Lorenzo et al. 1993b). The resulting recombinant strain *P. putida* KT2440 pVLT33_rhlAB, produced mono-rhamnolipids on LB (lysogeny broth)-medium supplemented with 1% glucose at 30° C. (FIG. 4). In comparison, *P. aeruginosa* PA01, grown in proteose peptone-glucose-ammonium salts (PP-GAS)-medium at 37° C. produced mono- and di-rhamnolipids (FIG. 4, lane 2). Quantification of rhamnolipids using the standard orcinol assay indicated up to 350 mg/L rhamnolipid in the *P. aeruginosa* culture, and about 500 mg/L mono-rhamnolipid in the culture of the newly engineered *P. putida* KT2440 pVLT33_rhlAB.

Figure 5:
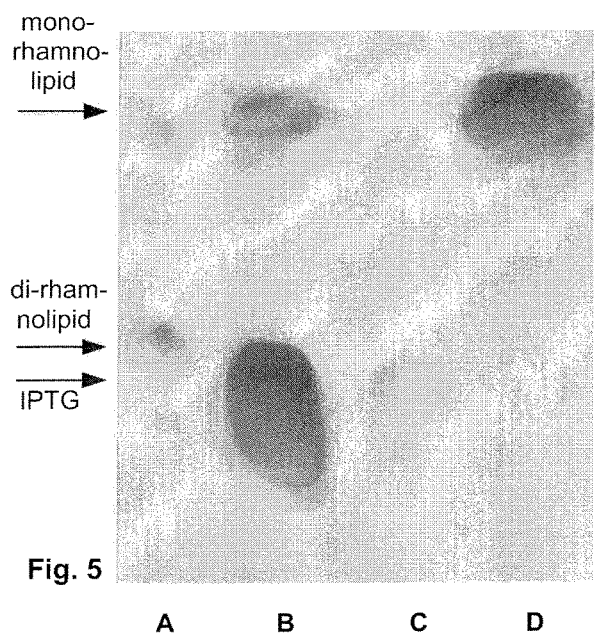
FIG. 5 depicts thin layer chromatography of rhamnolipids (A: rhamnolipid standard; B: *P. aeruginosa* PAO1; C: *P. putida* KT2440 pVLT33 (ev); D: *P. putida* KT2440 pVLT33_rhlAB). The sample of *P. aeruginosa* PAO1 (lane 2), grown in PPGAS-medium at 37° C., contains mono- and di-rhamnolipid as does the rhamnolipid standard (JBR425, Jeneil Biosurfactant Co.) (lane 1). *P. putida*, expressing the rhlAB operon of *P. aeruginosa* from the plasmid pRL1, cultivated in glucose containing LB-medium produced mono-rhamnolipid (lane 4). No rhamnolipid production was observed using the empty vector control pVLT33 (lane 3). The band located above the di-rhamnolipids is IPTG (i.e., lanes 3 and 4).

The product spectrum of *P. putida* KT2440 pVLT33_rhlAB was investigated by HPLC-ESI-MS. The results illustrated that the new strain produces rhamnolipids with fatty acids featuring chain lengths between $C_8$ and $C_{12}$ in different combinations and in addition very low amounts of rhamnolipids with $C_{14}$ and $C_{16}$ chains (FIG. 5). Furthermore, some of the alkyl chains contained one unsaturation. The most abundant rhamnolipid species contained two fatty acids with $C_{10}$ chains. This was also the case for rhamnolipids that contained only one β-hydroxyfatty acid chain. Although, *P. aeruginosa* and *P. putida* KT2440 pVLT33_rhlAB produced rhamnolipids with different number of rhamnose residues, the produced rhamnolipids consisted of alkyl chains with the same length. Hence, rhamnolipid production of *P. aeruginosa* quality (rhlC addition leads to di-rhamnolipid synthesis) using glucose as carbon source was achieved.

Optimizing the Metabolic Network for Rhamnolipid Synthesis

Figure 6:
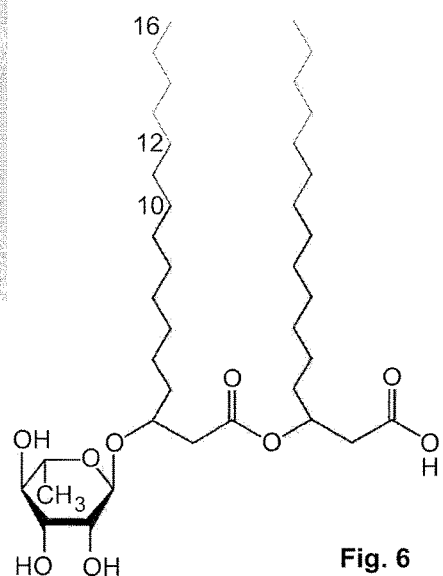
FIG. 6 depicts the molecular structure of mono-rhamnolipids from recombinant *P. putida*. The major compound (C10:C10) is indicated by black lines, while minor compounds are indicated by grey lines.

While the inventors could show that the engineered *P. putida* KT2440 pVLT33_rhlAB produced rhamnolipids, the yield on glucose was significantly below the theoretical limit of 0.7 $Cmol_{rhamnolipid}/Cmol_{glucose}$ (FIG. 3). The inventors therefore investigated the metabolic network to highlight side reactions that potentially function as alternative carbon sinks, with the aim to redistribute the carbon flux towards rhamnolipid production. P. putida uses β-hydroxyacyl-ACP from de-novo fatty acid synthesis as precursor for the storage polymer PHA (Eugenio, L. I., et al., Environmental Microbiology (2010) 12, 1, 207-221; Rehm, B. H. A., et al., J Biol Chem (1998) 273, 37; 24044-24051; Soberón-Chávez G, et al., J Ind Microbiol Biotechnol (2005) 32, 11-12, 675-677). The β-hydroxyacyl-ACP is converted to β-hydroxyacyl-CoA by PhaG β-hydroxyacyl-ACP:CoA transacylase (Zheng, Z., et al., Antonie van Leeuwenhoek (2004) 85, 2, 93-101). PhaC1 poly(3-hydroxyalkanoic acid) synthase 1 catalyzes the reaction leading to PHA (Timm and Steinbüchel 1992). As these reactions compete with formation of hydroxyalkanoyl-alkanoates in the rhamnolipid synthesis pathway for β-hydroxyacyl-ACP, the use of a PhaC1-negative strain was chosen as first optimization target. P. putida KT42C1 (ΔphaC1::Km') (Eugenio et al., 2010, supra), a derivative of P. putida KT2440, was tested as a host for rhamnolipid production. As the knockout was produced using a kanamycine resistance cassette, the rhlAB operon was subcloned into the plasmid pVLT31, a pVLT33 derivative carrying a tetracycline resistance. The new strain P. putida KT42C1 pVLT31_rhlAB produced up to 1.50 g/L of rhamnolipids, three times more than the original strain. The product profile of P. putida KT42C1 pVLT31_rhlAB revealed that not only mono-rhamnolipids, but also up to 20% of the free fatty acid is produced (FIG. 6).

Uncoupling Growth and Rhamnolipid Production

Figure 7:
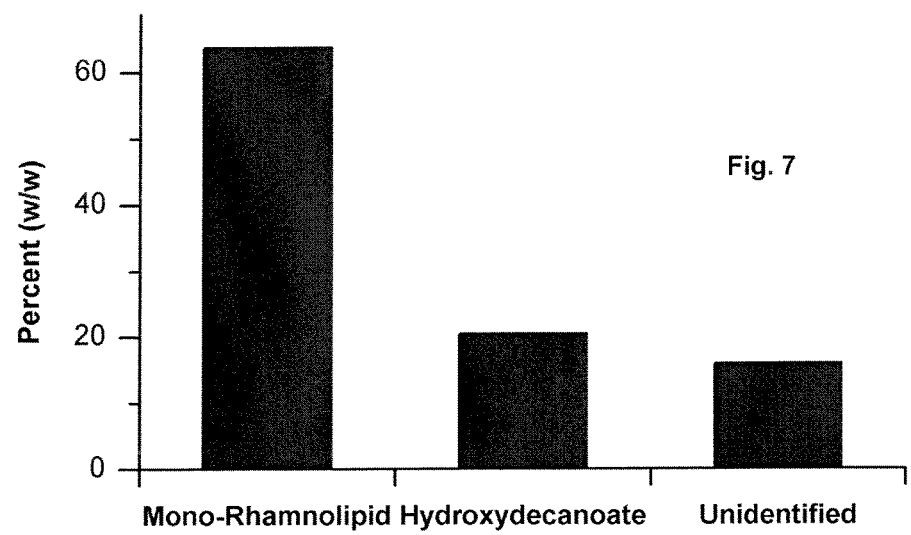
FIG. 7 shows the compounds produced by *P. putida* KT42C1 pVLT31_rhlAB. The bars in grey represent samples eluted with methanol, while the white bars represent samples that were eluted using isopropanol.

Ideally, high production rates can be sustained without biomass formation, resulting in high product yields. During the fermentation, the growth rate of P. putida KT42C1 pVLT31_rhlAB declined (FIG. 7). This growth behavior on LB medium was described for E. coli and is explained by multiauxic growth due to sequential compound uptake (Baev, M. V., et al., Applied Microbiology and Biotechnology (2006) 71, 3, 323-328; Sezonov, G., et al., Journal of Bacteriology (2007) 189, 23, 8746-8749). The kinetics underlying growth of P. putida can best be described by a logistic growth formulation (Equation (1) to (3)).

Although counterintuitive, changing growth rates did not result in changing glucose uptake rates. Importantly, the constant rhamnolipid formation rate suggests that the recombinant regulation of the rhamnolipid synthesis operon cannot be influenced by the host and hence is truly orthogonal during the growth and production phases. Hence, rhamnolipids are produced from cells that minimally or not grow at all, which opens opportunities for long-term stable production with high product yields (FIG. 7). This is especially true, if glucose is the carbon source for rhamnolipid production, while the components of the LB medium are precursors for biomass formation.

To elucidate if glucose primarily serves as substrate for rhamnolipid production by P. putida KT42C1 pVLT31_rhlAB the use of glucose versus the use of alternative carbon sources was discriminated using uniformly labeled $^{13}C_6$-glucose in combination with appropriate analytics. A new off-gas sensor allowed the simultaneous quantification of $^{12}CO_2$ and $^{13}CO_2$ concentrations (BlueSens GmbH, Herten, Germany) applying dual wavelength infrared light. Assuming glucose as the carbon source for rhamnolipid production, the conversion of pyruvate to acetyl-CoA (the monomer of fatty acid polymerization) releases $^{13}CO_2$.

The production of $^{13}CO_2$ did not agree with time-invariant glucose uptake and rhamnolipid production rates, but rather a distinct and abrupt start of glucose metabolization followed by a constant $^{13}CO_2$ production of 0.21-0.27 mmol/ ($g_{CDW}$ h) (CDW: cell dry weight). The specific production rate of $^{13}CO_2$ remained constant until glucose was depleted in the medium (FIG. 8). The growth and glucose uptake kinetics suggest that glucose metabolism is suppressed by LB constituents, followed by glucose catabolism after these constituents are depleted, i.e., multiauxic growth (Behrends, V, et al., Appl Environ Microbiol (2009) 75, 8, 2453-2463). Rhamnolipid production on glucose-complemented LB medium can be divided into two phases, of which the first consists of rapid growth on the most favored carbon substrates contained in the LB medium, while the second phase is characterized by a decreasing growth rate at constant glucose uptake and rhamnolipid production rates, i.e., by gradual uncoupling of biomass and rhamnolipid production.

The new off-gas sensor from BlueSens allowed to rationalize the observed fermentation kinetics and provided valuable insights into metabolic network operation, which is paramount for the development of rhamnolipid production by P. putida KT42C1 pVLT31_rhlAB under non-growth conditions.

In this study, we successfully carried out mono-rhamnolipid synthesis in P. putida. Featuring high resistance against rhamnolipids, simple and controllable production kinetics, and the metabolic ability to produce rhamnolipids with high yield and rate, P. putida proved to be an appropriate host for heterologous rhamnolipid production.

The fermentation of non-pathogenic P. putida was possible using glucose as substrate for the synthesis of mono-rhamnolipids, while constituents of the LB-medium were the carbon sources for cell growth. By using quantitative fermentation kinetics monitoring including advanced off-gas analysis we could show that rhamnolipid production is uncoupled from biomass formation, which offers possibilities for substrate exploitation and process management.

Comparison P. putida vs. P. aeruginosa Rhamnolipid Production

Until now, rhamnolipid production mainly was carried out by P. aeruginosa. However, the inventors developed a functional substitution to the opportunistic pathogenic, nosocomial bacterium. The pathogenicity P. aeruginosa features is a severe hindrance for industrial rhamnolipid production, which was avoided by using non-pathogenic P. putida. Furthermore, our strain features several advantages when compared to rhamnolipid production with P. aeruginosa.

Figure 10:
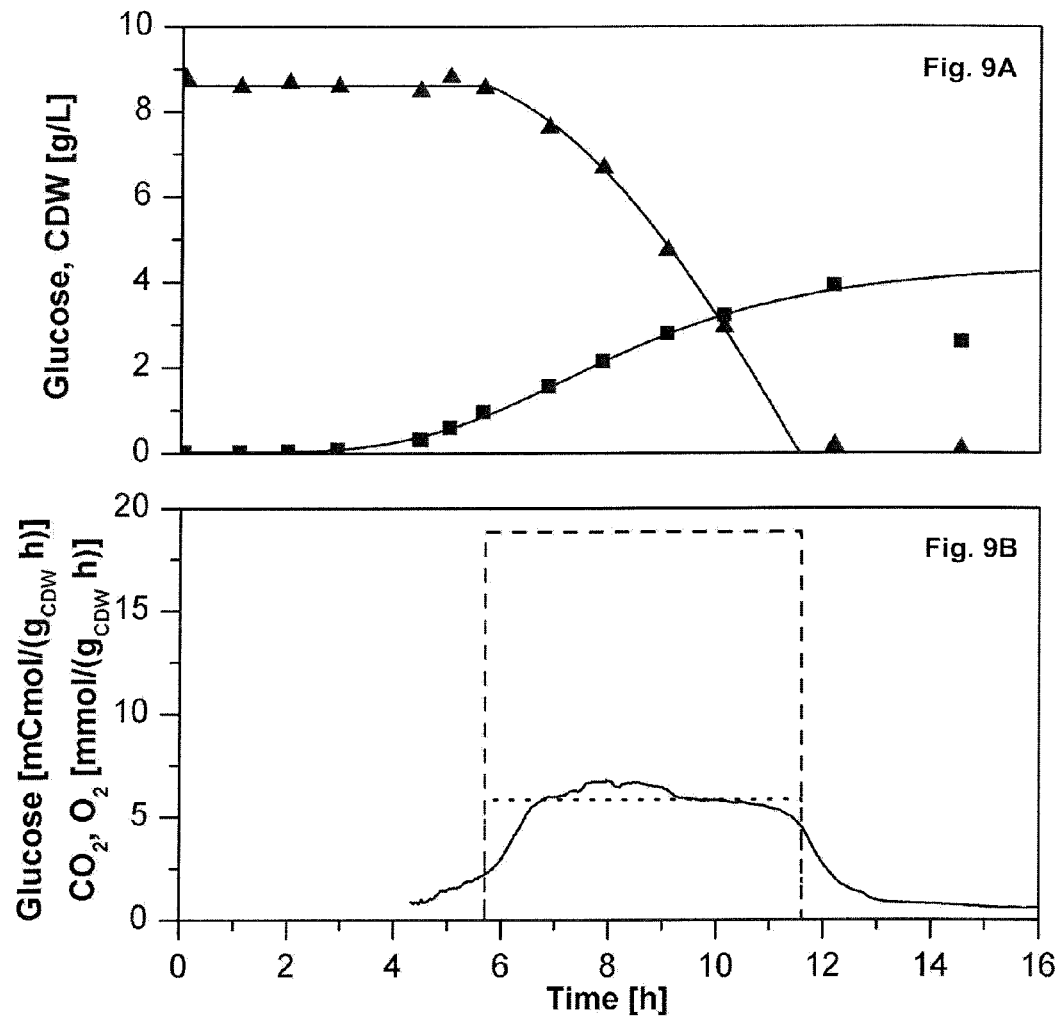
FIG. 10 compares previous approaches of processes of rhamnolipid production and an embodiment of the method of the invention; 1: Cabrera-Valladares, N., et al., Appl Microbiol Biotechnol (2006) 73, 187-194; 2: Ochsner, U. A., et al., Appl Environ Microbiol (1995) 61, 9, 3503-3506; 3: Müller et al. 2010b; 4: Cha, M., et al., Bioresour Technol (2008) 99, 7, 2192-2199; 5: Trummler, K., et al., Eur J Lipid Sci Technol (2003) 105, 536-571; 6: a method according to the invention.*) The specific rhamnolipid production rate was calculated using the given data and represents an average value over the whole fermentation time.

While the achieved rhamnolipid production rate in the experiments amounted to two thirds of the rate observed in the long-time optimized fermentation with P. aeruginosa, the inventors already obtained a higher yield of rhamnolipid on the carbon source (FIG. 10). For industrial production of rhamnolipids, the yield is an important parameter, as it determines the expenses for the substrate. The rate might be increased, by increasing activated rhamnose availability, as observed earlier (Cabrera-Valladares, N., et al., Applied Microbiological Biotechnology (2006) 73, 187-194). Nevertheless, the obtained rhamnolipid titer in the medium is still far from the almost 40 g/L rhamnolipid reported with P. aeruginosa (Müller, 2010), which partly can be explained by the low biomass concentration in our experiments. Fortunately, P. putida is suited for high cell density fermentations. While Kim et al. (J Microbiol Biotechnol (1996) 6, 3, 221-224) achieved 100 $g_{CDW}$/L with P. putida BM01 even higher concentrations were obtained with P. putida KT2442

(Lee, S. Y., et al., Biotechnol Bioeng (2000) 68, 4, 466-470). In another study, with *P. putida* KT2440, cell concentrations of up to 62 $g_{CDW}$/L were achieved (Sun, Z., et al., Appl Microbiol Biotechnol (2006) 71, 4, 423-31).

Substrate Used

An important improvement in comparison to the fermentation of *P. aeruginosa* is the utilization of glucose as substrate instead of hydrophobic substances such as plant oils, despite the theoretical yield benefits of the latter highlighted by our in silico analysis (FIG. 3). Notably, the yield of rhamnolipid on glucose exceeded the yields on carbon substrates reported with *P. aeruginosa*. The main advantage nevertheless is that purification of rhamnolipids from the fermentation broth can be significantly simplified, as the surfactant suspends the hydrophobic substrate in the *P. aeruginosa* fermentation in the aqueous phase. Avoidance of stable substrate/product emulsions using glucose as carbon source results in modest demands on sample preparation for analytical procedures and more importantly to reduced complexity of downstream processing.

Another benefit is that most bacteria grow faster with glucose as carbon source than with fatty acids. Particularly *P. putida* features a high growth rate when growing on glucose (REF). Furthermore, glucose as carbon source is a common substrate in biotechnological production processes, which makes it notably cheaper than for example sunflower acid. These advantages in glucose utilization as carbon source for rhamnolipid production outweigh the downside that the theoretical yield is higher with fatty acids as substrate.

Multiauxie

The basic principle underlying *P. putida*'s high adaptability to the environment including different growth substrates is the so called catabolite repression control (Daniels et al. 2010), leading to diauxic or even multiauxic growth, a phenomenon observed in our experiments. Known examples for diauxic growth are organic acids, being ingested preferred to glucose in *P. fluorescens* (Lynch, W. H., Franklin, M., Arch Microbiol (1978) 118, 2, 133-140) or aromatic compounds, which *P. putida* takes up prior to glucose (Basu, A., et al., Appl Environ Microbiol (2006) 72, 3, 2226-2230). Both behaviours lead to growth curves featuring a diauxic gap, consisting of a saddle point in between two exponential growth phases. In Enterobacteriaceae like *E. coli*, cyclic AMP (cAMP) plays an important role as signal compound in catabolite repression (Postma, P. W., et al., Microbiol Rev (1993) 57, 3, 543-94). Pseudomonads possess a completely different catabolite repressor system, which does not depend on cAMP (Phillips, A. T., J Bacteriol (1981) 145, 3, 1286-1292). Instead a set of five different genes act as global regulators: crc, crp (in *P. aeruginosa* called vfr), cyoB, ptsN, and relA (Daniels. C., et al., J Bacteriol (2010) 192, 8, 2169-2181). To meet the demand by prevailing growth conditions these genes can change the cells metabolic gene expression by substrate-specific-responses involving numerous signaling pathways and regulation of the corresponding metabolic pathways.

For our experiments the crc gene is of particular interest, as it coordinates metabolism and plays a key role in control of sequential amino acid assimilation when *Pseudomonas* grows in complex media. Furthermore, as long as there are still amino acids in the medium, it represses the genes for glucose uptake and metabolization, as glucose is not the preferred carbon source for pseudomonads (Moreno, R., et al. Proteomics (2009) 9, 11, 2910-2928). Furthermore, it reduces the utilization of certain amino acids to switch the metabolism configuration to a more efficient use of the preferred substrates. It thus also optimizes the growth rate to enable it to compete for the available carbon sources (Moreno et al. 2009, supra). Therefore, it is mainly responsible for the multiauxic growth observed here.

Deeper knowledge of the described control and signal processes involved should help improving rhamnolipid production (rate, yield, titer).

Logistic Growth

Logistic growth, as it can be observed in our experiments (FIG. 8) is based on theories about population dynamics. This model is applied in growth situations where the increase in population size is limited by upper boundaries. The general shape of a growth curve is sigmoidal, resulting from zero growth at the beginning, increasing growth to a maximal growth rate and subsequent decreasing growth rates until an asymptote is reached. The logistic model can be utilized to describe such courses. The parameters incorporated in the equation on which logistic growth is based upon resemble the biological parameters of the population. Parameters used are the initial biomass concentration, the final biomass concentration, the time after which half of the biomass is formed, and furthermore a curve form coefficient, which has no direct biological counterpart.

Growth of *P. putida* while producing rhamnolipids can accurately be characterized via a logistic model, as was shown for *P. aeruginosa* (Müller et al. 2010a). Having in mind the phenomenon of multiauxic growth described earlier, it could be that under the chosen cultivation conditions growth of *P. putida* is underlying multiple, shifting, limitations. One may speculate that these growth-limiting boundaries are determined by the availability of the currently metabolized carbon source, which changes frequently, when *P. putida* grows on LB-medium supplemented with glucose. Again, the significant reduction in growth is independent of rhamnolipid production.

In summary, an alternative, non-pathogenic host for rhamnolipid production utilizing glucose as carbon source was successfully developed. The insight into rhamnolipid production with *P. putida* will contribute to the further advance of this host; with the aim to develop an industrially viable process.

B: Production of *Burkholderia glumae* Rhamnolipids in *Pseudomonas putida* KT22440

This example illustrates rhamnolipid production in the phytopathogenic *Burkholderia glumae* PG1, which causes seedling blight and grain rot also called as "panicle blight". *B. glumae* is the only *Burkholderia* species which is used in biotechnology for the production of a lipase on an industrial scale. The inventors have identified the rhamnolipids produced by the wild type strain by mass spectrometry and show that *B. glumae* rhamnolipids have antimicrobial properties towards Gram-positive bacteria. The genes involved in rhamnolipid production were cloned and characterize by heterologous expression in *Pseudomonas putida* KT2440. The data further show that recombinant *P. putida* strains are able to produce the same rhamnolipid species with long chain fatty acids and in higher amounts than the *B. glumae* wild type.

Materials and Methods

Bacterial Strains, Culture Conditions and Plasmids

*Burkholderia glumae* PG1 (Urakami, T., Int. J. Syst. Bacteriol. (1994) 44, 235-245) was cultivated in Minimal medium E (MME) (Vogel, H. J., & Bonner, D. M., (1956) 218, 97-106). The medium was prepared as a 50× stock solution in distilled water (10 g $MgSO_4 \times 7$ $H_2O$, 100 g citrate×$H_2O$, 175 g $Na(NH_4)HPO_4$+4 $H_2O$ and 500 g $K_2HPO_4$ ad 1000 ml $H_2O$), (pH 7.0) and diluted for use with distilled water. Cultures were grown with 1% (wt/vol) glucose, glycerol or olive oil as additional carbon source.

*Pseudomonas putida* KT2440 (Nelson, K. E., et al., Environ. Microbiol. (2002) 4, 799-808), *Bacillus subtilis* TEB1030 (Eggert, T. G., et al., FEBS Lett. (2001) 502, 89-92), *Pseudomonas aeruginosa* PAO1 (Hancock, R. E., & Carey, A. M., (1979) 140, 902-910), *Serratia marcescens* W838 and *Staphylococcus aureus* were cultivated in LB-media (10 g/L tryptone, 5 g/L yeast extract, 10 g/L NaCl) at 37° C. and 30° C. for *P. putida* respectively. All strains were routinely grown over night in 10 mL medium in 100 mL shaking flasks with orbital shaking at 150 rpm. Main cultures with the same volume were inoculated with an optical density at 580 nm ($O.D._{580nm}$) of 0.05 from the starter cultures.

Strains containing the pVLT33 vector (de Lorenzo, V. L., et al., Gene (1993) 123, 17-24) and recombinant plasmids were selected by adding 50 µg/ml kanamycine.

Test cultures for MIC determination were inoculated in deep well microtiter plates with an $O.D._{580nm}$ of 0.05 in 500 µL LB medium supplemented with different concentrations of rhamnolipids. A culture without rhamnolipids served as control.

Construction of Recombinant Plasmids

The rhl-genes of *B. glumae* PG1 were amplified from genomic DNA using PfuTurbo Polymerase (Agilent Technologies, Waldbronn, Germany) as recommended by the supplier and oligonucleotides, obtained from Eurofins MWG Operon (Ebersberg, Germany), with sequences 5'-TTGAATTCGGTTACCGCCGGAGTACGCC (SEQ ID NO: 12) and 5"-TTTTTCTAGATCATGCGCCCGAGGCCTC (SEQ ID NO: 13) for rhlAB operon and 5"-TTTTTCTAGAGCCAACCCTGGTGGCACG (SEQ ID NO: 14) and 5'-TTTAAGCTTTCATCCGTGGCGCACCCG (SEQ ID NO: 15) for rhlC. PCR products were digested with EcoRI/XbaI (rhlAB) and XbaI/HindIII (rhlC) and ligated as single or in combination in the pVLT33 vector, digested with the same enzymes, creating the plasmids pBGRL1-pBGRL3. DNA recombination was according to standard techniques. Transformation of recombinant plasmid in *E. coli* DH5α was done using standard protocol (Hanahan, D., J. Mol. Biol. (1983) 166:557-580). Strains were plated on selecting LB-agar containing 50 µg/ml kanamycine and incubated over night at 37° C.

Transformation of Plasmids and Rhamnolipid Production in *P. Putida*

Competent *P. putida* KT2440 were transformed with pVLT33 and pBGRL1-3 via electroporation according to Choi et al. (Choi, K.-H., et al., J. Microbial. Methods (2006) 64, 391-397). Recombinant strains were selected on LB-agar and liquid cultures containing 50 µg/ml kanamycine and cultivated at 30° C.

For the production of rhamnolipids main cultures supplemented with 2% (wt/vol) glucose and 50 µg/ml kanamycine were incubated to an $O.D._{580nm}$ of 0.5. Expression of rhl-genes was then induced by adding 0.4 mM IPTG to the cultures. Cultures were further incubated at 30° C. and 150 RPM orbital shaking Rhamnolipids were extracted 24 h after induction.

RNA Isolation and qRT-PCR

To determine the transcription level of the gene expression, mRNA was isolated from cell cultures after 24 hours of growth utilizing peqGOLD Bacterial RNA Kit by PEQLAB Biotechnologie GmbH (Erlangen, Germany). A maximum of $1 \times 10^9$ cells was utilized to isolate mRNA for quantitative PCT (qRT-PCR).

Extraction of Rhamnolipids

To extract rhamnolipids 1 ml culture was centrifuged at 13,000 RPM for 3 minutes. Subsequently 100 µl (for analysis via orcinol assay) and 500 µl (for thin layer chromatography) supernatant were removed and spiked three times with ethyl acetate. Samples were mixed on a vortex shaker and centrifuged for 30 sec. at 13,000 RPM. Upper phases were removed and collected. The solvents were evaporated in a vacuum centrifuge.

Thin Layer Chromatography of Rhamnolipids

Thin layer chromatography (TLC) was carried out as described by Heyd et al. (Anal. Bioanal. Chem. (2008) 391, 1579-1590). The evaporated rhamnolipids were dissolved in 20 µl 100% ethanol. 10 µL of this solution were spotted on a silica 60 TLC-plate (Macherey-Nagel, Düren, Germany) together with the same volume of a 0.1% (wt/vol) rhamnolipid standard (JBR425, Jeneil Biosurfactant Co., Saukville, USA). A mixture of chloroform, methanol and acetic acid at a ratio of 65:15:2 was used as the running agent. The solvent for staining was prepared of 0.15 g orcinol, 8.4 mL sulphuric acid (60%) and 42 mL distilled water. The staining solvent was sprayed on the TLC-plates and dried by a blow-dryer.

Rhamnolipid Quantification Using Orcinol Assay

The total amount of rhamnolipids was measured using the standard orcinol assay (Ochsner, U. A., 1993: *Genetics and biochemistry of Pseudomonas aeruginosa rhamnolipid biosurfactant synthesis*. Ph.D. thesis. Swiss Federal Institute of Technology Zürich, Switzerland. The evaporated rhamnolipids were dissolved in 100 µL distilled water. Than 100 µL orcinol solution (1.8% in distilled water) and 800 µL sulphuric acid (60%) were added. The mixture was incubated for 30 min at 80° C. and cooled down to room temperature. The coloured samples were measured at 421 nm and compared to a rhamnolipid standard (JBR425) with different concentrations.

Purification of Rhamnolipids

For the identification of Rhamnolipids via HPLC-ESI-MS *B. glumae* and *P. putida* strains were cultivated in 1 L cultures in 5 L Erlenmeyer flasks, other conditions are as described before. The rhamnolipids were purified according to Deziel et al. (Biochim. Biophys. Acta (1999) 1440, 244-252) with small modifications. Cells were removed by centrifugation (9000×g, 20° C., 20 min). The supernatant was acidified to pH 3.0 with 37% HCL and kept at 4° C. overnight. The precipitated rhamnolipids were recovered by centrifugation (9000×g, 4° C., 30 min) and dissolved in ethyl acetate. The solution was washed three times by acidified water (pH 3), dried with anhydrous magnesium sulphate and evaporated under vacuum. The dried rhamnolipids were dissolved in 0.05 M sodium bicarbonate and the aqueous solution was retreated with 37% HCl. The rhamnolipids were recovered by centrifugation (13000×g, 4° C., 60 min).

Identification of Rhamnolipids by HPLC-ESI-MS

HPLC-MS experiments were carried out on an Agilent 1100 series binary HPLC system (Agilent Technologies, Waldbronn, Germany), equipped with a DAD (190-400 nm) and coupled with the triple quadrupole 4000QTRAP™ mass spectrometer (Applied Biosystem/MDS SCIEX, Foster City, Calif., USA) equipped with a TurboIon spray source. For improving the sensitivity the third quadrupole is used as a linear ion trap (LIT) in the enhanced MS mode.

Separation was achieved on a ProntoSIL 120-C8-SH (Bischoff Chromatography, Leonberg, Germany) column (150×2 mm i.d., 3 µm particle size) kept at 20° C. during analysis. The gradient elution was done with deionized water with 0.1% formic acid (solvent A) and acetonitrile with 0.1% formic acid (solvent B) at a constant flow rate of 300 μl min$^{-1}$ in the following manner: start with 60% B isocratic for 4 min, from 4 to 24 min a linear increase from 60% B to 90% B, followed by a second isocratic step (90% B for 10 min). The return to 60% B was performed in one min and 10 min isocratic (60% B) was used for the re-equilibration. The injection volume was 20 μl.

The MS was used in negative EMS mode scanning from 200-1000 Da. The parameters used were optimized first performing a Flow Injection Analysis (FIA) with a standard and led to the following parameter settings: IS −4500 V, Declustering Potential (DP) −100 V, Curtain Gas ($N_2$) 10 arbitrary units (au), Source Temperature 500° C., Nebulizer Gas ($N_2$) 50 au and Heater Gas ($N_2$) 20 au. Collision energy (CE) and Q3-Entry barrier were set to −5 V and 8 V, respectively, to minimize fragmentation entering the LIT in the full scan mode.

For structural elucidation MS/MS experiments were performed in negative Enhanced Product Ion Scan (EPI) mode. In this mode MS/MS product ions are generated in the Q2 by collision-activated dissociation of selected precursor ions of the Q1 and mass analyzed in a linear ion trap (Q3). Collision Energy (CE) in the range between 30 and 70 V) were used.

Assay of Antimicrobial Activity

Antimicrobial activities were determined as "minimal inhibitory concentrations" (MIC values), defined as lowest concentration of the antimicrobial agent needed to inhibit the development of visible growth after an incubation time of 24 h. Bacteria were grown in LB medium supplemented with increasing amounts of rhamnolipids (10, 20, 40, 80, 150, 200, 250, 300, 400, 500 μg/mL) in deep well microtiter plates which were incubated for 24 hours at 37° C. and 30° C. for *P. putida* respectively. Growth was monitored by measurement of the optical density O.D.$_{580\ nm}$.

Production of Rhamnolipids by *B. glumae*

Figures 11, 12:
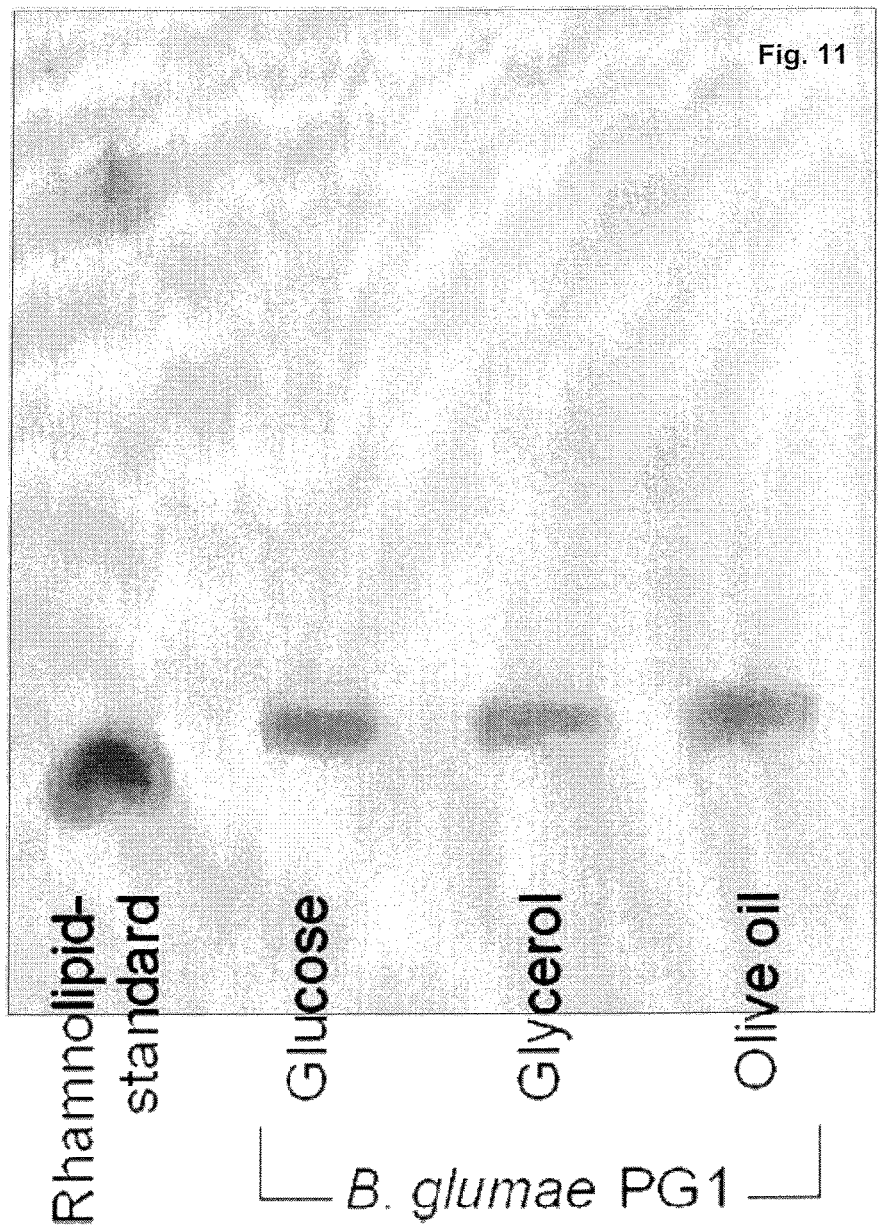
FIG. 11 depicts rhamnolipid production in *B. glumae* PG1 analysed by thin-layer-chromatography after 24 hours of growth. Cultivation was carried out using glucose, glycerol and olive oil as alternative carbon sources. Extracted rhamnolipids were separated on TLC plates and stained as described in the materials and methods section. Highest rhamnolipid production could be achieved using olive oil or glucose, while production was lower with glycerol as the carbon source. Purified rhamnolipids from *P. aeruginosa* that contained mono- and di-rhamnolipids were used as a standard. Extraction and thin-layer-chromatography were done in three separate experiments using independent cultures.
FIG. 12 depicts the results of mass spectrometric analysis of rhamnolipids obtained from *B. glumae* cultures and data on the corresponding mass spectra obtained therefrom. The highest signal appears after 16.58 min indicating a molecular mass of 761.7 m/z for the rhamnolipid with the composition Rha-Rha-$C_{14}$-$C_{14}$. The retention time of 12.65 min accords to a molecular mass of 733.5 m/z meaning a di-rhamnolipid Rha-Rha-$C_{12}$-$C_{14}$ (or Rha-Rha-$C_{14}$-$C_{12}$).

Rhamnolipids have been suggested to play a role in nutrition of the cell by making water insoluble substrates accessible by solubilizing them. In agreement with this report, rhamnolipid production is increased in *B. thailandensis* by cultivation in oil containing media, which is also known for *P. aeruginosa* (Patel, R. M., & Desai, A. J., J. Basic Microbiol. (1997) 37, 281-286), but also in the presence of glycerol (Dubeau, D., Déziel, E. BMC Microbiol. (2009) 9, 263-274). When the biotechnologically relevant strain *Burkholderia* glumae PG1 was grown in the presence of different carbon sources, the strain produced the highest amounts of rhamnolipids in the presence of glucose or olive oil as substrates (FIG. 11, lane 2 and 4), whereas cultivation in the presence of glycerol resulted in a reduced production of rhamnolipid (FIG. 11, lane 3.).

Figure 14B:
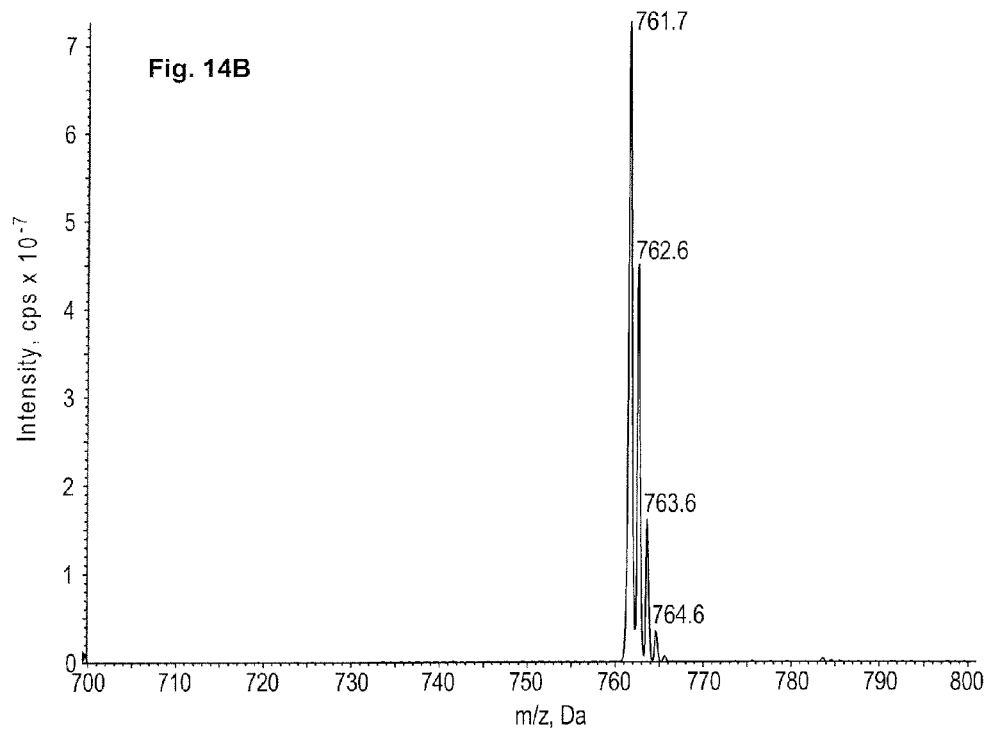
Figure 14C:
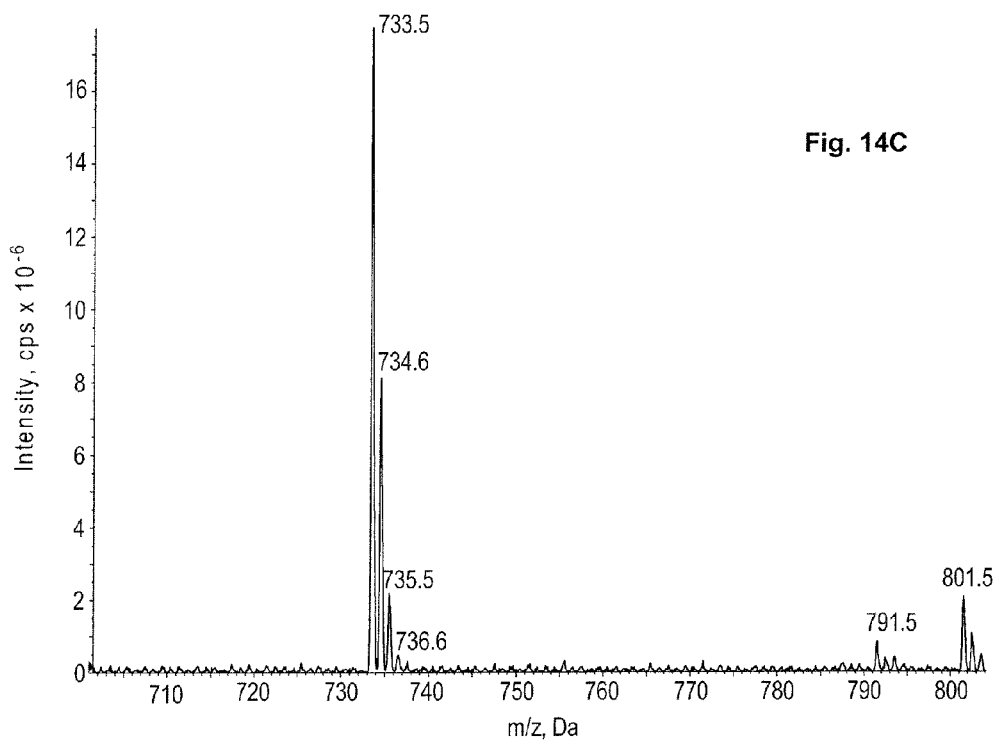
Figure 14D:
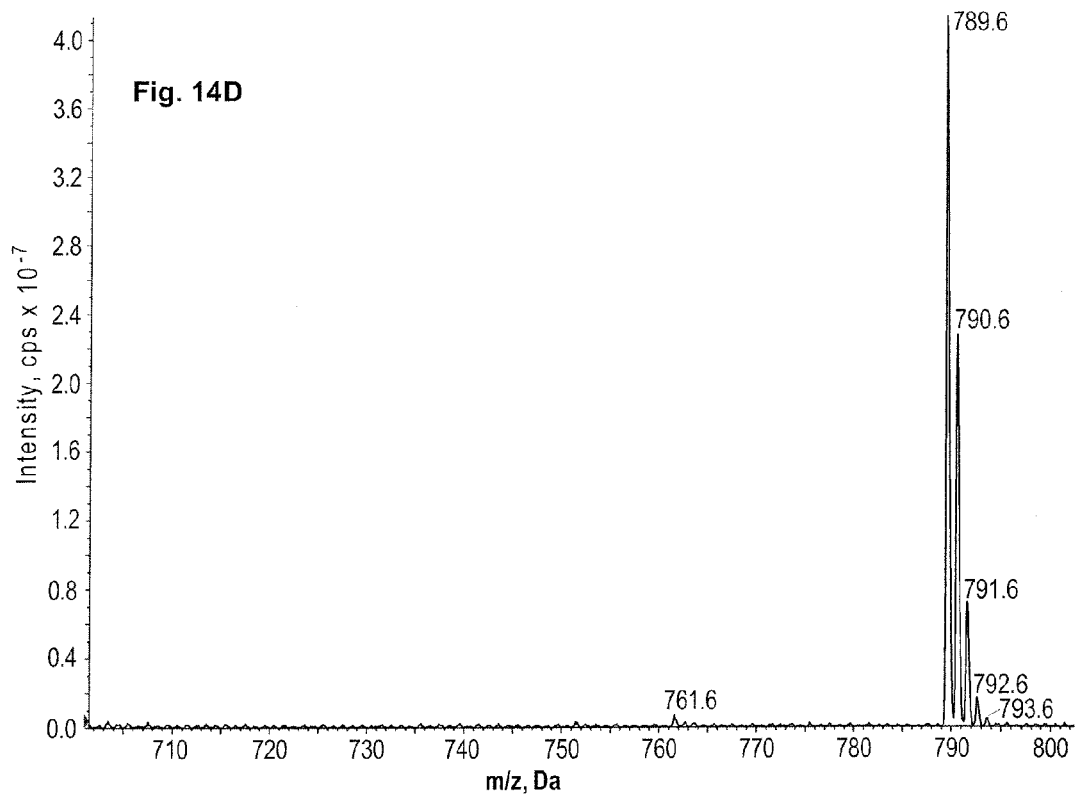

The rhamnolipids produced by *B. glumae* were analyzed by HPLC-ESI-MS. The most prominent species was a di-rhamnolipid with a homodimer hydroxytetradecanoyl-($C_{14}$) chains (Rha-Rha-$C_{14}$-$C_{14}$) corresponding to a signal of 761.7 m/z (FIG. 14B). Two other relevant signals were observed with molecular masses of 733.5 m/z correlating to Rha-Rha-$C_{12}$-$C_{14}$ (or Rha-Rha-$C_{14}$-$C_{12}$,) (FIG. 14 C) and 789.6 m/z correlating to Rha-Rha-$C_{14}$-$C_{16}$ (or Rha-Rha-$C_{16}$-$C_{14}$) (FIG. 14 D).

Identification of Rhl Genes in *B. glumae* PG1

The genome of *B. glumae* PG1 has been sequenced recently (Voget et al., unpublished data). The genome sequence was analysed for homologous of genes known from the rhamnolipid biosynthesis pathway in *P. aeruginosa* and genes with homology to rhlA, rhlB and rhlC could be identified. In contrast to *P. aeruginosa*, in which rhlC is located at a different locus of the chromosome, all three genes responsible for rhamnolipid production were found to be located within a single gene cluster (FIG. 16). An additional gene (COG0477) coding for a putative transporter of the major facilitator family (MFS) is located between rhlAB and rhlC. Other *Burkholderia* strains show the same organisation pattern of rhl encoding genes (FIG. 16). In contrast to other *Burkholderia* species like *B. thailandensis* and *B. pseudomallei*, which contains two identical rhl gene clusters (Dubeau, D., et al., BMC Microbiol. (2009) 9, 263-274), the inventors found only one cluster on the second chromosome in *B. glumae* PG1.

Alignments of protein sequences of rhl genes between *P. aeruginosa* and *B. glumae* vary between 40-50% identities. RhlA shows an identity of 45% (FIG. 17), RhlB of 44% and RhlC of 46% (data not shown).

Functionality of the *B. glumae* Rhl Genes in *P. Putida*

The non-pathogenic bacterium *P. putida* KT2440 is not able to produce rhamnolipids by itself, but heterologous expression of the rhlAB operon from *P. aeruginosa* in this host resulted in the production of mono-rhamnolipid (Ochsner, U. A., et al., Appl. Environ. Microbiol. (1995) 61, 3503-3506). To verify the involvement of the identified *B. glumae* PG1 genes in rhamnolipid production, the rhlAB operon and the rhlC gene were cloned each as a single element and in combinations into the pVLT33 vector and the resulting recombinant plasmids pBGRL1-pBGRL3 were expressed in *P. putida* KT2440.

The expression of the rhlAB operon (pBGRL1) in *P. putida* resulted in the production of mono-rhamnolipid, which forms a typical spot on TLC plate (FIG. 15, Lane 3). In contrast to the mono-rhamnolipid obtained from *P. aeruginosa* (FIG. 15, Lane 1), it runs closer to the solvent front of chromatography. This performance probably based on the longer fatty acid chains in rhamnolipids from *Burkholderia* spp. In addition a further spot is with slightly lower mobility appeared, which may descend from mono-rhamnolipids and probably represents a variant with only one β-hydroxy fatty acid chain (mono-rhamno-mono-lipids). A third spot, which shows a light violet colour instead of the brownish rhamnolipid spots, is located in the range of di-rhamnolipids and originates from the added IPTG. It is visible in all lanes with *P. putida* samples (FIG. 15, lanes 2-4) as well as the control, which was extracted of non grown culture containing same IPTG amount (FIG. 15, lane 9).

Furthermore production of di-rhamnolipids was observed for the first time in *P. putida*, when rhlAB and rhlC (pBGRL3) were expressed (FIG. 15, lane 5). In contrast, cells harbouring the pVLT33 empty vector and rhlC as single gene (pBGRL2) produced no detectable amount of rhamnolipids (FIG. 15, lane 2 and 4).

The amounts of rhamnolipids produced by the recombinant *P. putida* strains were quantified using the orcinol assay. When rhlAB operon was expressed in *P. putida* an amount of 80 mg/L mono-rhamnolipid could routinely be achieved. In comparison 60 mg/L of the mixture of mono- and di-rhamnolipid was produced, when rhlAB and rhlC were expressed. This is a slight improvement to 50 mg/L, which could obtained from *B. glumae* cultures grown with glucose or olive oil and 30 mg/L with glycerol as carbon source.

Analysis of rhamnolipids produced by *P. putida* using HPLC-ESI-MS confirmed the presence of variant species containing fatty acids chains with lengths between $C_{10}$-$C_{14}$ and $C_{14}$-$C_{16}$. The most abundant species contains rhamnolipids with two O-hydroxytetradecanoyl chains ($C_{14}$-$C_{14}$). Furthermore rhamnolipids were found with only one fatty acid, which were probably present in the above mentioned second rhamnolipid spot on TLC plates (data not shown).

Antimicrobial Properties of *B. glumae* Rhamnolipids

Rhamnolipids are potent biotensides which have been found to posses antimicrobial activity against Gram-positive bacteria which are affected in growth upon addition of low concentrations of the tenside (Abalos, A., et al. (2001) Langmuir 17, 1367-1371; Haba, E., et al., Biotechnol. Bioeng. (2003) 81, 316-322; Benincasa, M., et al., (2004) Antonie Van Leeuwenhoek, 85, 1-8).

The mixture of rhamnolipids was tested for their ability to inhibit growth of different Gram-positive and Gram-negative bacteria model strains. Growth of the Gram-positive strains *B. subtilis* and *S. aureus* was abolished upon addition of 10 or 80 µg/ml (FIG. 13) whereas the tested Gram-negative organisms *P. putida*, *P. aeruginosa* and *S. marcescens* were not even affected by concentrations up to 500 µg/ml (FIG. 13). This range of the minimal inhibitory concentrations is comparable to those observed with *P. aeruginosa* rhamnolipids (Sotirova, A. V., et al., Curr. Microbiol. (2008) 56, 639-644) qualifying *B. glumae* rhamnolipids as potent bactericidal biosurfactants.

A consequence of rhamnolipid production appears to be a hydrophobization of the cell itself by rhamnolipid induced removal of hydrophilic LPS from the cell surface of *P. aeruginosa* thereby facilitating intimate contact of cells and hydrophobic phases like oil droplets (Al-Tahhan, R. A., Appl. Environ. Microbiol. (2000) 66, 3262-3268).

Consistent with this role in adaption to hydrophobic environments rhamnolipid production is strongly induced in *P. aeruginosa* when hydrophobic substrates like oils are present in the culture medium (Patel & Desai, 1997, supra).

The same is true for *B. thailandensis* for which oils but also glycerol have been shown to promote rhamnolipid production compared to cultures grown with glucose as the carbon source (Dubeau et al., 2009, supra). In contrast, the highest rhamnolipid production in *B. glumae* could be achieved by cultivation in the presence of oil or glucose and only a reduced amount with glycerol in the culture media. The fact that oil, in this case olive oil, promotes rhamnolipid production is in parallel with the production of a comprehensively characterized bacterial lipase of the family 1.2 by *B. glumae* (Frenken, L. G. J., et al., Mol. Microbiol. (1993) 9, 579-589; Rosenau, F., & Jaeger; K.-J., Biochimie (2000) 82, 1023-1032) which is also induced by hydrophobic substances and produced in industrial scale in oil containing media (Boekema, B. K. H. L., Appl. Environ. Microbiol. (2007) 73, 3838-3844). Extracted rhamnolipids from *B. glumae* show the same composition with long fatty acid chains which is known from other *Burkholderia* species (Dubeau et al., 2009, supra).

In addition they show antimicrobial properties predominantly against Gram-positive bacteria. Similar properties were already shown for the rhamnolipids originating from *P. aeruginosa* which are—compared to their counterparts from *Burkholderia* species—predominantly composed of fatty acids with shorter chain lengths possessing different physicochemical properties (Dubeau et al., 2009, supra). They appear to permeabilize bacterial cells by modifying cell surface properties and interestingly Gram-positive species show a significantly higher susceptibility (Sotirova et al., 2008, supra). Moreover, they can disperse bio films of various microorganisms like the pathogen *Bordetella bronchiseptica* (22) and have been shown to reduce adhesion of *Staphylococcus aureus* and *S. epidermis* to medical prostheses (Rodrigues, L. R., et al., J. Appl. Microbiol. (2006) 100, 470-480).

Genes responsible for rhamnolipid production in *B. glumae* could be identified within a single cluster containing an additional gene (COG0477) between rhlAB and rhlC, which encodes a putative transporter of the major facilitator family (MFS). In comparison, in *P. aeruginosa* rhlC forms an operon together with PA1131, which is probable a transporter of the major facilitator family (MFS), too. Moreover two genes encoding a putative outer membrane factor (OMF) lipoprotein and a secretion protein of the HlyD family lying downstream from rhlC (FIG. 16). OMF proteins operate in conjunction with primary transporters, like the MFS system and form together a complex which allows the export of various solutes (e.g. oligosaccharides).

The involvement of the identified genes in rhamnolipid production could be shown by heterologous expression in *P. putida* KT2440. Rhamnolipids produced by this recombinant strain contain the same long fatty acid chains as those produced by *B. glumae* wild type and as also known from *B. thailandensis* and *B. pseudomallei* (Dubeau et al., 2009, supra). This indicates, that the length of fatty acids used for rhamnolipid synthesis is determined by Rhl proteins depending on their origin and not by availability of predominant fatty acids in the host. Further, the overall amount is in the same range as observed for *B. glumae* wild type and other *Burkholderia* species (Dubeau et al., 2009, supra). Our results further suggest that the gene COG0477, which is located between rhlAB and rhlC in the genome of *B. glumae*, is not involved in rhamnolipid secretion, because without expressing this gene mono- and di-rhamnolipids were secreted by *P. putida* in amounts comparable to the *B. glumae* wild type strain.

In addition rhamnolipids containing only one fatty acid chain were found in recombinant *P. putida* strains. These kinds of rhamnolipids are also known from *P. aeruginosa* (Syldatk, C., et al. Z. Naturforsch. C. (1995) 40, 61-67), but their molecular origin is still speculative. RhlB may be able to link a single β-hydroxy fatty acid to a rhamnose molecule or these variants are generated by degradation of rhamnolipids with two fatty acids by enzymatic hydrolysis of one of the fatty acids. If the latter assumption is true, the fact, that *B. glumae* wild type appears not to produce this kind of rhamnolipids, but that they can be obtained by heterologous expression of the same genes in *P. putida*, suggests that *Pseudomonas* spp. may carry an enzyme removing fatty acids from rhamnolipids.

Heterologous expression of rhl-genes from *B. glumae* resulted in recombinant production of rhamnolipids in *P. putida* at a level comparable to or even higher, for rhamnolipids with long fatty acids, than the *B. glumae* wild type without any optimization of the process. This is especially an advantage to produce only pure mono-rhamnolipid for new applications. Undoubtfully the yield can be further increased and optimization of strains and culture conditions will be part of a further project.

C: Experimental Review of Fermentation Temperatures

Shaking flask cultures of *P. putida* KT2440, *B. glumae*, *P. aeruginosa*, and *P. putida* KT42C1 were grown at 30‰0° C., 33‰0° C., 37‰0° C., 40‰0° C. and 42‰0° C. and analyzed for cell growth and rhamnolipid production. The results indicate there is an optimum in rhamnolipid production around 33‰0° C. and can be seen in FIG. 20.

Surprisingly, replicate cultures produced rhamnolipids with a further rhamnolipid species in addition to mono-rhamnolipids as usual, apparent as an altering peak in Corona-HPLC. FIG. 21 shows the amount of the regular mono-rhamnolipid in the original cultures in comparison to the quantity of the new substance in duplicate cultures.

One skilled in the art would readily appreciate that the present invention is well adapted to carry out the objects and obtain the ends and advantages mentioned, as well as those inherent therein. Further, it will be readily apparent to one skilled in the art that varying substitutions and modifications may be made to the invention disclosed herein without departing from the scope and spirit of the invention. The compositions, methods, procedures, treatments, molecules and specific compounds described herein are presently representative of preferred embodiments are exemplary and are not intended as limitations on the scope of the invention. Changes therein and other uses will occur to those skilled in the art which are encompassed within the spirit of the invention are defined by the scope of the claims. The listing or discussion of a previously published document in this specification should not necessarily be taken as an acknowledgement that the document is part of the state of the art or is common general knowledge.

The disclosure illustratively described herein may suitably be practiced in the absence of any element or elements, limitation or limitations, not specifically disclosed herein. Thus, for example, the terms "comprising", "including," containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible. Thus, it should be understood that although the present disclosure has been specifically disclosed by exemplary embodiments and optional features, modification and variation of the disclosures embodied therein herein disclosed may be resorted to by those skilled in the art, and that such modifications and variations are considered to be within the scope of this disclosure.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group.

The invention claimed is:

1. A host cell comprising
   (a) a rhamnosyltransferase 1A (rhlA) gene or an ortholog thereof, being under the control of a heterologous promoter; and
   (b) a rhamnosyltransferase 1B (rhlB) gene or an ortholog thereof, being under the control of a heterologous promoter,
   wherein said host cell is capable of achieving a carbon yield of more than 0.18 Cmol rhamnolipid/Cmol substrate, wherein the host cell is a *Pseudomonas* sp. and wherein the heterologous promoter has the sequence as depicted in SEQ ID Nos 16, 17, 18, 19 or 20.

2. The host cell of claim 1, wherein the host cell further comprises a rhamnosyltransferase 1C (rhlC) gene or an ortholog thereof, being under the control of a heterologous promoter.

3. The host cell of claim 1, wherein the host cell is incapable of producing poly(3-hydroxyalkanoates) (PHA).

4. The host cell of claim 3, having a knock-out mutation in an endogenous sequence encoding poly(3-hydroxyalkanoic acid) synthase 1.

5. The host cell of claim 1, wherein the host cell is non-pathogenic for a human subject.

6. The host cell of claim 1, wherein the host cell is selected from the group consisting of *Pseudomonas putida, Pseudomonas chlororaphis, Pseudomonas fluorescens, Pseudomonas alcaligenes, Pseudomonas aeruginosa, Pseudomonas cepacia, Pseudomonas clemancea, Pseudomonas collierea, Pseudomonas luteola, Pseudomonas stutzeri,* and *Pseudomonas teessidea.*

7. The host cell of claim 1, wherein the rhlA gene, or the ortholog thereof, is heterologous to the host cell.

8. The host cell of claim 7, wherein the rhlA gene, or the ortholog thereof, is from a *Pseudomonas* sp., *Burkholderia* sp., *Enterobacter* sp., *Pantoea* sp., *Dickeya* sp., *Renibacterium salmoninarum, Cellulomonas cellulans, Tetragenococcus koreensis* or *Acinetobacter calcoaceticus.*

9. The host cell of claim 7, wherein the rhlA gene is from one of *Burkholderia glumae, Burkholderia mallei, Burkholderia pseudomallei, Burkholderia plantarii, Burkholderia gladioli, Dickeya zeae, Pseudomonas aeruginosa, Pseudomonas fluorescens, Pseudomonas putida, Pseudomonas oleovorans, Pseudomonas chlororaphis, Pantoea stewartii, Pantoea ananatis, Enterobacter asburiae* and *Enterobacter hormaechei.*

10. The host cell of claim 1, wherein the rhlB gene, or the ortholog thereof, is heterologous to the host cell.

11. The host cell of claim 1, wherein the rhlB gene, or the ortholog thereof, is from *Pseudomonas aeruginosa, Burkholderia mallei, Burkholderia pseudomallei, Burkholderia thailandensis, Dickeya dadantii* or *Pantoea ananatis.*

12. The host cell of claim 2, wherein the rhlC gene, or the ortholog thereof, is heterologous to the host cell.

13. The host cell of claim 12, wherein said rhlC gene, or the ortholog thereof, is from *Pseudomonas aeruginosa, Burkholderia glumae, Burkholderia pseudomallei* or *Burkholderia mallei.*

14. The host cell of claim 1, wherein said one or more rhamnolipids comprise a mono-rhamnolipid and/or a di-rhamnolipid.

15. The bacterial host cell of claim 1, wherein the one or more rhamnolipids comprise a fatty acid having a main chain comprising about six to about 18 carbon atoms.

16. The host cell of claim 15, wherein the fatty acid is one of 3-hydroxynoctanoic acid, 3-hydroxy-n-octenoic acid, 3-hydroxy-n-octadienoic acid, 3-hydroxy-ndecanoic acid, 3-hydroxy-n-decenoic acid, 3-hydroxy-n-dodecanoic acid, 3-hydroxy-ndodecenoic acid, 3-hydroxy-n-dodecadienoic acid, 3-hydroxy-n-tetradecanoic acid, 3-hydroxy-n-tetradecenoic acid, 3-hydroxy-n-tetradecadienoic acid, 3-hydroxy-nhexadecanoic acid and 3-hydroxy-noctadecanoic acid.

17. A method of producing a rhamnolipid, the method comprising
   (a) culturing a host cell according to claim 1 under conditions allowing rhamnolipid production;
   (b) recovering said rhamnolipid; and optionally
   (c) isolating said rhamnolipid.

18. The method of claim 17, wherein said host cell is fed with glucose, sucrose, glycerol or octanoate as the sole carbon source.

19. The method of claim 17, wherein the rhamnolipid is a mono-rhamnolipid and/or di-rhamnolipid.

20. The method of claim 17, wherein the host cell is cultured at a temperature above 30° C.

* * * * *

SEQUENCE LISTING

```
<160> NUMBER OF SEQ ID NOS: 20

<210> SEQ ID NO 1
<211> LENGTH: 296
<212> TYPE: PRT
<213> ORGANISM: B. glumae PG1

<400> SEQUENCE: 1

Met Pro Ile Glu Lys Gln Val Val Pro Leu Pro Asn Gly Leu Gln Val
1               5                   10                  15

Tyr Val Glu His His Val Tyr Asp Pro Ser Phe Glu Thr Val Ile Leu
                20                  25                  30

Ile Asn Gly Ala Leu Ala Thr Thr Ala Ser Phe Gly Gln Thr Val Arg
            35                  40                  45

Tyr Leu Gly Glu Arg Leu Asn Ser Leu Cys Phe Asp Leu Pro Tyr Ala
    50                  55                  60

Gly Gln Ser Arg Gln His Asn Pro Gly Lys Phe Val Leu Thr Lys Asp
65                  70                  75                  80

Asp Glu Val Asp Ile Leu Leu His Leu Ala Glu Arg Phe Arg Pro Ser
                85                  90                  95

Tyr Leu Leu Ser Val Ser Trp Gly Gly Val Ala Ser Leu Phe Ala Leu
                100                 105                 110

Ser Arg Gly Cys Thr Ser Ile Arg Arg Ala Val Val Ala Ser Phe Ser
            115                 120                 125

Pro Phe Leu Asn Asp Ala Met Val Asp Tyr Val Thr Arg Ala Arg Asp
        130                 135                 140

His Ile Ala Ala Gly Glu Asn Leu His Ala Ala Gln Leu Leu Asn Asp
145                 150                 155                 160

Thr Val Gly Arg Tyr Leu Pro Arg Ile Met Lys Leu Tyr Asn Tyr Arg
                165                 170                 175

Tyr Leu Thr Lys Leu Pro Arg Asp Glu Gln Asp Gln Val Ala Phe His
                180                 185                 190

Val Asn Gln Ile Leu Glu Met Lys Pro Glu Ala Tyr Leu Asp Gln Phe
```

```
            195                 200                 205
Thr Gln Ile Gln Cys Gly Val Lys Phe Ile Asn Gly Glu Leu Asp Glu
    210                 215                 220

Tyr Thr Thr Pro Ala Asp Val Arg Arg Leu Gly Ser Tyr Val Arg Arg
225                 230                 235                 240

Ala Glu Phe Glu Thr Ile Gly Lys Ala Gly His Phe Leu Asp Leu Glu
                245                 250                 255

Gly Arg Gln Gln Gln Glu Asn Val Arg Ala Ala Ile Leu Gly Tyr Phe
            260                 265                 270

Cys Asp Glu Ala Arg Ser Ala Ser Ser Pro Asp Gly Ser Phe Asp Ser
        275                 280                 285

Leu Ser Pro Met Pro Leu Leu Ser
        290                 295

<210> SEQ ID NO 2
<211> LENGTH: 296
<212> TYPE: PRT
<213> ORGANISM: B. glumae BGR

<400> SEQUENCE: 2

Met Pro Ile Glu Lys Gln Val Val Pro Leu Pro Asn Gly Leu Gln Val
1               5                   10                  15

Tyr Val Glu His His Val Tyr Asp Pro Ser Phe Glu Thr Val Ile Leu
                20                  25                  30

Ile Asn Gly Ala Leu Ala Thr Thr Ala Ser Phe Gly Gln Thr Val Arg
            35                  40                  45

Tyr Leu Gly Glu Arg Leu Asn Ser Ile Cys Phe Asp Leu Pro Tyr Ala
50                  55                  60

Gly Gln Ser Arg Gln His Asn Pro Gly Lys Phe Val Leu Thr Lys Asp
65                  70                  75                  80

Asp Glu Val Asp Ile Leu Leu Tyr Leu Thr Glu Arg Phe Arg Pro Ser
                85                  90                  95

Tyr Leu Leu Ser Val Ser Trp Gly Gly Val Ala Ser Leu Phe Ala Leu
            100                 105                 110

Ser Arg Gly Cys Thr Ser Ile Arg Arg Ala Val Val Ala Ser Phe Ser
        115                 120                 125

Pro Phe Leu Asn Asp Ala Met Ile Asp Tyr Val Thr Arg Ala Arg Asp
    130                 135                 140

His Ile Ala Ala Gly Glu Asn Leu His Ala Ala Gln Leu Leu Asn Asp
145                 150                 155                 160

Thr Val Gly Arg Tyr Leu Pro Arg Ile Met Lys Leu Tyr Asn Tyr Arg
                165                 170                 175

Tyr Leu Thr Lys Leu Pro Arg Asp Glu Gln Asp Gln Val Ala Phe His
            180                 185                 190

Val Asn Gln Ile Leu Glu Met Lys Pro Glu Ala Tyr Leu Asp Glu Phe
        195                 200                 205

Thr Arg Ile Gln Cys Gly Val Lys Phe Ile Asn Gly Glu Leu Asp Glu
    210                 215                 220

Tyr Thr Thr Pro Ala Asp Val Arg Arg Leu Gly Ser Tyr Val Arg Arg
225                 230                 235                 240

Ala Glu Phe Glu Thr Ile Ala Lys Thr Gly His Phe Leu Asp Leu Glu
                245                 250                 255

Gly Arg Gln Gln Gln Glu Asn Val Arg Ala Ala Ile Leu Gly Tyr Phe
            260                 265                 270
```

```
Cys Asp Glu Ala Arg Ser Ala Ser Pro Ser Asp Gly Ser Phe Asp Ser
            275                 280                 285

Leu Ser Pro Met Pro Leu Met Ser
        290                 295

<210> SEQ ID NO 3
<211> LENGTH: 300
<212> TYPE: PRT
<213> ORGANISM: B. ambifaria MC40-6

<400> SEQUENCE: 3

Met Pro Thr Glu Lys His Val Val Pro Leu Pro Asn Gly Leu Lys Val
1               5                   10                  15

Tyr Val Glu Arg Asn Val Phe Asp Pro Ser Phe Asp Thr Ala Met Leu
            20                  25                  30

Val Asn Gly Ala Leu Ala Thr Thr Ala Ser Phe Gly Gln Thr Val Gln
        35                  40                  45

Tyr Leu Gly Glu Arg Met Asn Thr Ile Cys Phe Asp Leu Pro Tyr Ala
    50                  55                  60

Gly Gln Ser Arg Gln His Asn Pro Gly Cys Phe Ile Leu Thr Lys Asp
65                  70                  75                  80

Asp Glu Ala Ala Ile Leu Gln His Leu Val Glu His Phe Ala Pro Ala
                85                  90                  95

Phe Leu Val Ser Val Ser Trp Gly Gly Val Ala Ser Leu Phe Ala Leu
            100                 105                 110

Ala Arg Gly Cys Pro Ser Val Arg Arg Ala Ala Ile Cys Ser Phe Ser
        115                 120                 125

Pro Phe Leu Asn Asp Ala Met Val Asp Tyr Val Thr Arg Ala Arg Asp
    130                 135                 140

His Ile Ala Ala Gly Glu Asn Leu Lys Ala Ala Gln Leu Leu Asn Asp
145                 150                 155                 160

Thr Val Gly Arg Tyr Leu Pro Arg Ile Met Lys Leu Tyr Asn Tyr Arg
                165                 170                 175

Tyr Leu Thr Arg Leu Pro Arg Asp Glu Gln Asp Gln Val Ala Phe His
            180                 185                 190

Val Asp Gln Ile Leu Ser Leu Gln Pro Glu Arg Tyr Leu Ser Glu Phe
        195                 200                 205

Ser Asn Ile Gly Ala Glu Leu Leu Phe Val Asn Gly Glu Arg Asp Glu
    210                 215                 220

Tyr Thr Thr Pro Ala Asp Val Arg Gln Leu Ala Ala His Val Pro Arg
225                 230                 235                 240

Ala Arg Phe Ala Thr Ile Pro Asp Ala Gly His Phe Leu Asp Ile Glu
                245                 250                 255

Gly Arg Ala Gln Arg Glu Ala Thr Arg Ala Ala Leu Leu Gly Phe Phe
            260                 265                 270

Cys Asp Ala Pro Pro Val Ala Ala Gly Val Gly Leu Gly Ala Ala His
        275                 280                 285

Ala Cys Val Ser Ala Pro Met Pro Ala Met Ser Ser
    290                 295                 300

<210> SEQ ID NO 4
<211> LENGTH: 300
<212> TYPE: PRT
<213> ORGANISM: B. cenocepacia MC0-3

<400> SEQUENCE: 4
```

-continued

```
Met Pro Thr Glu Lys His Val Val Pro Leu Pro Asn Gly Leu Lys Val
1               5                   10                  15

Tyr Val Glu Arg Asn Val Phe Asp Pro Ala Phe Asp Thr Ala Met Leu
                20                  25                  30

Val Asn Gly Ala Leu Ala Thr Thr Ala Ser Phe Gly Gln Thr Val Gln
            35                  40                  45

Tyr Leu Gly Glu Arg Met Asn Thr Ile Cys Phe Asp Leu Pro Tyr Ala
    50                  55                  60

Gly Gln Ser Arg Gln His Asn Pro Gly Cys Phe Ile Leu Thr Lys Asp
65                  70                  75                  80

Asp Glu Ala Ala Ile Leu Gln Tyr Leu Val Glu His Phe Ala Pro Ala
                85                  90                  95

Tyr Leu Val Ser Val Ser Trp Gly Gly Val Ala Ser Leu Phe Ala Leu
            100                 105                 110

Ala Arg Gly Cys Pro Ser Val Arg Arg Ala Ala Ile Cys Ser Phe Ser
        115                 120                 125

Pro Phe Leu Asn Asp Ala Met Val Asp Tyr Val Thr Arg Ala Arg Asp
    130                 135                 140

His Ile Ala Ala Gly Glu Asn Leu Lys Ala Ala Gln Leu Leu Asn Asp
145                 150                 155                 160

Thr Val Gly Arg Tyr Leu Pro Arg Ile Met Lys Leu Tyr Asn Tyr Arg
                165                 170                 175

Tyr Leu Thr Arg Leu Pro Arg Asp Glu Gln Asp Gln Val Ala Phe His
            180                 185                 190

Val Asp Gln Ile Leu Ser Leu Gln Pro Glu Arg Tyr Phe Ser Glu Phe
        195                 200                 205

Ala Asn Ile Gly Cys Glu Leu Leu Phe Leu Asn Gly Glu Arg Asp Glu
    210                 215                 220

Tyr Thr Thr Pro Ala Asp Val Arg Gln Leu Gly Ala His Val Ala Arg
225                 230                 235                 240

Ala Arg Phe Ala Thr Val Pro Asp Ala Gly His Phe Leu Asp Ile Glu
                245                 250                 255

Gly Arg Ala Gln Arg Glu Tyr Thr Arg Ala Ala Leu Leu Asp Phe Phe
            260                 265                 270

Cys Gly Glu Ala Ala Ala Ala Gly Val Thr Arg Ala Ala Ala His
        275                 280                 285

Ala Cys Val Pro Thr Pro Met His Ala Leu Ser Ser
    290                 295                 300
```

<210> SEQ ID NO 5
<211> LENGTH: 300
<212> TYPE: PRT
<213> ORGANISM: B. cepacia AMMD

<400> SEQUENCE: 5

```
Met Pro Thr Glu Lys His Val Val Pro Leu Pro Asn Gly Leu Lys Val
1               5                   10                  15

Tyr Val Glu Arg Asn Val Phe Asp Pro Ser Phe Asp Thr Ala Met Leu
                20                  25                  30

Val Asn Gly Ala Leu Ala Thr Thr Ala Ser Phe Gly Gln Thr Val Gln
            35                  40                  45

Tyr Leu Gly Glu Arg Met Asn Thr Ile Cys Phe Asp Leu Pro Tyr Ala
    50                  55                  60

Gly Gln Ser Arg Gln His Asn Pro Gly Cys Phe Ile Leu Thr Lys Asp
65                  70                  75                  80
```

```
Asp Glu Ala Ala Ile Leu Gln His Leu Val Glu His Phe Ala Pro Ala
                85                  90                  95

Phe Leu Val Ser Val Ser Trp Gly Gly Val Ala Ser Leu Phe Ala Leu
            100                 105                 110

Ala Arg Gly Cys Pro Ser Val Arg Arg Ala Ala Ile Cys Ser Phe Ser
            115                 120                 125

Pro Phe Leu Asn Asp Ala Met Val Asp Tyr Val Thr Arg Ala Arg Asp
        130                 135                 140

His Ile Ala Ala Gly Glu Asn Leu Lys Ala Ala Gln Leu Leu Asn Asp
145                 150                 155                 160

Thr Val Gly Arg Tyr Leu Pro Arg Ile Met Lys Leu Tyr Asn Tyr Arg
                165                 170                 175

Tyr Leu Thr Arg Leu Pro Arg Asp Glu Gln Asp Gln Val Ala Phe His
            180                 185                 190

Val Asp Gln Ile Leu Ser Leu Gln Pro Glu Arg Tyr Leu Ser Glu Phe
        195                 200                 205

Ser Asn Ile Gly Ala Glu Leu Leu Phe Val Asn Gly Glu Arg Asp Glu
210                 215                 220

Tyr Thr Thr Pro Ala Asp Val Arg Gln Leu Ala Ala His Val Pro Arg
225                 230                 235                 240

Ala Arg Phe Gly Thr Ile Pro Asp Ala Gly His Phe Leu Asp Ile Glu
                245                 250                 255

Gly Arg Ala Gln Arg Glu Ala Thr Arg Ala Ala Leu Leu Gly Phe Phe
            260                 265                 270

Cys Asp Ala Pro Pro Val Ala Ala Gly Val Gly Leu Gly Ala Ala His
        275                 280                 285

Pro Cys Val Ser Ala Pro Met Pro Ala Met Ser Ser
        290                 295                 300

<210> SEQ ID NO 6
<211> LENGTH: 299
<212> TYPE: PRT
<213> ORGANISM: B. mallei ATCC23344

<400> SEQUENCE: 6

Met Pro Ile Glu Lys Gln Val Val Ala Leu Pro Ser Gly Leu Lys Val
1               5                   10                  15

His Val Glu Arg His Val Phe Asp Pro Ala Phe Glu Thr Val Ile Leu
                20                  25                  30

Val Asn Gly Ala Leu Ala Thr Thr Ala Ser Phe Gly Gln Thr Ile Arg
            35                  40                  45

Tyr Leu Gly Glu Arg Val Asn Ala Val Cys Phe Asp Leu Pro Tyr Ala
        50                  55                  60

Gly Gln Ser Arg Gln His Asn Pro Gly Glu Tyr Ile Leu Thr Lys Asp
65                  70                  75                  80

Asp Glu Val Glu Ile Leu Leu His Leu Ala Glu Arg Phe Glu Pro Ser
                85                  90                  95

Leu Leu Leu Ser Val Ser Trp Gly Gly Val Ala Ser Leu Phe Ala Leu
            100                 105                 110

Ala Arg Gly Cys Ala Ser Val Arg Arg Ala Val Ile Ala Ser Phe Ser
            115                 120                 125

Pro Phe Leu Asn Asp Ala Met Thr Asp Tyr Val Thr Arg Ala Arg Asp
        130                 135                 140

His Ile Ala Ala Gly Glu Asn Leu Lys Ala Ala Gln Leu Leu Asn Asp
```

```
            145                 150                 155                 160
Thr Val Gly Arg Tyr Leu Pro Arg Ile Met Lys Leu Tyr Asn Tyr Arg
                    165                 170                 175
Tyr Leu Thr Lys Leu Pro Arg Asn Glu Gln Asp Gln Val Ala Phe His
                180                 185                 190
Val Asp Gln Ile Leu Ala Met Gln Pro Glu Gln Tyr Leu Pro Glu Phe
            195                 200                 205
Arg Gln Ile Gly Cys Ala Val Lys Phe Ile Asn Gly Glu Leu Asp Glu
        210                 215                 220
Tyr Thr Ala Ala Ser Asp Val Arg Arg Leu Ala Ala Tyr Val Arg Arg
225                 230                 235                 240
Ala Glu Phe Ala Thr Ile Arg Gln Ala Gly His Phe Leu Asp Leu Glu
                245                 250                 255
Gly Arg Gln Gln Gln Glu Gln Val Arg Ala Ala Val Leu Gly Phe Phe
            260                 265                 270
Ala Asp Glu Arg Ala Ser Ala Ala Arg Asp Ala Ala Gln Asp Glu Thr
        275                 280                 285
Leu Ala Pro Leu Gly Gln Leu Pro Ala Leu Ser
    290                 295

<210> SEQ ID NO 7
<211> LENGTH: 299
<212> TYPE: PRT
<213> ORGANISM: B. pseudomallei K96243

<400> SEQUENCE: 7

Met Pro Ile Glu Lys Gln Val Val Ala Leu Pro Ser Gly Leu Lys Val
1               5                   10                  15
His Val Glu Arg His Val Phe Asp Pro Thr Phe Glu Thr Val Ile Leu
                20                  25                  30
Val Asn G

```
Tyr Thr Thr Ala Ser Asp Val Arg Arg Leu Ala Ala Tyr Val Arg Arg
225                 230                 235                 240

Ala Glu Phe Ala Thr Ile Arg Gln Ala Gly His Phe Leu Asp Leu Glu
                245                 250                 255

Gly Arg Gln Gln Gln Glu Gln Val Arg Ala Ala Val Leu Gly Phe Phe
            260                 265                 270

Ala Asp Glu Arg Ala Ser Ala Ala Arg Asp Ala Ala Gln Asp Glu Thr
        275                 280                 285

Leu Ala Pro Leu Gly Gln Leu Pro Ala Leu Ser
    290                 295

<210> SEQ ID NO 8
<211> LENGTH: 299
<212> TYPE: PRT
<213> ORGANISM: B. thailandensis E264

<400> SEQUENCE: 8

Met Pro Ile Glu Lys Gln Val Val Ala Leu Pro Ser Gly Leu Lys Val
1               5                   10                  15

His Val Glu Arg His Val Phe Asp Pro Ala Phe Glu Thr Val Ile Leu
            20                  25                  30

Val Asn Gly Ala Leu Ala Thr Thr Ala Ser Phe Gly Gln Thr Ile Arg
        35                  40                  45

Tyr Leu Gly Glu Ar

<210> SEQ ID NO 9
<211> LENGTH: 295
<212> TYPE: PRT
<213> ORGANISM: P. aeruginosa PAO1

<400> SEQUENCE: 9

Met Arg Arg Glu Ser Leu Leu Val Ser Val Cys Lys Gly Leu Arg Val
1               5                   10                  15

His Val Glu Arg Val Gly Gln Asp Pro Gly Arg Ser Thr Val Met Leu
            20                  25                  30

Val Asn Gly Ala Met Ala Thr Thr Ala Ser Phe Ala Arg Thr Cys Lys
        35                  40                  45

Cys Leu Ala Glu His Phe Asn Val Val Leu Phe Asp Leu Pro Phe Ala
    50                  55                  60

Gly Gln Ser Arg Gln His Asn Pro Gln Arg Gly Leu Ile Thr Lys Asp
65                  70                  75                  80

Asp Glu Val Glu Ile Leu Leu Ala Leu Ile Glu Arg Phe Glu Val Asn
                85                  90                  95

His Leu Val Ser Ala Ser Trp Gly Gly Ile Ser Thr Leu Leu Ala Leu
            100                 105                 110

Ser Arg Asn Pro Arg Gly Ile Arg Ser Ser Val Val Met Ala Phe Ala
        115                 120                 125

Pro Gly Leu Asn Gln Ala Met Leu Asp Tyr Val Gly Arg Ala Gln Ala
    130                 135                 140

Leu Ile Glu Leu Asp Asp Lys Ser Ala Ile Gly His Leu Leu Asn Glu
145                 150                 155                 160

Thr Val Gly Lys Tyr Leu Pro Gln Arg Leu Lys Ala Ser Asn His Gln
                165                 170                 175

His Met Ala Ser Leu Ala Thr Gly Glu Tyr Glu Gln Ala Arg Phe His
            180                 185                 190

Ile Asp Gln Val Leu Ala Leu Asn Asp Arg Gly Tyr Leu Ala Cys Leu
        195                 200                 205

Glu Arg Ile Gln Ser His Val His Phe Ile Asn Gly Ser Trp Asp Glu
    210                 215                 220

Tyr Thr Thr Ala Glu Asp Ala Arg Gln Phe Arg Asp Tyr Leu Pro His
225                 230                 235                 240

Cys Ser Phe Ser Arg Val Glu Gly Thr Gly His Phe Leu Asp Leu Glu
                245                 250                 255

Ser Lys Leu Ala Ala Val Arg Val His Arg Ala Leu Leu Glu His Leu
            260                 265                 270

Leu Lys Gln Pro Glu Pro Gln Arg Ala Glu Arg Ala Ala Gly Phe His
        275                 280                 285

Glu Met Ala Ile Gly Tyr Ala
    290                 295

<210> SEQ ID NO 10
<211> LENGTH: 30
<212> TYPE: DNA
<213> ORGANISM: artificial
<220> FEATURE:
<223> OTHER INFORMATION: sense primer for rhlAB operon from P.
      aeruginosa PAO1

<400> SEQUENCE: 10
ttgaattcca tcggctacgc gtgaacacgg                                    30

-continued

```
<210> SEQ ID NO 11
<211> LENGTH: 30
<212> TYPE: DNA
<213> ORGANISM: artificial
<220> FEATURE:
<223> OTHER INFORMATION: antisense primer for rhlAB operon from P.
      aeruginosa PAO1

<400> SEQUENCE: 11
tttttctaga tcaggacgca gccttcagcc                                      30

<210> SEQ ID NO 12
<211> LENGTH: 28
<212> TYPE: DNA
<213> ORGANISM: artificial
<220> FEATURE:
<223> OTHER INFORMATION: primer for rhl-genes of B. glumae PG1

<400> SEQUENCE: 12
ttgaattcgg ttaccgccgg agtacgcc                                        28

<210> SEQ ID NO 13
<211> LENGTH: 28
<212> TYPE: DNA
<213> ORGANISM: artificial
<220> FEATURE:
<223> OTHER INFORMATION: primer for rhl-genes of B. glumae PG1

<400> SEQUENCE: 13
tttttctaga tcatgcgccc gaggcctc                                        28

<210> SEQ ID NO 14
<211> LENGTH: 28
<212> TYPE: DNA
<213> ORGANISM: artificial
<220> FEATURE:
<223> OTHER INFORMATION: primer for rhl-genes of B. glumae PG1

<400> SEQUENCE: 14
tttttctaga gccaaccctg gtggcacg                                        28

<210> SEQ ID NO 15
<211> LENGTH: 27
<212> TYPE: DNA
<213> ORGANISM: artificial
<220> FEATURE:
<223> OTHER INFORMATION: primer or rhl-genes of B. glumae PG1

<400> SEQUENCE: 15
tttaagcttt catccgtggc gcacccg                                         27

<210> SEQ ID NO 16
<211> LENGTH: 40
<212> TYPE: DNA
<213> ORGANISM: artificial
<220> FEATURE:
<223> OTHER INFORMATION: consensus sequence of a synthetic promoter
      sequence
<220> FEATURE:
<221> NAME/KEY: misc
<222> LOCATION: (1)..(1)
<223> OTHER INFORMATION: d is a, t or g
<220> FEATURE:
<221> NAME/KEY: misc
<222> LOCATION: (2)..(2)
<223> OTHER INFORMATION: d is a, t or g
<220> FEATURE:
<221> NAME/KEY: misc
```

-continued

```
<222> LOCATION: (3)..(3)
<223> OTHER INFORMATION: b is c, t or g
<220> FEATURE:
<221> NAME/KEY: misc
<222> LOCATION: (4)..(4)
<223> OTHER INFORMATION: n is a, t, c, or g
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc
<222> LOCATION: (5)..(5)
<223> OTHER INFORMATION: s is g or c
<220> FEATURE:
<221> NAME/KEY: misc
<222> LOCATION: (12)..(12)
<223> OTHER INFORMATION: h is a, t or c
<220> FEATURE:
<221> NAME/KEY: misc
<222> LOCATION: (13)..(13)
<223> OTHER INFORMATION: d is g, t or a
<220> FEATURE:
<221> NAME/KEY: misc
<222> LOCATION: (14)..(14)
<223> OTHER INFORMATION: s is g or c
<220> FEATURE:
<221> NAME/KEY: misc
<222> LOCATION: (15)..(15)
<223> OTHER INFORMATION: b is t, c or g
<220> FEATURE:
<221> NAME/KEY: misc
<222> LOCATION: (16)..(16)
<223> OTHER INFORMATION: y is c or t
<220> FEATURE:
<221> NAME/KEY: misc
<222> LOCATION: (17)..(17)
<223> OTHER INFORMATION: d is g, a or t
<220> FEATURE:
<221> NAME/KEY: misc
<222> LOCATION: (18)..(18)
<223> OTHER INFORMATION: b is g, t or c
<220> FEATURE:
<221> NAME/KEY: misc
<222> LOCATION: (19)..(19)
<223> OTHER INFORMATION: d is a, t or g
<220> FEATURE:
<221> NAME/KEY: misc
<222> LOCATION: (20)..(20)
<223> OTHER INFORMATION: d is a, t or g
<220> FEATURE:
<221> NAME/KEY: misc
<222> LOCATION: (21)..(21)
<223> OTHER INFORMATION: n is a, t, c or g
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc
<222> LOCATION: (22)..(22)
<223> OTHER INFORMATION: h is a, c or t
<220> FEATURE:
<221> NAME/KEY: misc
<222> LOCATION: (23)..(23)
<223> OTHER INFORMATION: d is t, g or a
<220> FEATURE:
<221> NAME/KEY: misc
<222> LOCATION: (24)..(24)
<223> OTHER INFORMATION: b is t, c or g
<220> FEATURE:
<221> NAME/KEY: misc
<222> LOCATION: (25)..(25)
<223> OTHER INFORMATION: s is g or c
<220> FEATURE:
<221> NAME/KEY: misc
<222> LOCATION: (26)..(26)
<223> OTHER INFORMATION: h is a, t or c
<220> FEATURE:
```

```
<221> NAME/KEY: misc
<222> LOCATION: (27)..(27)
<223> OTHER INFORMATION: h is a, t or c
<220> FEATURE:
<221> NAME/KEY: misc
<222> LOCATION: (28)..(28)
<223> OTHER INFORMATION: k is g or t
<220> FEATURE:
<221> NAME/KEY: misc
<222> LOCATION: (35)..(35)
<223> OTHER INFORMATION: d is a, g or t
<220> FEATURE:
<221> NAME/KEY: misc
<222> LOCATION: (36)..(36)
<223> OTHER INFORMATION: h is t, a or c
<220> FEATURE:
<221> NAME/KEY: misc
<222> LOCATION: (37)..(37)
<223> OTHER INFORMATION: h is t, a or c
<220> FEATURE:
<221> NAME/KEY: misc
<222> LOCATION: (38)..(38)
<223> OTHER INFORMATION: n is a, t, c or g
<220> FEATURE:
<221> NAME/KEY: misc_feature
<222> LOCATION: (38)..(38)
<223> OTHER INFORMATION: n is a, c, g, or t
<220> FEATURE:
<221> NAME/KEY: misc
<222> LOCATION: (39)..(39)
<223> OTHER INFORMATION: s is g or c
<220> FEATURE:
<221> NAME/KEY: misc
<222> LOCATION: (40)..(40)
<223> OTHER INFORMATION: b is t, g or c

<400> SEQUENCE: 16
ddbnsttgac ahdsbydbdd nhdbshhkta taatdhhnsb                         40

<210> SEQ ID NO 17
<211> LENGTH: 40
<212> TYPE: DNA
<213> ORGANISM: artificial
<220> FEATURE:
<223> OTHER INFORMATION: synthetic promoter sequence

<400> SEQUENCE: 17
agctcttgac aaggtcggaa aattgaagta taatatcagt                         40

<210> SEQ ID NO 18
<211> LENGTH: 40
<212> TYPE: DNA
<213> ORGANISM: artificial
<220> FEATURE:
<223> OTHER INFORMATION: synthetic promoter sequence

<400> SEQUENCE: 18
tttccttgac aagcctagtt tcgccattta taatgactcg                         40

<210> SEQ ID NO 19
<211> LENGTH: 40
<212> TYPE: DNA
<213> ORGANISM: artificial
<220> FEATURE:
<223> OTHER INFORMATION: synthetic promoter sequence

<400> SEQUENCE: 19
ggtggttgac attggcatta caacgtatta taatttagcg                         40

<210> SEQ ID NO 20
<211> LENGTH: 40
```

```
<212> TYPE: DNA
<213> ORGANISM: artificial
<220> FEATURE:
<223> OTHER INFORMATION: synthetic promoter sequence

<400> SEQUENCE: 20
tagagttgac acaccttcgg gtgggcctta taatactcgc                            40
```